(12) United States Patent
Fishman

(10) Patent No.: US 6,699,663 B1
(45) Date of Patent: *Mar. 2, 2004

(54) MOLECULAR SEQUENCE OF SWINE RETROVIRUS

(75) Inventor: Jay A. Fishman, Wellesley, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/661,858

(22) Filed: Sep. 14, 2000

Related U.S. Application Data

(60) Division of application No. 08/766,528, filed on Dec. 13, 1996, now Pat. No. 6,190,861, which is a continuation-in-part of application No. 08/572,645, filed on Dec. 14, 1995, now abandoned.

(51) Int. Cl.[7] .......................... C12Q 1/68; C07H 19/00; C07H 21/00; C07H 21/02

(52) U.S. Cl. .......................... 435/6; 435/91.1; 435/91.2; 536/22.1; 536/23.1; 536/24.3; 536/24.33

(58) Field of Search .......................... 435/6, 91.1, 91.2; 536/22.1, 23.1, 24.3, 24.33

(56) References Cited

U.S. PATENT DOCUMENTS

| | | | |
|---|---|---|---|
| 5,089,386 A | 2/1992 | Stackebrandet et al. | 435/6 |
| 5,614,187 A | 3/1997 | Sachs | 424/93.21 |
| 6,190,861 B1 * | 2/2001 | Fishman | 435/5 |

FOREIGN PATENT DOCUMENTS

| | | |
|---|---|---|
| WO | WO 93/04169 | 3/1993 |
| WO | WO 95/31566 | 11/1995 |
| WO | WO 97/21836 | 6/1997 |

OTHER PUBLICATIONS

Suzuka et al., "Molecular Cloning of Unintegrated Closed Circular DNA of Porcine Retrovirus," Febs Letters, vol. 198, No. 2, 1986, pp 339–343.

Suzuka et al., "Some Characteristics of a Porcine Retrovirus From a Cell Line Derived From Swine Malignant Lymphomas," Febs Letters, vol. 183, 1985, pp 124–128.

Chen B–F et al., "Characterization of a Bicistronic Retroviral Vector Composed of the Swine Vesicular Disease Virus Internal Ribosome Entry Site," Journal of Virology, vol. 67, 1993, pp 2142–2148.

Phan–Thanh L. et al., "Porcine Retrovirus: Optimal Conditions for its Biochemical Detection," Archives of Virology, vol. 123, 1992, pp 255–265.

Teich, "RNA Tumor Viruses," Taxonomy of Retroviruses, 1985, pp 25–207.

Betts, "Pathogen–Free" Pigs For Research and the Practical Control of Pig Diseases, The Veterinary Record, 1961, vol. 79, No. 49, pp 1349–1356.

Betts et al., "The Production by Hysterectomy of Pathogen–Free, Colostrum–Deprived Pigs and the Foundation of a Minimal–Disease Herd," Veterinary Record, 1960, vol. 72, pp461–468.

Smith, "Endogenous Retroviruses in Xenografts," New England Journal of Medicine, vol. 328, pp. 142–143, 1993.

Chiche, "Xenotransplantation: Baboons as Potential Liver Donors," Transplantation, vol. 6, pp1418–1421, 1993.

Calne, "Organ Transplatation Between Widely Disparate Species," Transplantation Proceedings, vol. II, No. 4, 1970, pp 550–553.

Brede et al., "Bacteriological and Viological Considerations in Primate Transplants," Primates in Medicine, vol. 7, pp 18–28, 1972.

(List continued on next page.)

Primary Examiner—Jezia Riley
(74) Attorney, Agent, or Firm—Fish & Richardson P.C.

(57) ABSTRACT

Purified nucleic acid which can specifically hybridize with the sequence of swine retroviruses.

27 Claims, 34 Drawing Sheets

OTHER PUBLICATIONS

Rubin et al., "Antimicrobial Strategies in the Care of Organ Transplant Recipients," Antimicrobial Agents and Chemotherapy, Apr. 1993, pp 619–624.

Starzl et al., "Baboon–to–Human Liver Transplantation," The Lancet, 1993, vol. 341, pp 65–71.

Castro et al., "Persistent Infection of Baboons and Rhesus Monkeys With Different Strains of HIV–2," Virology, vol. 184, pp 219–226, 1991.

McClure et al., "HIV Infection of Primate Lymphocytes and Conservation of the CD4 Receptor," Nature, vol. 330, pp 487–489, 1987.

Caldwell et al., "Swine Repopulation II. Performance of "Disease–Free" Boars on Farms With Diseased Pigs," American Veterinary Medical Association, vol. 135, pp 504–505, 1959.

Beneviste et al., "Homology Between Type–C Viruses of Various Species as Determined by Molecular Hybridization," Proc. Nat. Acad. Sci, USA, vol. 70, No. 12, Part l, pp 3316–3320, 1973.

Metzger et al., "Transplantation in Miniature Swine," The Journal of Immunology, vol. 127, No. 2, 1981, pp769–775.

Letvin et al., "Infection of Baboons With Human Immunodeficiency Virus–2 (HIV–2)," The Journal of Infectious Diseases, vol. 156, No. 2, 1987, pp 406–407.

Van der Riet, "Virological Implications of the Use of Primates in Xenotransplantation," Transplant Proceedings, vol. XIX No. 5, 1987, pp 4068–4069.

Kalter, "The Nonhuman Primate as Potential Organ Donor For Man: Viological Considerations," Xenotransplantation: The Transplantation of Organs and Tissues Between Species, 1991, pp 457–479.

Auchincloss, Jr., "Xenogeneic Transplantation," Transplantation, 1988, vol. 46, pp 1–19.

Murphy et al., "The Cape Western Baboon in Organ Allotransplantation," Transplantation Proceedings, vol. II, No. 4, 1970, pp 546–549.

Niekrasz et al., "The Pig as Organ Donor for Man," Transplantation Proceedings, vol. 24, No. 2, pp 625–626, 1992.

Alexander et al., "Medicated Early Weaning: A Method of Breaking the Cycle of Endemic Infection," Proc. $6^{th}$ Int. Congr. Pig. Vet. See, Copenhagen.

Young, "SPF Swine," Adv. Vet. Sci, vol. 9, pp. 61–112.

Gerard et al., "DNA Encoding a Novel Reverse Transcriptase . . . " European Molecular Biology Laboratory, Database Accession No. AAQ91980, Apr. 11, 1995.

Moehring et al., "The Exogenous RD–114 and the Related Endogenous Proviral Element ECE1 of Domestic Cat . . . " European Molecular Biological Laboratory, Database Accession No. X51929, Apr. 2, 1990.

Aaronson et al., "Endogenous Type–C RNA Viruses of Mammalian Cells," Bio et Biophys. Acta 458:323–354 (1976).

Armstrong et al., "C–type virus particles in pig kidney cell lines," J. Gen. Virol. 10:195–198 (1971).

Benveniste et al., "Evolution of type C viral genes: preservation of ancestral murine type C viral sequences in pig cellular DNA" PNAS 72:4090–4094 (1975).

Benveniste et al., "Multiple divergent copies of endogenous C–type virogenes in mammalian cells," Nature 252:170–173 (1974).

Bouillant et al., "Multisequential transformation of a pig cell line (PFT): Correlations between tumorigenicity and chromosome and ultrastructural markers," JNCI 64(4):783–788 (1980).

Bouillant et al., "Nontumoral, benign and malignant stages of transformation of a diploid pig cell line. A Review," Can. J. Comp. Med. 45:279–290 (1981).

Bouillant et al., "Type C virus production by a continuous line of pig oviduct cells (PFT)," J. Gen. Virol. 27:173 (1975).

Bouillant et al., "Ultrastructural Comparison of Oncovirinae (type C), Spumavirinae, and Lentivirinae: three Subfamilies of Retroviridae Found in Farm Animals," J. Nat. Cancer Institute 72:1075 (1984).

Bowes, "Localization of a retroviral element within the rd gene coding the Beta Subunit of cGMP phosphodiesterase," PNAS USA 90:2955–2959.

Busse et al., "Further investigations on the porcine lymphoma C–type particle (PLCP) and the possible biological significance of the virus in pigs," Ann. Rech. Vet. 5(4):651–658 (1978).

Busse et al., "Partial analysis of the polypeptide composition of a porcine lymphoma C–type particle (PLCP)" Zbl. Vet. Med. B. 28:118–125 (1981).

D'Aquila, R.T., "HIV–1 chemotherapy and drug resistance," Clinical and Diagnostic Virology 3:299–316 (1995).

D'Aquila, R.T. et al., "Zidovudine Resistance and HIV–1 Disease Progression during Antiretroviral Therapy," Annals of Internal Medicine 122(6):401–408 (1995).

Delassus et al., "Genetic Organization of the Gibbon Ape Leukemia Virus," Virology 173:205–213 (1989).

Devare et al., "Nucleotide Sequence of the Simian Sarcoma Virus Genome: Demonstration that its Acquired Cellular Sequences Encode the Transforming Gene Product p28," PNAS USA 80:731–735 (1983).

Eron, J.J. et al., "Susceptibility testing by polymerase chain reaction DNA quantitation: A method to measure drug resistance of human immunodeficiency virus type 1 isolates," PNAS USA 89:3241–3245 (1992).

Fishman, J.A., "Miniature swine as organ donors for man: Strategies for prevention of xenotransplant–associated infections," Xenotransplantation 1:47–57 (1994).

Frazier, "Evidence for retrovirus in miniature swine with radiation–induced leukemia or metaplasia," Arch. of Virology 83:83–97 (1985).

Frazier et al., "Virus association with $^{90}$Sr Induced leukemia of miniature swine," Comparative Leukemia Res. 36:440–445 (1969).

Jarrett, "Evidence for the viral etiology of leukemia in the domestic mammals," Cancer Res. 13 (1970).

Kadota et al., "Ultrastructure and C–type particles in myeloid leukemia of a pig," Vet. Pathol. 21:263–265 (1984).

Kaeffer et al., "Histocompatible miniature pig (d/d haplo–type): generation of hybridomas secreting A or M monoclonal antibody," Hybridoma 10:731 (1991).

Kaeffer et al., "Immortal porcine lymphoblastoid cell lines: interest for veterinary and medical research," Vet. Res. 25:425 (1994).

Kaeffer et al., "Histocompatible miniature boar model: selection of transformed cell lines of B and T lineages producing retrovirus," Int. J. Cancer 46:481–488 (1990).

Kaeffer et al., "Epithelioid and fibroblastic cell lines derived form the ileum of an adult histocompatible miniature board (dd/d haplotype) and immortalized by SV40 plasmid," *Euro. J. of Cell Biology* 62:152–162(1993).

Lieber et al., "Biologic and immunologic properties of porcine Type C viruses," *Virolgy* 66:616 (1975).

Lieber et al., "Mammalian cells in culture frequently release type C viruses," *Science* 182:56–59 (1973).

Moennig et al., "C–type particles produced by a permanent cell line from a leukemic pig. II. Physical chemical, and serological characterization of the particles," *Virology* 57:179 (1974).

Petters et al., "Gene transfer in swine embryos by injection of cells infected with retrovirus vectors," *J. Exp. Zoology* 242:85–88 (1987).

Rhim et al., "Characterization of murine sarcoma virus transformation of guinea pig cells and activation of an RNA tumor–like virus from nonproducer guinea pig cells," *Bibl. Haematol.* 153–164 (1975).

Schafer et al., "Polypeptides of mammalian oncornaviruses. II Characterization of murine leukemia virus polypeptide (p15) bearing interspecies reactivity," *Virol.* 63:48–59 (1975).

Schafer et al., "Morphological, chemical, and antigenic organization of mammalian C–type viruses," *Bibl. Haematol.* 497–515 (1975).

Schafer et al., "Evidence for the existence of different antigenic determinants of the interspecies type in mammalian RNA–C–type viruses," (author's transl.)*Z Naturforsch* [C] 28:214–222 (1973).

Sherr et al, "Interspecies antigenic determinants of the reverse transcriptases and p30 proteins of mammalian Type C viruses," *J. Virol.* 15:1440 (1975).

Stoye, J.P. and J.M. Coffin, "The dangers of xenotransplantation," *Nature Medicine* 1(11):1100 (1995).

Strandstrom et al., "C–type particles produced by a permanent cell line from a leukemic pig," *Virology* 57:175–178.

Suzuki et al., "Production and characterization of monoclonal antibodies which affect RNA–dependent DNA polymerase activity of porcine retrovirus reverse transcriptase," *Jpn J Vet Sci* 50:295–297 (1988).

Takeyama et al., "Enhancement of fibroblast growth factor–induced diacylglycerol formation and protein kinase C activation by colon tumor–promoting bile acid in Swiss 3T3 cells," *FEBS* 3461 197:339–343 (1986).

Te Riele, H. et al., "Highly efficient gene targeting in embryonic stem cells through homologous recombination with isogenic DNA constructs," *PNAS USA* 89:5128–5132 (1992).

Todaro et al, "Characterization of a Type C virus released from the porcine cell line PK(15)," *Virology* 58:65 (1974).

Tumilowicz et al., "Concurrent replication of a papovirus and a C–type virus in the CCL 33 porcine cell line," *In Vitro* 15:922–928 (1979).

Young, "SPF Swine," *Adv. Vet. Sci.* vol. 9:61–112.

Woods et al., "Antigenic and biochemical characterization of the C–type particle of the stable porcine kidney cell line PK–15," *J. Virol.* 12:1184 (1973).

* cited by examiner

| | | |
|---|---|---|
| CTCGAGACTC GGTGGAAGGG CCCTTATCTC GTACTTTTGA CCACACCAAC | 50 | (SEQ ID NO: 1) |
| GGCTGTGAAA GTCGAAGGAA TCTCCACCTG GATCCATGCA TCCCACGTTA | 100 | |
| AGCCGGCGCC ACCTCCCGAT TCGGGGTGGA AAGCCGAAAA GACTGAAAAT | 150 | |
| CCCCTTAAGC TTCGCCTCCA TCGCGTGGTT CCTTACTCTG TCAATAACCT | 200 | |
| CTCAGACTAA TGGTATGCGC ATAGGAGACA GCCTGAACTC CCATAAACCC | 250 | |
| TTATCTCTCA CCTGGTTAAT TACTGACTCC GGCACAGGTA TTAATATCAA | 300 | |
| CAACACTCAA GGGGAGGCTC CTTTAGGAAC CTGGTGGCCT GATCTATACG | 350 | |
| TTTGCCTCAG ATCAGTTATT CCTAGTCTGA CCTCACCCCC AGATATCCTC | 400 | |
| CATGCTCACG GATTTTATGT TTGCCCAGGA CCACCAAATA ATGGAAAACA | 450 | |
| TTGCGGAAAT CCCAGAGATT TCTTTTGTAA ACAATGGAAC TGTGTAACCT | 500 | |
| CTAATGATGG ATATTGGAAA TGGCCAACCT CTCAGCAGGA TAGGGTAAGT | 550 | |
| TTTTCTTATG TCAACACCTA TACCAGCTCT GGACAATTTA ATTACCTGAC | 600 | |
| CTGGATTAGA ACTGGAAGCC CCAAGTGCTC TCCTTCAGAC CTAGATTACC | 650 | |
| TAAAAATAAG TTTCACTGAG AAAGGAAAAC AAGAAAATAT CCTAAAATGG | 700 | |
| GTAAATGGTA TGTCTTGGGG AATGGTATAT TATGGAGGCT CGGGTAAACA | 750 | |
| ACCAGGCTCC ATTCTAACTA TTCGCCTCAA AATAAACCAG CTGGAGCCTC | 800 | |
| CAATGGCTAT AGGACCAAAT ACGGTCTTGA CGGGTCAAAG ACCCCCAACC | 850 | |
| CAAGGACCAG GACCATCCTC TAACATAACT TCTGGATCAG ACCCCACTGA | 900 | |
| GTCTAGCAGC ACGACTAAAA TGGGGCAAA ACTTTTTAGC CTCATCCAGG | 950 | |
| GAGCTTTTCA AGCTCTTAAC TCCACGACTC CAGAGGCTAC CTCTTCTTGT | 1000 | |
| TGGCTATGCT TAGCTTTGGG CCCACCTTAC TATGAAGGAA TGGCTAGAAG | 1050 | |
| AGGGAAATTC AATGTGACAA AAGAACATAG AGACCAATGC ACATGGGGAT | 1100 | |
| CCCAAAATAA GCTTACCCTT ACTGAGGTTT CTGGAAAAGG CACCTGCATA | 1150 | |
| GGAAAGGTTC CCCCATCCCA CCAACACCTT TGTAACCACA CTGAAGCCTT | 1200 | |
| TAATCAAACC TCTGAAAGTC AATATCTGGT ACCTGGTTAT GACAGGTGGT | 1250 | |
| .GTAA TACTGGATTA ACCCCTTGTG TTTCCACCTT GGTTTTTAAC | 1300 | |

FIGURE 1

| | | |
|---|---|---|
| CAAACTAAAG ATTTTTGCAT TATGGTCCAA ATTGTTCCCC GAGTGTATTA | 1350 | (SEQ ID NO: 1) cont'd |
| CTATCCCGAA AAAGCAATCC TTGATGAATA TGACTACAGA AATCATCGAC | 1400 | |
| AAAAGAGAGA ACCCATATCT CTGACACTTG CTGTGATGCT CGGACTTGGA | 1450 | |
| GTGGCAGCAG GTGTAGGAAC AGGAACAGCT GCCCTGGTCA CGGGACCACA | 1500 | |
| GCAGCTAGAA ACAGGACTTA GTAACCTACA TCGAATTGTA ACAGAAGATC | 1550 | |
| TCCAAGCCCT AGAAAAATCT GTCAGTAACC TGGAGGAATC CCTAACCTCC | 1600 | |
| TTATCTGAAG TAGTCCTACA GAATAGAAGA GGGTTAGATT TATTATTTCT | 1650 | |
| AAAAGAAGGA GGATTATGTG TAGCCTTGAA GGAGGAATGC TGTTTTTATG | 1700 | |
| TGGATCATTC AGGGGCCATC AGAGACTCCA TGAACAAACT TAGAGAAAGG | 1750 | |
| TTGGAGAAGC GTCGAAGGGA AAAGGAAACT ACTCAAGGGT GGTTTGAGGG | 1800 | |
| ATGGTTCAAC AGGTCTCCTT GGTTGGCTAC CCTACTTTCT GCTTTAACAG | 1850 | |
| GACCCTTAAT AGTCCTCCTC CTGTTACTCA CAGTTGGGCC ATGTATTATT | 1900 | |
| AACAAGTTAA TTGCCTTCAT TAGAGAACGA ATAAGTGCAG TCCAGATCAT | 1950 | |
| GGTACTTAGA CAACAGTACC AAAGCCCGTC TAGCAGGGAA GCTGGCCGCT | 2000 | |
| AGCTCTACCA GTTCTAAGAT TAGAACTATT AACAAGAGAA GAAGTGGGGA | 2050 | |
| ATGAAAGGAT GAAAATACAA CCTAAGCTAA TGAGAAGCTT AAAATTGTTC | 2100 | |
| TGAATTCCAG AGTTTGTTCC TTATAGGTAA AAGATTAGGT TTTTTGCTGT | 2150 | |
| TTTAAAATAT GCGGAAGTAA AATAGGCCCT GAGTACATGT CTCTAGGCAT | 2200 | |
| GAAACTTCTT GAAACTATTT GAGATAACAA GAAAAGGGAG TTTCTAACTG | 2250 | |
| CTTGTTTAGC TTCTGTAAAA CTGGTTGCGC CATAAAGATG TTGAAATGTT | 2300 | |
| GATACACATA TCTTGGTGAC AACATGTCTC CCCCACCCCG AAACATGCGC | 2350 | |
| AAATGTGTAA CTCTAAAACA ATTTAAATTA ATTGGTCCAC GAAGCGCGGG | 2400 | |
| CTCTCGAAGT TTTAAATTGA CTGGTTTGTG ATATTTTGAA ATGATTGGTT | 2450 | |
| TGTAAAGCGC GGGCTTTGCT GTGAACCCCA TAAAAGCTGT CCCGACTCCA | 2500 | |
| CACTCGGGGC CGCAGTCCTC TACCCCTGCG TGGTGTACGA CTGTGGGCCC | 2550 | |

FIGURE 1, CONT.

```
CAGCGCGCTT GGAATAAAAA TCCTCTTGCT GTTTGCATCA AGACCGCTTC    2600    (SEQ ID NO: 1) cont'd
TCGTGAGTGA TTAAGGGGAG TCGCCTTTTC CGAGCCTGGA GGTTCTTTTT    2650
GCTGGTCTTA CATTTGGGGG CTCGTCCGGG ATCTGTCGCG GCCACCCCTA    2700
ACACCCGAGA ACCGACTTGG AGGTAAAAAG GATCCTCTTT TTAACGTGTA    2750
TGCATGTACC GGCCGGCGTC TCTGTTCTGA GTGTCTGTTT TCAGTGGTGC    2800
GCGCTTTCGG TTTGCAGCTG TCCTCTCAGG CCGTAAGGGC TGGGGACTG     2850
TGATCAGCAG ACGTGCTAGG AGGATCACAG GCTGCTGCCC TGGGGACGC     2900
CCCGGGAGGT GAGGAGAGCC AGGGACGCCT GGTGGTCTCC TACTGTCGGT    2950
CAGAGGACCG AATTCTGTTG CTGAAGCGAA AGCTTCCCCC TCCGCGACCG    3000
TCCGACTCTT TTGCCTGCTT GTGGAATACG TGGACGGGTC ACGTGTGTCT    3050
GGATCTGTTG GTTTCTGTTT TGTGTGTCTT TGTCTTGTGT GTCCTTGTCT    3100
ACAGTTTTAA TATGGGACAG ACGGTGACGA CCCCTCTTAG TTTGACTCTC    3150
GACCATTGGA CTGAAGTTAA ATCCAGGGCT CATAATTTGT CAGTTCAGGT    3200
TAAGAAGGGA CCTTGGCAGA CTTTCTGTGT CTCTGAATGG CCGACATTCG    3250
ATGTTGGATG GCCATCAGAG GGGACCTTTA ATTCTGAGAT TATCCTGGCT    3300
GTTAAAGCAA TTATTTTTCA GACTGGACCC GGCTCTCATC CCGATCAGGA    3350
GCCCTATATC CTTACGTGGC AAGATTTGGC AGAGGATCCT CCGCCATGGG    3400
TTAAACCATG GCTGAATAAG CCAAGAAAGC CAGGTCCCCG AATTCTGGCT    3450
CTTGGAGAGA AAAACAAACA CTCGGCTGAA AAAGTCAAGC CCTCTCCTCA    3500
TATCTACCCC GAGATTGAGG AACCACCGGC TTGGCCGGAA CCCCAATCTG    3550
TTCCCCCACC CCCTTATCTG GCACAGGGTG CCGCGAGGGG ACCCTTTGCC    3600
CCTCCTGGAG CTCCGGCGGT GGAGGGACCT TCTGCAGGGA CTCGGAGCCG    3650
GAGGGCGCC ACCCCGGAGC GGACAGACGA GATCGCGACA TTACCGCTGC     3700
GCACGTACGG CCCTCCCACA CCGGGGGCC AATTGCAGCC CCTCCAGTAT      3750
TGGCCCTTTT CTTCTGCAGA TCTCTATAAT TGGAAAACTA ACCATCCCCC    3800
```

FIGURE 1, CONT.

| | |
|---|---|
| TTTCTCGGAG GATCCCCAAC GCCTCACGGG GTTGGTGGAG TCCCTTATGT | 3850 (SEQ ID NO: 1) cont'd |
| TCTCTCACCA GCCTACTTGG GATGATTGTC AACAGCTGCT GCAGACACTC | 3900 |
| TTCACAACCG AGGAGCGAGA GAGAATTCTA TTAGAGGCTA GAAAAAATGT | 3950 |
| TCCTGGGGCC GACGGGCGAC CCACGCGGTT GCAAAATGAG ATTGACATGG | 4000 |
| GATTTCCCTT AACTCGCCCC GGTTGGGACT ACAACACGGC TGAAGGTAGG | 4050 |
| GAGAGCTTGA AAATCTATCG CCAGGCTCTG GTGGCGGGTC TCCGGGCGC | 4100 |
| CTCAAGACGG CCCACTAATT TGGCTAAGGT AAGAGAAGTG ATGCAGGGAC | 4150 |
| CGAATGAACC CCCCTCTGTT TTTCTTGAGA GGCTCTTGGA AGCCTTCAGG | 4200 |
| CGGTACACCC CTTTTGATCC CACCTCAGAG GCCCAAAAAG CCTCAGTGGC | 4250 |
| TTTGGCCTTT ATAGGACAGT CAGCCTTGGA TATTAGAAAG AAGCTTCAGA | 4300 |
| GACTGGAAGG GTTACAGGAG GCTGAGTTAC GTGATCTAGT GAAGGAGGCA | 4350 |
| GAGAAAGTAT ATTACAAAAG GGAGACAGAA GAAGAAAGGG AACAAAGAAA | 4400 |
| AGAGAGAGAA AGAGAGGAAA GGGAGGAAAG ACGTAATAAA CGGCAAGAGA | 4450 |
| AGAATTTGAC TAAGATCTTG GCTGCAGTGG TTGAAGGGAA AAGCAATACG | 4500 |
| GAAAGAGAGA GAGATTTTAG GAAAATTAGG TCAGGCCCTA GACAGTCAGG | 4550 |
| GAACCTGGGC AATAGGACCC CACTCGACAA GGACCAATGT GCATATTGTA | 4600 |
| AAGAAAGAGG ACACTGGGCA AGGAACTGCC CCAAGAAGGG AAACAAAGGA | 4650 |
| CCAAGGATCC TAGCTCTAGA AGAAGATAAA GATTAGGGGA GACGGGGTTC | 4700 |
| GGACCCCCTC CCCGAGCCCA GGGTAACTTT GAAGGTGGAG GGGCAACCAG | 4750 |
| TTGAGTTCCT GGTTGATACC GGAGCGAAAC ATTCAGTGCT ACTACAGCCA | 4800 |
| TTAGGAAAAC TAAAAGATAA AAAATCCTGG GTGATGGGTG CACAGGGCAA | 4850 |
| CAACAGTATC CATGGACTAC CCGAAGACAG TTGACTTGGG AGTGGGACGG | 4900 |
| GTAACCCACT CGTTTCTGGT CATACCTGAG TGCCCAGCAC CCCTCTTAGG | 4950 |
| TAGAGACTTA TTGACCAAGA TGGGAGCACA AATTTCTTTT GAACAAGGGA | 5000 |
| AACCAGAAGT GTCTGCAAAT AACAAACCTA TCACTGTGTT GACCCTCCAA | 5050 |

FIGURE 1, CONT.

| | | | | | |
|---|---|---|---|---|---|
| TTAGATGACG | AATATCGACT | ATACTCTCCC | CTAGTAAAGC | CTGATCAAAA | 5100 |
| TATACAATTC | TGGTTGGAAC | AGTTTCCCCA | AGCCTGGGCA | GAAACCGCAG | 5150 |
| GGATGGGTTT | GGCAAAGCAA | GTTCCCCCAC | AAGTTATTCA | ACTGAAGGCC | 5200 |
| AGTGCCACAC | CAGTGTCAGT | CAGACAGTAC | CCCTTGAGTA | AAGAAGCTCA | 5250 |
| AGAAGGAATT | CGGCCGCATG | TCCAAAGATT | AATCCAACAG | GCATCCTAG | 5300 |
| TTCCTGTCCA | ATCTCCCTGG | AATACTCCCC | TGCTACCGGT | TAGAAAGCCT | 5350 |
| GGGACTAATG | ACTATCGACC | AGTACAGGAC | TTGAGAGAGG | TCAATAAACG | 5400 |
| GGTGCAGGAT | ATACACCCAA | CAGTCCCGAA | CCCTTATAAC | CTCTTGTGTG | 5450 |
| CTCTCCCACC | CCAACGGAGC | TGGTATACAG | TATTGGACTT | AAAGGATGCC | 5500 |
| TTCTTCTGCC | TGAGATTACA | CCCCACTAGC | CAACCACTTT | TTGCCTTCGA | 5550 |
| ATGGAGAGAT | CCAGGTACGG | GAAGAACCGG | GCAGCTCACC | TGGACCCGAC | 5600 |
| TGCCCCAAGG | GTTCAAGAAC | TCCCCGACCA | TCTTTGACGA | AGCCCTACAC | 5650 |
| AGAGACCTGG | CCAACTTCAG | GATCCAACAC | CCTCAGGTGA | CCCTCCTCCA | 5700 |
| GTACGTGGAT | GACCTGCTTC | TGGCGGGAGC | CACCAAACAG | GACTGCTTAG | 5750 |
| AAGGCACGAA | GGCACTACTG | CTGGAATTGT | CTGACCTAGG | CTACAGAGCC | 5800 |
| TCTGCTAAGA | AGGCCCAGAT | TTGCAGGAGA | GAGGTAACAT | ACTTGGGGTA | 5850 |
| CAGTTTACGG | GACGGGCAGC | GATGGCTGAC | GGAGGCACGG | AAGAAAACTG | 5900 |
| TAGTCCAGAT | ACCGGCCCCA | ACCACAGCCA | AACAAATGAG | AGAGTTTTTG | 5950 |
| GGGACAGCTG | GATTTTGCAG | ACTGTGGATC | CCGGGGTTTG | CGACCTTAGC | 6000 |
| AGCCCCACTC | TACCCGCTAA | CCAAAGAAAA | AGGGGAATTC | TCCTGGGCTC | 6050 |
| CTGAGCACCA | GAAGGCATTT | GATGCTATCA | AAAAGGCCCT | GCTGAGCGCA | 6100 |
| CCTGCTCTGG | CCCTCCCTGA | CGTAACTAAA | CCCTTTACCC | TTTATGTGGA | 6150 |
| TGAGCGTAAG | GGAGTAGCCC | GGGGAGTTTT | AACCCAAACC | CTAGGACCAT | 6200 |
| GGAGAAGACC | TGTCGCCTAC | CTGTCAAAGA | AGCTCGATCC | TGTAGCCAGT | 6250 |
| GGTTGGCCCA | TATGCCTGAA | GGCTATCGCA | GCTGTGGCCA | TACTGGTCAA | 6300 |

FIGURE 1, CONT.

```
GGACGCTGAC AAATTGACTT TGGGACAAGA ATATAACTGT AATAGCCCCC    6350    (SEQ ID NO: 1) cont'd
CATGCATTGG AGAACATCGT TCGGCAGCCC CCAGACCGAT GGATGACCAA    6400
CGCCCGCATG ACCCACTATC AAAGCCTGCT TCTCACAGAG AGGGTCACGT    6450
TCGCTCCACC AACCGCTCTC AACCCTGCCA CTCTTCTGCC TGAAGAGACT    6500
GATGAACCAG TGACTCATGA TTGCCATCAA CTATTGATTG AGGAGACTGG    6550
GGTCCGCAAG GACCTTACAG ACATACCGCT GACTGGAGAA GTGCTAACCT    6600
GGTTCACTGA CGGAAGCAGC TATGTGGTGG AAGGTAAGAG GATGGCTGGG    6650
GCGGCGGTGG TGGACGGGAC CCGCACGATC TGGGCCAGCA GCCTGCCGGG    6700
AGGAACTTCA GCACAAAAGG CTGAGCTCAT GGCCCTCACG CAAGCTTTGC    6750
GGCTGGCCGA AGGGAAATCC ATAAACATTT ATACGGACAG CAGGTATGCC    6800
TTTGCGACTG CACACGTACA TGGGGCCATC TATAAACAAA GGGGGTTGCT    6850
TACCTCAGCA GGGAGGGAAA TAAAGAACAA AGAGGAAATT CTAAGCCTAT    6900
TAGAAGCCGT ACATTTACCA AAAAGGCTAG CTATTATACA CTGTCCTGGA    6950
CATCAGAAAG CTAAAGATCT CATATCCAGA GGAAACCAGA TGGCTGACCG    7000
GGTTGCCAAG CAGGCAGCCC AGGGTGTTAA CCTTCTGCCT ATAATAGAAA    7050
TGCCCAAAGC CCCAGAACCC AGACGACAGT ACACCCTAGA AGACTGGCAA    7100
GAGATAAAAA AGATAGACCA TTCTCTGAGA CTCCGGAAGG GACCTGCTAT    7150
ACCTCAGATG GGAAGGAAAT CCTGCCCCAC AAAGAAGGGT TAGAATATGT    7200
CCAACAAGAT ACATCGTCTA ACCCACCTAG GAACTAAACA CCTGCAGCAG    7250
TTGGTCAGAA CATCCCCTTA TCATGTTCTG AGGCTACCAG GAGTGGCTGA    7300
CTCGGTGGTC AAACATTGTG TGCCCTGCCA GCTGGTTAAT GCTAATCCTT    7350
CCAGAATGCC TCCAGGGAAG AGACTAAGGG GAAGCCACCC AGGCGCTCAC    7400
TGGGAAGTGG ACTTCACTGA GGTAAAGCCG GCTAAATATG GAAACAAATA    7450
CCTATTGGTT TTTGTAGACA CCTTTTCAGG ATGGGTAGAG GCTTATCCTA    7500
CTAAGAAAGA GACTTCAACC GTGGTAGCTA AAAAAATACT GGAAGAAATT    7550
```

FIGURE 1, CONT.

| | | |
|---|---|---|
| TTTCCAAGAT TTGGAATACC TAAGGTAATA GGGTCAGACA ATGGTCCAGC | 7600 | (SEQ ID NO: 1) cont'd |
| TTTTGTTGCC CAGGTAAGTC AGGGACTGGC CAAGATATTG GGGATTGATT | 7650 | |
| GGAAACTGCA TTGTGCATAC AGACCCCAAA GCTCAGGACA GGTAGAGAGG | 7700 | |
| ATGAATAGAA CCATTAAAGA GACCCTTACT AAATTGACCG CGGAGACTGG | 7750 | |
| CGTTAATGAT TGGATAGCTC TCCTGCCCTT TGTGCTTTTT AGGGTTAGGA | 7800 | |
| ACACCCCTGG ACAGTTTGGG CTGACCCCCT ATGAATTACT CTACGGGGA | 7850 | |
| CCCCCCCCAT TGGTAGAAAT TGCTTCTGTA CATAGTGCTG ATGTGCTGCT | 7900 | |
| TTCCAGCCT TTGTTCTCTA GGCTCAAGGC ACTTGAGTGG GTGAGACAAC | 7950 | |
| GAGCGTGGAG GCAACTCCGG GAGGCCTACT CAGGAGGAGG AGACTTGCAG | 8000 | |
| ATCCCACATC GTTTCCAAGT GGGAGATTCA GTCTACGTTA GACGCCACCG | 8050 | |
| TGCAGGAAAC | 8060 | |

FIGURE 1, CONT.

```
            10         20         30         40         50         60       (SEQ ID NO: 2)
    *     *     *     *     *     *     *     *     *     *     *     *
CTACCCCTGC GTGGTGTACG ACTGTGGGCC CCAGCGCGCT TGGAATAAAA ATCCTCTTGC 70         80         90        100        110        120
    *     *     *     *     *     *     *     *     *     *     *     *
TGTTTGCATC AAGACCGCTT CTTGTGAGTG ATTTGGGGTG TCGCCTCTTC CGAGCCCGGA 130        140        150        160        170        180
    *     *     *     *     *     *     *     *     *     *     *     *
CGAGGGGGAT TGTTCTTTTA CTGGCCTTTC ATTTGGTGCG TTGGCCGGGA AATCCTGCGA 190        200        210        220        230        240
    *     *     *     *     *     *     *     *     *     *     *     *
CCACCCCTTA CACCCGAGAA CCGACTTGGA GGTAAAGGGA TCCCCTTTGG AACATATGTG 250        260        270        280        290        300
    *     *     *     *     *     *     *     *     *     *     *     *
TGTGTCGGCC GGCGTCTCTG TTCTGAGTGT CTGTTTTCGG TGATGCGCGC TTTCGGTTTG 310        320        330        340        350        360
    *     *     *     *     *     *     *     *     *     *     *     *
CAGCTGTCCT CTCAGACCGT AAGGACTGGA GGACTGTGAT CAGCAGACGT GCTAGGAGGA 370        380        390        400        410        420
    *     *     *     *     *     *     *     *     *     *     *     *
TCACAGGCTG CCACCCTGGG GGACGCCCCG GGAGGTGGGG AGAGCCAGGG ACGCCTGGTG 430        440        450        460        470        480
    *     *     *     *     *     *     *     *     *     *     *     *
GTCTCCTACT GTCGGTCAGA GGACCGAGTT CTGTTGTTGA AGCGAAAGCT TCCCCCTCCG 490        500        510        520        530        540
    *     *     *     *     *     *     *     *     *     *     *     *
CGGCCGTCCG ACTCTTTTGC CTGCTTGTGG AAGACGCGGA CGGGTCGCGT GTGTCTGGAT 550        560        570        580        590        600
    *     *     *     *     *     *     *     *     *     *     *     *
CTGTTGGTTT CTGTTTCGTG TGTCTTTGTC TTGTGCGTCC TTGTCTACAG TTTTAAT ATG
                                                                Met>

610        620        630        640
    *     *     *     *     *     *     *     *     *
GGA CAG ACA GTG ACT ACC CCC CTT AGT TTG ACT CTC GAC CAT TGG ACT
Gly Gln Thr Val Thr Thr Pro Leu Ser Leu Thr Leu Asp His Trp Thr>

650        660        670        680        690
    *     *     *     *     *     *     *     *     *     *
GAA GTT AGA TCC AGG GCT CAT AAT TTG TCA GTT CAG GTT AAG AAG GGA
Glu Val Arg Ser Arg Ala His Asn Leu Ser Val Gln Val Lys Lys Gly>

700        710        720        730        740
    *     *     *     *     *     *     *     *     *
CCT TGG CAG ACT TTC TGT GCC TCT GAA TGG CCA ACA TTC GAT GTT GGA
Pro Trp Gln Thr Phe Cys Ala Ser Glu Trp Pro Thr Phe Asp Val Gly>
```

FIGURE 2

(SEQ ID NO: 2) cont'd

```
         750          760          770          780          790
    *      *      *      *      *      *      *      *      *      *
   TGG    CCA    TCA    GAG    GGG    ACC    TTT    AAT    TCT    GAA    ATT    ATC    CTG    GCT    GTT    AAG
   Trp    Pro    Ser    Glu    Gly    Thr    Phe    Asn    Ser    Glu    Ile    Ile    Leu    Ala    Val    Lys>

800          810          820          830          840
    *      *      *      *      *      *      *      *      *      *
   GCA    ATC    ATT    TTT    CAG    ACT    GGA    CCC    GGC    TCT    CAT    CCT    GAT    CAG    GAG    CCC
   Ala    Ile    Ile    Phe    Gln    Thr    Gly    Pro    Gly    Ser    His    Pro    Asp    Gln    Glu    Pro>

850          860          870          880
    *      *      *      *      *      *      *      *      *
   TAT    ATC    CTT    ACG    TGG    CAA    GAT    TTG    GCA    GAA    GAT    CCT    CCG    CCA    TGG    GTT
   Tyr    Ile    Leu    Thr    Trp    Gln    Asp    Leu    Ala    Glu    Asp    Pro    Pro    Pro    Trp    Val>

890          900          910          920          930
    *      *      *      *      *      *      *      *      *      *
   AAA    CCA    TGG    CTA    AAT    AAA    CCA    AGA    AAG    CCA    GGT    CCC    CGA    ATC    CTG    GCT
   Lys    Pro    Trp    Leu    Asn    Lys    Pro    Arg    Lys    Pro    Gly    Pro    Arg    Ile    Leu    Ala>

940          950          960          970          980
    *      *      *      *      *      *      *      *      *
   CTT    GGA    GAG    AAA    AAC    AAA    CAC    TCG    GCC    GAA    AAA    GTC    GAG    CCC    TCT    CCT
   Leu    Gly    Glu    Lys    Asn    Lys    His    Ser    Ala    Glu    Lys    Val    Glu    Pro    Ser    Pro>

990          1000         1010         1020         1030
    *      *      *      *      *      *      *      *      *      *
   CGT    ATC    TAC    CCC    GAG    ATC    GAG    GAG    CCG    CCG    ACT    TGG    CCG    GAA    CCC    CAA
   Arg    Ile    Tyr    Pro    Glu    Ile    Glu    Glu    Pro    Pro    Thr    Trp    Pro    Glu    Pro    Gln>

1040         1050         1060         1070         1080
    *      *      *      *      *      *      *      *      *      *
   CCT    GTT    CCC    CCA    CCC    CCT    TAT    CCA    GCA    CAG    GGT    GCT    GTG    AGG    GGA    CCC
   Pro    Val    Pro    Pro    Pro    Pro    Tyr    Pro    Ala    Gln    Gly    Ala    Val    Arg    Gly    Pro>

1090         1100         1110         1120
    *      *      *      *      *      *      *      *      *      *
   TCT    GCC    CCT    CCT    GGA    GCT    CCG    GTG    GTG    GAG    GGA    CCT    GCT    GCC    GGG    ACT
   Ser    Ala    Pro    Pro    Gly    Ala    Pro    Val    Val    Glu    Gly    Pro    Ala    Ala    Gly    Thr>

1130         1140         1150         1160         1170
    *      *      *      *      *      *      *      *      *      *
   CGG    AGC    CGG    AGA    GGC    GCC    ACC    CCG    GAG    CGG    ACA    GAC    GAG    ATC    GCG    ATA
   Arg    Ser    Arg    Arg    Gly    Ala    Thr    Pro    Glu    Arg    Thr    Asp    Glu    Ile    Ala    Ile>

1180         1190         1200         1210         1220
    *      *      *      *      *      *      *      *      *
   TTA    CCG    CTG    CGC    ACC    TAT    GGC    CCT    CCC    ATG    CCA    GGG    GGC    CAA    TTG    CAG
   Leu    Pro    Leu    Arg    Thr    Tyr    Gly    Pro    Pro    Met    Pro    Gly    Gly    Gln    Leu    Gln>

1230         1240         1250         1260         1270
    *      *      *      *      *      *      *      *      *      *
   CCC    CTC    CAG    TAT    TGG    CCC    TTT    TCT    TCT    GCA    GAT    CTC    TAT    AAT    TGG    AAA
   Pro    Leu    Gln    Tyr    Trp    Pro    Phe    Ser    Ser    Ala    Asp    Leu    Tyr    Asn    Trp    Lys>

1280         1290         1300         1310         1320
    *      *      *      *      *      *      *      *      *      *
   ACT    AAC    CAT    CCC    CCT    TTC    TCG    GAG    GAT    CCC    CAA    CGC    CTC    ACG    GGG    TTG
   Thr    Asn    His    Pro    Pro    Phe    Ser    Glu    Asp    Pro    Gln    Arg    Leu    Thr    Gly    Leu>
```

FIGURE 2, CONT.

(SEQ ID NO: 2) cont'd

```
            1330        1340        1350        1360
             *     *     *     *     *     *     *     *     *
        GTG GAG TCC CTT ATG TTC TCT CAC CAG CCT ACT TGG GAT GAT TGT CAA
        Val Glu Ser Leu Met Phe Ser His Gln Pro Thr Trp Asp Asp Cys Gln>

1370        1380        1390        1400        1410
   *     *     *     *     *     *     *     *     *     *
 CAG CTG CTG CAG ACA CTC TTC ACA ACC GAG GAG CGA GAG AGA ATT CTG
 Gln Leu Leu Gln Thr Leu Phe Thr Thr Glu Glu Arg Glu Arg Ile Leu>

1420        1430        1440        1450        1460
             *     *     *     *     *     *     *     *     *
        TTA GAG GCT AAA AAA AAT GTT CCT GGG GCC GAC GGG CGA CCC ACG CAG
        Leu Glu Ala Lys Lys Asn Val Pro Gly Ala Asp Gly Arg Pro Thr Gln>

1470        1480        1490        1500        1510
             *     *     *     *     *     *     *     *     *     *
        TTG CAA AAT GAG ATT GAC ATG GGA TTT CCC TTG ACT CGC CCC GGT TGG
        Leu Gln Asn Glu Ile Asp Met Gly Phe Pro Leu Thr Arg Pro Gly Trp>

1520        1530        1540        1550        1560
             *     *     *     *     *     *     *     *     *     *
        GAC TAC AAC ACG GCT GAA GGT AGG GAG AGC TTG AAA ATC TAT CGC CAG
        Asp Tyr Asn Thr Ala Glu Gly Arg Glu Ser Leu Lys Ile Tyr Arg Gln>

1570        1580        1590        1600
             *     *     *     *     *     *     *     *     *
        GCT CTG GTG GCG GGT CTC CGG GGC GCC TCA AGA CGG CCC ACT AAT TTG
        Ala Leu Val Ala Gly Leu Arg Gly Ala Ser Arg Arg Pro Thr Asn Leu>

1610        1620        1630        1640        1650
   *     *     *     *     *     *     *     *     *     *
 GCT AAG GTA AGA GAG GTG ATG CAG GGA CCG AAC GAA CCT CCC TCG GTA
 Ala Lys Val Arg Glu Val Met Gln Gly Pro Asn Glu Pro Pro Ser Val>

1660        1670        1680        1690        1700
             *     *     *     *     *     *     *     *     *     *
        TTT CTT GAG AGG CTC ATG GAA GCC TTC AGG CGG TTC ACC CCT TTT GAT
        Phe Leu Glu Arg Leu Met Glu Ala Phe Arg Arg Phe Thr Pro Phe Asp>

1710        1720        1730        1740        1750
             *     *     *     *     *     *     *     *     *     *
        CCT ACC TCA GAG GCC CAG AAA GCC TCA GTG GCC CTG GCC TTC ATT GGG
        Pro Thr Ser Glu Ala Gln Lys Ala Ser Val Ala Leu Ala Phe Ile Gly>

1760        1770        1780        1790        1800
             *     *     *     *     *     *     *     *     *     *
        CAG TCG GCT CTG GAT ATC AGG AAG AAA CTT CAG AGA CTG GAA GGG TTA
        Gln Ser Ala Leu Asp Ile Arg Lys Lys Leu Gln Arg Leu Glu Gly Leu>

1810        1820        1830        1840
             *     *     *     *     *     *     *     *     *
        CAG GAG GCT GAG TTA CGT GAT CTA GTG AGA GAG GCA GAG AAG GTG TAT
        Gln Glu Ala Glu Leu Arg Asp Leu Val Arg Glu Ala Glu Lys Val Tyr>

1850        1860        1870        1880        1890
   *     *     *     *     *     *     *     *     *     *
 TAC AGA AGG GAG ACA GAA GAG GAG AAG GAA CAG AGA AAA GAA AAG GAG
 Tyr Arg Arg Glu Thr Glu Glu Glu Lys Glu Gln Arg Lys Glu Lys Glu>
```

FIGURE 2, CONT.

(SEQ ID NO: 2) cont'd

```
        1900        1910        1920        1930        1940
          *           *           *           *           *
      AGA GAA GAA AGG GAG GAA AGA CGT GAT AGA CGG CAA GAG AAG AAT TTG
      Arg Glu Glu Arg Glu Glu Arg Arg Asp Arg Arg Gln Glu Lys Asn Leu>

1950        1960        1970        1980        1990
            *           *           *           *           *
      ACT AAG ATC TTG GCC GCA GTG GTT GAA GGG AAG AGC AGC AGG GAG AGA
      Thr Lys Ile Leu Ala Ala Val Val Glu Gly Lys Ser Ser Arg Glu Arg>

2000        2010        2020        2030        2040
                *           *           *           *           *
      GAG AGA GAT TTT AGG AAA ATT AGG TCA GCC CCT AGA CAG TCA GGG AAC
      Glu Arg Asp Phe Arg Lys Ile Arg Ser Gly Pro Arg Gln Ser Gly Asn>

2050        2060        2070        2080
                   *           *           *           *
      CTG GGC AAT AGG ACC CCA CTC GAC AAG GAC CAG TGT GCG TAT TGT AAA
      Leu Gly Asn Arg Thr Pro Leu Asp Lys Asp Gln Cys Ala Tyr Cys Lys>

2090        2100        2110        2120        2130
      *           *           *           *           *
      GAA AAA GGA CAC TGG GCA AGG AAC TGC CCC AAG AAG GGA AAC AAA GGA
      Glu Lys Gly His Trp Ala Arg Asn Cys Pro Lys Lys Gly Asn Lys Gly>

2140        2150        2160        2170        2180
             *           *           *           *           *
      CCG AAG GTC CTA GCT CTA GAA GAA GAT AAA GAT T AGGGGAGACG
      Pro Lys Val Leu Ala Leu Glu Glu Asp Lys Asp>

2190        2200        2210        2220        2230        2240
                *           *           *           *           *           *
      GGGTTCGGAC CCCCTCCCCG AGCCCAGGGT AACTTTGAAG GTGGAGGGGC AACCAGTTGA 2250        2260        2270        2280        2290        2300
                *           *           *           *           *           *
      GTTCCTGGTT GATACCGGAG CGGAGCATTC AGTGCTGCTA CAACCATTAG GAAAACTAAA 2310        2320        2330        2340        2350
                *           *           *           *           *
      AGAAAAAAAA TCCTGGGTG ATG GGT GCC ACA GGG CAA CGG CAG TAT CCA TGG
                           Met Gly Ala Thr Gly Gln Arg Gln Tyr Pro Trp>

2360        2370        2380        2390        2400
             *           *           *           *           *
      ACT ACC CGA AGA ACC GTT GAC TTG GGA GTG GGA CGG GTA ACC CAC TCG
      Thr Thr Arg Arg Thr Val Asp Leu Gly Val Gly Arg Val Thr His Ser>

2410        2420        2430        2440
                *           *           *           *
      TTT CTG GTC ATC CCT GAG TGC CCA GTA CCC CTT CTA GGT AGA GAC TTA
      Phe Leu Val Ile Pro Glu Cys Pro Val Pro Leu Leu Gly Arg Asp Leu>

2450        2460        2470        2480        2490
      *           *           *           *           *
      CTG ACC AAG ATG GGA GCT CAA ATT TCT TTT GAA CAA GGA AGA CCA GAA
      Leu Thr Lys Met Gly Ala Gln Ile Ser Phe Glu Gln Gly Arg Pro Glu>
```

FIGURE 2, CONT.

(SEQ ID NO: 2) cont'd

```
          2500        2510        2520        2530        2540
            *           *           *           *           *
         GTG TCT GTG AAT AAC AAA CCC ATC ACT GTG TTG ACC CTC CAA TTA GAT
         Val Ser Val Asn Asn Lys Pro Ile Thr Val Leu Thr Leu Gln Leu Asp>

2550        2560        2570        2580        2590
                    *           *           *           *           *
         GAT GAA TAT CGA CTA TAT TCT CCC CAA GTA AAG CCT GAT CAA GAT ATA
         Asp Glu Tyr Arg Leu Tyr Ser Pro Gln Val Lys Pro Asp Gln Asp Ile>

2600        2610        2620        2630        2640
                    *           *           *           *           *
         CAG TCC TGG TTG GAG CAG TTT CCC CAA GCC TGG GCA GAA ACC GCA GGG
         Gln Ser Trp Leu Glu Gln Phe Pro Gln Ala Trp Ala Glu Thr Ala Gly>

2650        2660        2670        2680
                         *           *           *           *
         ATG GGT TTG GCA AAG CAA GTT CCC CCA CAG GTT ATT CAA CTG AAG GCC
         Met Gly Leu Ala Lys Gln Val Pro Pro Gln Val Ile Gln Leu Lys Ala>

2690        2700        2710        2720        2730
      *           *           *           *           *
         AGT GCT ACA CCA GTA TCA GTC AGA CAG TAC CCC TTG AGT AGA GAG GCT
         Ser Ala Thr Pro Val Ser Val Arg Gln Tyr Pro Leu Ser Arg Glu Ala>

2740        2750        2760        2770        2780
           *           *           *           *           *
         CGA GAA GGA ATT TGG CCG CAT GTT CAA AGA TTA ATC CAA CAG GGC ATC
         Arg Glu Gly Ile Trp Pro His Val Gln Arg Leu Ile Gln Gln Gly Ile>

2790        2800        2810        2820        2830
                *           *           *           *           *
         CTA GTT CCT GTC CAA TCC CCT TGG AAT ACT CCC CTA CCG GTT AGG
         Leu Val Pro Val Gln Ser Pro Trp Asn Thr Pro Leu Leu Pro Val Arg>

2840        2850        2860        2870        2880
                    *           *           *           *           *
         AAG CCT GGG ACC AAT GAT TAT CGA CCA GTA CAG GAC TTG AGA GAG GTC
         Lys Pro Gly Thr Asn Asp Tyr Arg Pro Val Gln Asp Leu Arg Glu Val>

2890        2900        2910        2920
                         *           *           *           *
         AAT AAA AGG GTG CAG GAC ATA CAC CCA ACG GTC CCG AAC CCT TAT AAC
         Asn Lys Arg Val Gln Asp Ile His Pro Thr Val Pro Asn Pro Tyr Asn>

2930        2940        2950        2960        2970
      *           *           *           *           *
         CTC TTG AGC GCC CTC CCG CCT GAA CGG AAC TGG TAC ACA GTA TTG GAC
         Leu Leu Ser Ala Leu Pro Pro Glu Arg Asn Trp Tyr Thr Val Leu Asp>

2980        2990        3000        3010        3020
           *           *           *           *           *
         TTA AAA GAT GCC TTC TTC TGC CTG AGA TTA CAC CCC ACT AGC CAA CCA
         Leu Lys Asp Ala Phe Phe Cys Leu Arg Leu His Pro Thr Ser Gln Pro>

3030        3040        3050        3060        3070
                *           *           *           *           *
         CTT TTT ACC TTC GAA TGG AGA GAT CCA GGT ACG GGA AGA ACC GGG CAG
         Leu Phe Thr Phe Glu Trp Arg Asp Pro Gly Thr Gly Arg Thr Gly Gln>
```

FIGURE 2, CONT.

(SEQ ID NO: 2) cont'd

```
          3080        3090        3100        3110        3120
            *    *      *    *      *    *      *    *      *    *
          CTC  ACC  TGG  ACC  CGA  CTG  CCC  CAA  GGG  TTC  AAG  AAC  TCC  CCG  ACC  ATC
          Leu  Thr  Trp  Thr  Arg  Leu  Pro  Gln  Gly  Phe  Lys  Asn  Ser  Pro  Thr  Ile>

3130        3140        3150        3160
            *    *      *    *      *    *      *    *      *
          TTT  GAC  GAA  GCC  CTA  CAC  AGG  GAC  CTG  GCC  AAC  TTC  AGG  ATC  CAA  CAC
          Phe  Asp  Glu  Ala  Leu  His  Arg  Asp  Leu  Ala  Asn  Phe  Arg  Ile  Gln  His>

3170        3180        3190        3200        3210
       *    *      *    *      *    *      *    *      *    *
     CCT  CAG  GTG  ACC  CTC  CTC  CAG  TAC  GTG  GAT  GAC  CTG  CTT  CTG  GCG  GGA
     Pro  Gln  Val  Thr  Leu  Leu  Gln  Tyr  Val  Asp  Asp  Leu  Leu  Leu  Ala  Gly>

3220        3230        3240        3250        3260
            *    *      *    *      *    *      *    *      *
          GCC  ACC  AAA  CAG  GAC  TGC  TTA  GAA  GGT  ACG  AAG  GCA  CTA  CTG  CTG  GAA
          Ala  Thr  Lys  Gln  Asp  Cys  Leu  Glu  Gly  Thr  Lys  Ala  Leu  Leu  Leu  Glu>

3270        3280        3290        3300        3310
            *    *      *    *      *    *      *    *      *    *
          TTG  TCT  GAC  CTA  GGC  TAC  AGA  GCC  TCT  GCT  AAG  AAG  GCC  CAG  ATT  TGC
          Leu  Ser  Asp  Leu  Gly  Tyr  Arg  Ala  Ser  Ala  Lys  Lys  Ala  Gln  Ile  Cys>

3320        3330        3340        3350        3360
            *    *      *    *      *    *      *    *      *    *
          AGG  AGA  GAG  GTA  ACA  TAC  TTG  GGG  TAC  AGT  TTG  CGG  GGC  GGG  CAG  CGA
          Arg  Arg  Glu  Val  Thr  Tyr  Leu  Gly  Tyr  Ser  Leu  Arg  Gly  Gly  Gln  Arg>

3370        3380        3390        3400
            *    *      *    *      *    *      *    *      *
          TGG  CTG  ACG  GAG  GCA  CGG  AAG  AAA  ACT  GTA  GTC  CAG  ATA  CCG  GCC  CCA
          Trp  Leu  Thr  Glu  Ala  Arg  Lys  Lys  Thr  Val  Val  Gln  Ile  Pro  Ala  Pro>

3410        3420        3430        3440        3450
       *    *      *    *      *    *      *    *      *    *
     ACC  ACA  GCC  AAA  CAA  GTG  AGA  GAG  TTT  TTG  GGG  ACA  GCT  GGA  TTT  TGC
     Thr  Thr  Ala  Lys  Gln  Val  Arg  Glu  Phe  Leu  Gly  Thr  Ala  Gly  Phe  Cys>

3460        3470        3480        3490        3500
            *    *      *    *      *    *      *    *      *
          AGA  CTG  TGG  ATC  CCG  GGG  TTT  GCG  ACC  TTA  GCA  GCC  CCA  CTC  TAC  CCG
          Arg  Leu  Trp  Ile  Pro  Gly  Phe  Ala  Thr  Leu  Ala  Ala  Pro  Leu  Tyr  Pro>

3510        3520        3530        3540        3550
            *    *      *    *      *    *      *    *      *    *
          CTA  ACC  AAA  GAA  AAA  GGG  GGT  TGC  TTA  CCT  CAG  CAG  GGA  GGG  AAA  TA  AAG
          Leu  Thr  Lys  Glu  Lys  Gly
                              Lys  Arg  Gly  Leu  Leu  Thr  Ser  Ala  Gly  Arg  Glu  Ile  Lys>

3560        3570        3580        3590        3600
            *    *      *    *      *    *      *    *      *    *
          AAC  AAA  GAG  GAA  ATT  CTA  AGC  CTA  TTA  GAA  GCC  TTA  CAT  TTG  CCA  AAA
          Asn  Lys  Glu  Glu  Ile  Leu  Ser  Leu  Leu  Glu  Ala  Leu  His  Leu  Pro  Lys>

3610        3620        3630        3640        3650
            *    *      *    *      *    *      *    *      *    *
          AGG  CTA  GCT  ATT  ATA  CAC  TGT  CCT  GGA  CAT  CAG  AAA  GCC  AAA  GAT  CTC
          Arg  Leu  Ala  Ile  Ile  His  Cys  Pro  Gly  His  Gln  Lys  Ala  Lys  Asp  Leu>
```

FIGURE 2, CONT.

(SEQ ID NO: 2) cont'd

```
            3660        3670        3680        3690
    *     *     *     *     *     *     *     *     *
    ATA TCT AGA GGG AAC CAG ATG GCT GAC CGG GTT GCC AAG CAG GCA GCC
    Ile Ser Arg Gly Asn Gln Met Ala Asp Arg Val Ala Lys Gln Ala Ala>

3700        3710        3720        3730        3740
 *     *     *     *     *     *     *     *     *     *
 CAG GCT GTT AAC CTT CTG CCT ATA ATA GAA ACG CCC AAA GCC CCA GAA
 Gln Ala Val Asn Leu Leu Pro Ile Ile Glu Thr Pro Lys Ala Pro Glu>

3750        3760        3770        3780        3790
    *     *     *     *     *     *     *     *     *     *
    CCC AGA CGA CAG TAC ACC CTA GAA GAC TGG CAA GAG ATA AAA AAG ATA
    Pro Arg Arg Gln Tyr Thr Leu Glu Asp Trp Gln Glu Ile Lys Lys Ile>

3800        3810        3820        3830        3840
    *     *     *     *     *     *     *     *     *     *
    GAC CAG TTC TCT GAG ACT CCG GAG GGG ACC TGC TAT ACC TCA TAT GGG
    Asp Gln Phe Ser Glu Thr Pro Glu Gly Thr Cys Tyr Thr Ser Tyr Gly>

3850        3860        3870        3880        3890
        *     *     *     *     *     *     *     *     *     *
        AAG GAA ATC CTG CCC CAC AAA GAA GGG TTA GAA TAT GTC CAA CAG ATA
        Lys Glu Ile Leu Pro His Lys Glu Gly Leu Glu Tyr Val Gln Gln Ile>

3900        3910        3920        3930
            *     *     *     *     *     *     *     *     *
            CAT CGT CTA ACC CAC CTA GGA ACT AAA CAC CTG CAG CAG TTG GTC AGA
            His Arg Leu Thr His Leu Gly Thr Lys His Leu Gln Gln Leu Val Arg>

3940        3950        3960        3970        3980
 *     *     *     *     *     *     *     *     *     *
 ACA TCC CCT TAT CAT GTT CTG AGG CTA CCA GGA GTG GCT GAC TCG GTG
 Thr Ser Pro Tyr His Val Leu Arg Leu Pro Gly Val Ala Asp Ser Val>

3990        4000        4010        4020        4030
    *     *     *     *     *     *     *     *     *
    GTC AAA CAT TGT GTG CCC TGC CAG CTG GTT AAT GCT AAT CCT TCC AGA
    Val Lys His Cys Val Pro Cys Gln Leu Val Asn Ala Asn Pro Ser Arg>

4040        4050        4060        4070        4080
    *     *     *     *     *     *     *     *     *     *
    ATA CCT CCA GGA AAG AGA CTA AGG GGA AGC CAC CCA GGC GCT CAC TGG
    Ile Pro Pro Gly Lys Arg Leu Arg Gly Ser His Pro Gly Ala His Trp>

4090        4100        4110        4120        4130
        *     *     *     *     *     *     *     *     *     *
        GAA GTG GAC TTC ACT GAG GTA AAG CCG GCT AAA TAC GGA AAC AAA TAT
        Glu Val Asp Phe Thr Glu Val Lys Pro Ala Lys Tyr Gly Asn Lys Tyr>

4140        4150        4160        4170
        *     *     *     *     *     *     *     *     *
        CTA TTG GTT TTT GTA GAC ACC TTT TCA GGA TGG GTA GAG GCT TAT CCT
        Leu Leu Val Phe Val Asp Thr Phe Ser Gly Trp Val Glu Ala Tyr Pro>

4180        4190        4200        4210        4220
 *     *     *     *     *     *     *     *     *     *
 ACT AAA AAA GAG ACT TCA ACC GTG GTG GCT AAG AAA ATA CTG GAG GAA
 Thr Lys Lys Glu Thr Ser Thr Val Val Ala Lys Lys Ile Leu Glu Glu>
```

FIGURE 2, CONT.

(SEQ ID NO: 2) cont'd

```
         4230          4240          4250          4260          4270
           *      *      *      *      *      *      *      *      *
         ATT TTT CCA AGA TTT GGA ATA CCT AAG GTA ATA GGG TCA GAC AAT GGT
         Ile Phe Pro Arg Phe Gly Ile Pro Lys Val Ile Gly Ser Asp Asn Gly>

4280          4290          4300          4310          4320
           *      *      *      *      *      *      *      *      *      *
         CCA GCT TTC GTT GCC CAG GTA AGT CAG GGA CTG GCC AAG ATA TTG GGG
         Pro Ala Phe Val Ala Gln Val Ser Gln Gly Leu Ala Lys Ile Leu Gly>

4330          4340          4350          4360          4370          4380
           *      *      *      *      *      *      *      *      *      *      *      *
         ATT GAT TG A AAA CTG CAT TGT GCA TAC AGA CCC CAA AGC TCA GGA CAG
         Ile Asp      Lys Leu His Cys Ala Tyr Arg Pro Gln Ser Ser Gly Gln>

4380          4390          4400          4410
           *      *      *      *      *      *      *      *
         GTA GAG AGG ATG AAT AGA ACC ATT AAA GAG ACC CTT ACC AAA TTG ACC
         Val Glu Arg Met Asn Arg Thr Ile Lys Glu Thr Leu Thr Lys Leu Thr>

4420          4430          4440          4450          4460
     *      *      *      *      *      *      *      *      *      *
   ACA GAG ACT GGC ATT AAT GAT TGG ATG GCT CTC CTG CCC TTT GTG CTT
   Thr Glu Thr Gly Ile Asn Asp Trp Met Ala Leu Leu Pro Phe Val Leu>

4470          4480          4490          4500          4510
        *      *      *      *      *      *      *      *      *
      TTT AGG GTG AGG AAC ACC CCT GGA CAG TTT GGG CTG ACC CCC TAT AAA
      Phe Arg Val Arg Asn Thr Pro Gly Gln Phe Gly Leu Thr Pro Tyr Lys>

4520          4530          4540          4550          4560
           *      *      *      *      *      *      *      *      *      *
         TTG CTC TAC GGG GGA CCC CCC CCG TTG GCA GAA ATT GCC TTT GCA CAT
         Leu Leu Tyr Gly Gly Pro Pro Pro Leu Ala Glu Ile Ala Phe Ala His>

4570          4580          4590          4600          4610
           *      *      *      *      *      *      *      *      *      *
         AGT GCT GAT GTG CTG CTT TCC CAG CCT TTG TTC TCT AGG CTC AAG GCG
         Ser Ala Asp Val Leu Leu Ser Gln Pro Leu Phe Ser Arg Leu Lys Ala>

4620          4630          4640          4650
           *      *      *      *      *      *      *      *      *
         CTC GAG TGG GTG AGG CAG CGA GCG TGG AAG CAG CTC CGG GAG GCC TAC
         Leu Glu Trp Val Arg Gln Arg Ala Trp Lys Gln Leu Arg Glu Ala Tyr>

4660          4670          4680          4690          4700
     *      *      *      *      *      *      *      *      *      *
   TCA GGA GGA GAC TTG CAA GTT CCA CAT CGC TTC CAA GTT GGA GAT TCA
   Ser Gly Gly Asp Leu Gln Val Pro His Arg Phe Gln Val Gly Asp Ser>

4710          4720          4730          4740          4750
     *      *      *      *      *      *      *      *      *      *
   GTC TAT GTT AGA CGC CAC CGT GCA GGA AAC CTC GAG ACT CGG TAG AAG
   Val Tyr Val Arg Arg His Arg Ala Gly Asn Leu Glu Thr Arg *** Lys>

4760          4770          4780          4790          4800
     *      *      *      *      *      *      *      *      *      *
   GGA CCT TAT CTC GTA CTT TTG ACC ACA CCA ACG GCT GTG AAA GTC GAA
   Gly Pro Tyr Leu Val Leu Leu Thr Thr Pro Thr Ala Val Lys Val Glu>
```

FIGURE 2, CONT.

(SEQ ID NO: 2) cont'd

```
        4810          4820          4830          4840          4850
         *             *             *             *             *
GGA ATC CCC TTA AGC TTC GCC TCC ATC GCG TGG TTC CTT ACT CTG TCA
Gly Ile Pro Leu Ser Phe Ala Ser Ile Ala Trp Phe Leu Thr Leu Ser>

4860          4870          4880          4890
         *             *             *             *
ATA ACT CCT CAA GTT AAT GGT AAA CGC CTT GTG GAC AGC CCG AAC TCC
Ile Thr Pro Gln Val Asn Gly Lys Arg Leu Val Asp Ser Pro Asn Ser>

4900          4910          4920          4930          4940
   *             *             *             *             *
CAT AAA CCC TTA TCT CTC ACC TGG TTA CTT ACT GAC TCC GGT ACA GGT
His Lys Pro Leu Ser Leu Thr Trp Leu Leu Thr Asp Ser Gly Thr Gly>

4950          4960          4970          4980          4990
     *             *             *             *             *
ATT AAT ATT AAC AGC ACT CAA GGG GAG GCT CCC TTG GGG ACC TGG TGG
Ile Asn Ile Asn Ser Thr Gln Gly Glu Ala Pro Leu Gly Thr Trp Trp>

5000          5010          5020          5030          5040
    *             *             *             *             *
CCT GAA TTA TAT GTC TGC CTT CGA TCA GTA ATC CCT GGT CTC AAT GAC
Pro Glu Leu Tyr Val Cys Leu Arg Ser Val Ile Pro Gly Leu Asn Asp>

5050          5060          5070          5080          5090
       *             *             *             *             *
CAG GCC ACA CCC CCC GAT GTA CTC CGT GCT TAC GGG TTT TAC GTT TGC
Gln Ala Thr Pro Pro Asp Val Leu Arg Ala Tyr Gly Phe Tyr Val Cys>

5100          5110          5120          5130
          *             *             *             *
CCA GGA CCC CCA AAT AAT GAA GAA TAT TGT GGA AAT CCT CAG GAT TTC
Pro Gly Pro Pro Asn Asn Glu Glu Tyr Cys Gly Asn Pro Gln Asp Phe>

5140          5150          5160          5170          5180
  *             *             *             *             *
TTT TGC AAG CAA TGG AGC TGC ATA ACT TCT AAT GAT GGG AAT TGG AAA
Phe Cys Lys Gln Trp Ser Cys Ile Thr Ser Asn Asp Gly Asn Trp Lys>

5190          5200          5210          5220          5230
     *             *             *             *             *
TGG CCA GTC TCT CAG CAA GAC AGA GTA AGT TAC TCT TTT GTT AAC AAT
Trp Pro Val Ser Gln Gln Asp Arg Val Ser Tyr Ser Phe Val Asn Asn>

5240          5250          5260          5270          5280
    *             *             *             *             *
CCT ACC AGT TAT AAT CAA TTT AAT TAT GGC CAT GGG AGA TGG AAA GAT
Pro Thr Ser Tyr Asn Gln Phe Asn Tyr Gly His Gly Arg Trp Lys Asp>

5290          5300          5310          5320          5330
       *             *             *             *             *
TGG CAA CAG CGG GTA CAA AAA GAT GTA CGA AAT AAG CAA ATA AGC TGT
Trp Gln Gln Arg Val Gln Lys Asp Val Arg Asn Lys Gln Ile Ser Cys>

5340          5350          5360          5370
         *             *             *             *
CAT TCG TTA GAC CTA GAT TAC TTA AAA ATA AGT TTC ACT GAA AAA GGA
His Ser Leu Asp Leu Asp Tyr Leu Lys Ile Ser Phe Thr Glu Lys Gly>
```

FIGURE 2, CONT.

(SEQ ID NO: 2) cont'd

```
     5380        5390        5400        5410        5420
       *     *     *     *     *     *     *     *     *     *
     AAA CAA GAA AAT ATT CAA AAG TGG GTA AAT GGT ATA TCT TGG GGA ATA
     Lys Gln Glu Asn Ile Gln Lys Trp Val Asn Gly Ile Ser Trp Gly Ile>

5430        5440        5450        5460        5470
            *     *     *     *     *     *     *     *     *     *
          GTG TAC TAT GGA GGC TCT GGG AGA AAG AAA GGA TCT GTT CTG ACT ATT
          Val Tyr Tyr Gly Gly Ser Gly Arg Lys Lys Gly Ser Val Leu Thr Ile>

5480        5490        5500        5510        5520
                 *     *     *     *     *     *     *     *     *     *
               CGC CTC AGA ATA GAA ACT CAG ATG GAA CCT CCG GTT GCT ATA GGA CCA
               Arg Leu Arg Ile Glu Thr Gln Met Glu Pro Pro Val Ala Ile Gly Pro>

5530        5540        5550        5560
                           *     *     *     *     *     *     *     *
                         AAT AAG GGT TTG GCC GAA CAA GGA CCT CCA ATC CAA GAA CAG
                         Asn Lys Gly Leu Ala Glu Gln Gly Pro Pro Ile Gln Glu Gln>

5570        5580        5590        5600        5610
            *     *     *     *     *     *     *     *     *     *
          AGG CCA TCT CCT AAC CCC TCT GAT TAC AAT ACA ACC TCT GGA TCA GTC
          Arg Pro Ser Pro Asn Pro Ser Asp Tyr Asn Thr Thr Ser Gly Ser Val>

5620        5630        5640        5650        5660
                 *     *     *     *     *     *     *     *     *     *
               CCC ACT GAG CCT AAC ATC ACT ATT AAA ACA GGG GCG AAA CTT TTT AGC
               Pro Thr Glu Pro Asn Ile Thr Ile Lys Thr Gly Ala Lys Leu Phe Ser>

5670        5680        5690        5700
                      *     *     *     *     *     *     *     *     *
                    CTC ATC CAG GGA GCT TTT CAA GCT CTT AAC TCC ACG ACT CCA GAG GCT
                    Leu Ile Gln Gly Ala Phe Gln Ala Leu Asn Ser Thr Thr Pro Glu Ala>

5710        5720        5730        5740        5750
       *     *     *     *     *     *     *     *     *     *
     ACC TCT TCT TGT TGG CTT TGC TTA GCT TCG GGC CCA CCT TAC TAT GAG
     Thr Ser Ser Cys Trp Leu Cys Leu Ala Ser Gly Pro Pro Tyr Tyr Glu>

5760        5770        5780        5790        5800
            *     *     *     *     *     *     *     *     *
          GGA ATG GCT AGA GGA GGG AAA TTC AAT GTG ACA AAG GAA CAT AGA GAC
          Gly Met Ala Arg Gly Gly Lys Phe Asn Val Thr Lys Glu His Arg Asp>

5810        5820        5830        5840        5850
                 *     *     *     *     *     *     *     *     *     *
               CAA TGT ACA TGG GGA TCC CAA AAT AAG CTT ACC CTT ACT GAG GTT TCT
               Gln Cys Thr Trp Gly Ser Gln Asn Lys Leu Thr Leu Thr Glu Val Ser>

5860        5870        5880        5890        5900
                      *     *     *     *     *     *     *     *     *     *
                    GGA AAA GGC ACC TGC ATA GGG ATG GTT CCC CCA TCC CAC CAA CAC CTT
                    Gly Lys Gly Thr Cys Ile Gly Met Val Pro Pro Ser His Gln His Leu>

5910        5920        5930        5940
                           *     *     *     *     *     *     *     *
                         TGT AAC CAC ACT GAA GCC TTT AAT CGA ACC TCT GAG AGT CAA TAT CTG
                         Cys Asn His Thr Glu Ala Phe Asn Arg Thr Ser Glu Ser Gln Tyr Leu>
```

FIGURE 2, CONT.

(SEQ ID NO: 2) cont'd

```
      5950          5960          5970          5980          5990
        *       *     *       *     *       *     *       *     *
      GTA CCT GGT TAT GAC AGG TGG TGG GCA TGT AAT ACT GGA TTA ACC CCT
      Val Pro Gly Tyr Asp Arg Trp Trp Ala Cys Asn Thr Gly Leu Thr Pro>

6000          6010          6020          6030          6040
        *       *     *       *     *       *     *       *     *
      TGT GTT TCC ACC TTG GTT TTC AAC CAA ACT AAA GAC TTT TGC GTT ATG
      Cys Val Ser Thr Leu Val Phe Asn Gln Thr Lys Asp Phe Cys Val Met>

6050          6060          6070          6080          6090
        *       *     *       *     *       *     *       *     *
      GTC CAA ATT GTC CCC CGG GTG TAC TAC TAT CCC GAA AAA GCA GTC CTT
      Val Gln Ile Val Pro Arg Val Tyr Tyr Tyr Pro Glu Lys Ala Val Leu>

6100          6110          6120          6130          6140
            *       *     *       *     *       *     *       *     *
      GAT GAA TAT GAC TAT AGA TAT AAT CGG CCA AAA AGA GAG CCC ATA TCC
      Asp Glu Tyr Asp Tyr Arg Tyr Asn Arg Pro Lys Arg Glu Pro Ile Ser>

6150          6160          6170          6180
            *       *     *       *     *       *     *       *     *
      CTG ACA CTA GCT GTA ATG CTC GGA TTG GGA GTG GCT GCA GGC GTG GGA
      Leu Thr Leu Ala Val Met Leu Gly Leu Gly Val Ala Ala Gly Val Gly>

6190          6200          6210          6220          6230
        *       *     *       *     *       *     *       *     *
      ACA GGA ACG GCT GCC CTA ATC ACA GGA CCG CAA CAG CTG GAG AAA GGA
      Thr Gly Thr Ala Ala Leu Ile Thr Gly Pro Gln Gln Leu Glu Lys Gly>

6240          6250          6260          6270          6280
            *       *     *       *     *       *     *       *     *
      CTT AGT AAC CTA CAT CGA ATT GTA ACG GAA GAT CTC CAA GCC CTA GAA
      Leu Ser Asn Leu His Arg Ile Val Thr Glu Asp Leu Gln Ala Leu Glu>

6290          6300          6310          6320          6330
            *       *     *       *     *       *     *       *     *
      AAA TCT GTC AGT AAC CTG GAG GAA TCC CTA ACC TCC TTA TCT GAA GTG
      Lys Ser Val Ser Asn Leu Glu Glu Ser Leu Thr Ser Leu Ser Glu Val>

6340          6350          6360          6370          6380
            *       *     *       *     *       *     *       *     *
      GTT CTA CAG AAC AGA AGG GGG TTA GAT CTG TTA TTT CTA AAA GAA GGA
      Val Leu Gln Asn Arg Arg Gly Leu Asp Leu Leu Phe Leu Lys Glu Gly>

6390          6400          6410          6420
            *       *     *       *     *       *     *       *     *
      GGG TTA TGT GTA GCC TTA AAA GAG GAA TGC TGC TTC TAT GTA GAT CAC
      Gly Leu Cys Val Ala Leu Lys Glu Glu Cys Cys Phe Tyr Val Asp His>

6430          6440          6450          6460          6470
        *       *     *       *     *       *     *       *     *
      TCA GGA GCC ATC AGA GAC TCC ATG AGC AAG CTT AGA GAA AGG TTA GAG
      Ser Gly Ala Ile Arg Asp Ser Met Ser Lys Leu Arg Glu Arg Leu Glu>

6480          6490          6500          6510          6520
            *       *     *       *     *       *     *       *     *
      AGG CGT GA AGG GAA AGA GAG GCT GAC CAG GGG TGG TTT GAA GGA TGG
      Arg Arg Arg Arg Glu Arg Glu Ala Asp Gln Gly Trp Phe Glu Gly Trp>
```

FIGURE 2, CONT.

(SEQ ID NO: 2) cont'd

```
      6530          6540          6550          6560          6570
   *     *     *     *     *     *     *     *     *     *
  TTC   AAC   AGG   TCT   CCT   TGG   ATG   ACC   ACC   CTG   CTT   TCT   GCT   CTG   ACG   GGG
  Phe   Asn   Arg   Ser   Pro   Trp   Met   Thr   Thr   Leu   Leu   Ser   Ala   Leu   Thr   Gly>

6580          6590          6600          6610          6620
   *     *     *     *     *     *     *     *     *     *
  CCC   CTA   GTA   GTC   CTG   CTC   CTG   TTA   CTT   ACA   GTT   GGG   CCT   TGC   TTA   ATT
  Pro   Leu   Val   Val   Leu   Leu   Leu   Leu   Leu   Thr   Val   Gly   Pro   Cys   Leu   Ile>

6630          6640          6650          6660
     *     *     *     *     *     *     *     *     *
    AAT   AGG   TTT   GTT   GCC   TTT   GTT   AGA   GAA   CGA   GTG   AGT   GCA   GTC   CAG   ATC
    Asn   Arg   Phe   Val   Ala   Phe   Val   Arg   Glu   Arg   Val   Ser   Ala   Val   Gln   Ile>

6670          6680          6690          6700          6710
   *     *     *     *     *     *     *     *     *     *
  ATG   GTA   CTT   AGG   CAA   CAG   TAC   CAA   GGC   CTT   CTG   AGC   CAA   GGA   GAA   ACT
  Met   Val   Leu   Arg   Gln   Gln   Tyr   Gln   Gly   Leu   Leu   Ser   Gln   Gly   Glu   Thr>

6720        6730          6740        6750          6760          6770
     *     *     *     *     *     *     *     *     *     *     *
    GAC   CTC   TAGCCTTC   CCAGTTCTAA   GATTAGAACT   ATTAACAAGA   CAAGAAGTGG
    Asp   Leu>
```

```
           6780        6790        6800        6810        6820        6830
         *    *    *    *    *    *    *    *    *    *    *    *
        GGAATGAAAG  GATGAAAATG  CAACCTAACC  CTCCCAGAAC  CCAGGAAGTT  AATAAAAAGC 6840        6850        6860        6870        6880        6890
         *    *    *    *    *    *    *    *    *    *    *    *
        TCTAAATGCC  CCCGAATTCC  AGACCCTGCT  GGCTGCCAGT  AAATAGGTAG  AAGGTCACAC 6900        6910        6920        6930        6940        6950
         *    *    *    *    *    *    *    *    *    *    *    *
        TTCCTATTGT  TCCAGGGCCT  GCTATCCTGG  CCTAAGTAAG  ATAACAGGAA  ATGAGTTGAC 6960        6970        6980        6990        7000        7010
         *    *    *    *    *    *    *    *    *    *    *    *
        TAATCGCTTA  TCTGGATTCT  GTAAAACTGA  CTGGCACCAT  AGAAGAATTG  ATTACACATT 7020        7030        7040        7050        7060        7070
         *    *    *    *    *    *    *    *    *    *    *    *
        GACAGCCCTA  GTGACCTATC  TCAACTGCAA  TCTGTCACTC  TGCCCAGGAG  CCCACGCAGA 7080        7090        7100        7110        7120        7130
         *    *    *    *    *    *    *    *    *    *    *    *
        TGCGGACCTC  CGGAGCTATT  TTAAAATGAT  TGGTCCACGG  AGCGCGGGCT  CTCGATATTT 7140        7150        7160        7170        7180        7190
         *    *    *    *    *    *    *    *    *    *    *    *
        TAAAATGATT  GGTCCATGGA  GCGCGGGCTC  TCGATATTTT  AAAATGATTG  GTTTGTGACG 7200        7210        7220        7230        7240        7250
         *    *    *    *    *    *    *    *    *    *    *    *
        CACAGGCTTT  GTTGTGAACC  CCATAAAAGC  TGTCCCGATT  CCGCACTCGG  GGCCGCAGTC
```

FIGURE 2, CONT.

```
        7260       7270       7280       7290       7300       7310      (SEQ ID NO: 2) cont'd
         *   *      *   *      *   *      *   *      *   *      *   *
CTCTACCCCT GCGTGGTGTA CGACTGTGGG CCCCAGCGCG CTTGGAATAA AAATCCTCTT 7320       7330
         *   *      *   *
GCTGTTTGCA TCAAAAAAAA AAA
```

FIGURE 2, CONT.

(SEQ ID NO: 3)

```
           10         20         30         40         50         60
         *  *       *  *       *  *       *  *       *  *       *  *
    GCGTGGTGTA CGACTGTGGG CCCCAGCGCG CTTGGAATAA AAATCCTCTT GCTGTTTGCA 70         80         90        100        110        120
         *  *       *  *       *  *       *  *       *  *       *  *
    TCAAGACCGC TTCTCGTGAG TGATTAAGGG GAGTCGCCTT TTCCGAGCCT GGAGGTTCTT 130        140        150        160        170        180
         *  *       *  *       *  *       *  *       *  *       *  *
    TTTGCTGGTC TTACATTTGG GGCTCGTCC GGGATCTGTC GCGGCCACCC CTAACACCCG 190        200        210        220        230        240
         *  *       *  *       *  *       *  *       *  *       *  *
    AGAACCGACT TGGAGGTAAA AAGGATCCTC TTTTTAACGT GTATGCATGT ACCGGCCGGC 250        260        270        280        290        300
         *  *       *  *       *  *       *  *       *  *       *  *
    GTCTCTGTTC TGAGTGTCTG TTTTCAGTGG TGCGCGCTTT CGGTTTGCAG CTGTCCTCTC 310        320        330        340        350        360
         *  *       *  *       *  *       *  *       *  *       *  *
    AGGCCGTAAG GGCTGGGGGA CTGTGATCAG CAGACGTGCT AGGAGGATCA CAGGCTGCTG 370        380        390        400        410        420
         *  *       *  *       *  *       *  *       *  *       *  *
    CCCTGGGGGA CGCCCCGGGA GGTGAGGAGA GCCAGGGACG CCTGGTGGTC TCCTACTGTC 430        440        450        460        470        480
         *  *       *  *       *  *       *  *       *  *       *  *
    GGTCAGAGGA CCGAATTCTG TTGCTGAAGC GAAAGCTTCC CCCTCCGCGA CCGTCCGACT 490        500        510        520        530        540
         *  *       *  *       *  *       *  *       *  *       *  *
    CTTTTGCCTG CTTGTGGAAG ACGTGGACGG GTCACGTGTG TCTGGATCTG TTGGTTTCTG 550        560        570        580        590
         *  *       *  *       *  *       *  *       *  *       *
    TTTTGTGTGT CTTTGTCTTG TGTGTCCTTG TCTACAGTTT TAAT ATG GGA CAG ACG
                                                       Met Gly Gln Thr>

600         610         620         630         640
      *           *           *           *           *
    GTG ACG ACC CCT CTT AGT TTG ACT CTC GAC CAT TGG ACT GAA GTT AAA
    Val Thr Thr Pro Leu Ser Leu Thr Leu Asp His Trp Thr Glu Val Lys>

650         660         670         680         690
       *  *        *  *        *  *        *  *        *  *
    TCC AGG GCT CAT AAT TTG TCA GTT CAG GTT AAG AAG GGA CCT TGG CAG
    Ser Arg Ala His Asn Leu Ser Val Gln Val Lys Lys Gly Pro Trp Gln>

700         710         720         730         740
        *  *        *  *        *  *        *  *        *  *
    ACT TTC TGT GTC TCT GAA TGG CCG ACA TTC GAT GTT GGA TGG CCA TCA
    Thr Phe Cys Val Ser Glu Trp Pro Thr Phe Asp Val Gly Trp Pro Ser>
```

FIGURE 3

(SEQ ID NO: 3) cont'd

```
      750         760         770         780
       *           *           *           *       *
GAG GGG ACC TTT AAT TCT GAG ATT ATC CTG GCT GTT AAA GCA GTT ATT
Glu Gly Thr Phe Asn Ser Glu Ile Ile Leu Ala Val Lys Ala Val Ile>

790         800         810         820         830
  *           *           *           *           *
TTT CAG ACT GGA CCC GGC TCT CAT CCC GAT CAG GAG CCC TAT ATC CTT
Phe Gln Thr Gly Pro Gly Ser His Pro Asp Gln Glu Pro Tyr Ile Leu>

840         850         860         870         880
       *           *           *           *           *
ACG TGG CAA GAT TTG GCA GAG GAT CCT CCG CCA TGG GTT AAA CCA TGG
Thr Trp Gln Asp Leu Ala Glu Asp Pro Pro Pro Trp Val Lys Pro Trp>

890         900         910         920         930
       *           *           *           *           *
CTG AAT AAG CCA AGA AAG CCA GGT CCC CGA ATT CTG GCT CTT GGA GAG
Leu Asn Lys Pro Arg Lys Pro Gly Pro Arg Ile Leu Ala Leu Gly Glu>

940         950         960         970         980
            *           *           *           *           *
AAA AAC AAA CAC TCG GCT GAA AAA GTC AAG CCC TCT CCT CAT ATC TAC
Lys Asn Lys His Ser Ala Glu Lys Val Lys Pro Ser Pro His Ile Tyr>

990        1000        1010        1020
            *           *           *           *           *
CCC GAG ATT GAG GAG CCA CCG GCT TGG CCG GAA CCC CAA TCT GTT CCC
Pro Glu Ile Glu Glu Pro Pro Ala Trp Pro Glu Pro Gln Ser Val Pro>

1030        1040        1050        1060        1070
  *           *           *           *           *
CCA CCC CCT TAT CTG GCA CAG GGT GCC GCG AGG GGA CCC TTT GCC CCT
Pro Pro Pro Tyr Leu Ala Gln Gly Ala Ala Arg Gly Pro Phe Ala Pro>

1080        1090        1100        1110        1120
        *           *           *           *           *
CCT GGA GCT CCG GCG GTG GAG GGA CCT GCT GCA GGG ACT CGG AGC CGG
Pro Gly Ala Pro Ala Val Glu Gly Pro Ala Ala Gly Thr Arg Ser Arg>

1130        1140        1150        1160        1170
        *           *           *           *           *
AGG GGC GCC ACC CCG GAG CGG ACA GAC GAG ATC GCG ACA TTA CCG CTG
Arg Gly Ala Thr Pro Glu Arg Thr Asp Glu Ile Ala Thr Leu Pro Leu>

1180        1190        1200        1210        1220
        *           *           *           *           *
CGC ACG TAC GGC CCT CCC ACA CCG GGG GGC CAA TTG CAG CCC CTC CAG
Arg Thr Tyr Gly Pro Pro Thr Pro Gly Gly Gln Leu Gln Pro Leu Gln>

1230        1240        1250        1260
             *           *           *           *           *
TAT TGG CCC TTT TCT TCT GCA GAT CTC TAT AAT TGG AAA ACT AAC CAT
Tyr Trp Pro Phe Ser Ser Ala Asp Leu Tyr Asn Trp Lys Thr Asn His>

1270        1280        1290        1300        1310
  *           *           *           *           *
CCC CCT TTC TCG GAG GAT CCC CAA CGC CTC ACG GGG TTG GTG GAG TCC
Pro Pro Phe Ser Glu Asp Pro Gln Arg Leu Thr Gly Leu Val Glu Ser>
```

FIGURE 3, CONT.

(SEQ ID NO: 3) cont'd

```
        1320            1330            1340            1350            1360
          *       *       *       *       *       *       *       *       *       *
        CTT ATG TTC TCT CAC CAG CCT ACT TGG GAT GAT TGT CAA CAG CTG CTG
        Leu Met Phe Ser His Gln Pro Thr Trp Asp Asp Cys Gln Gln Leu Leu>

1370            1380            1390            1400            1410
          *       *       *       *       *       *       *       *       *       *
        CAG ACA CTC TTC ACA ACC GAG GAG CGA GAG AGA ATT CTA TTA GAG GCT
        Gln Thr Leu Phe Thr Thr Glu Glu Arg Glu Arg Ile Leu Leu Glu Ala>

1420            1430            1440            1450            1460
          *       *       *       *       *       *       *       *       *       *
        AGA AAA AAT GTT CCT GGG GCC GAC GGG CGA CCC ACG CGG TTG CAA AAT
        Arg Lys Asn Val Pro Gly Ala Asp Gly Arg Pro Thr Arg Leu Gln Asn>

1470            1480            1490            1500
          *       *       *       *       *       *       *       *       *
        GAG ATT GAC ATG GGA TTT CCC TTA ACT CGC CCC GGT TGG GAC TAC AAC
        Glu Ile Asp Met Gly Phe Pro Leu Thr Arg Pro Gly Trp Asp Tyr Asn>

1510            1520            1530            1540            1550
  *       *       *       *       *       *       *       *       *       *
ACG GCT GAA GGT AGG GAG AGC TTG AAA ATC TAT CGC CAG GCT CTG GTG
Thr Ala Glu Gly Arg Glu Ser Leu Lys Ile Tyr Arg Gln Ala Leu Val>

1560            1570            1580            1590            1600
          *       *       *       *       *       *       *       *       *       *
        GCG GGT CTC CGG GGC GCC TCA AGA CGG CCC ACT AAT TTG GCT AAG GTA
        Ala Gly Leu Arg Gly Ala Ser Arg Arg Pro Thr Asn Leu Ala Lys Val>

1610            1620            1630            1640            1650
          *       *       *       *       *       *       *       *       *       *
        AGA GAA GTG ATG CAG GGA CCG AAT GAA CCC CCC TCT GTT TTT CTT GAG
        Arg Glu Val Met Gln Gly Pro Asn Glu Pro Pro Ser Val Phe Leu Glu>

1660            1670            1680            1690            1700
          *       *       *       *       *       *       *       *       *       *
        AGG CTC TTG GAA GCC TTC AGG CGG TAC ACC CCT TTT GAT CCC ACC TCA
        Arg Leu Leu Glu Ala Phe Arg Arg Tyr Thr Pro Phe Asp Pro Thr Ser>

1710            1720            1730            1740
          *       *       *       *       *       *       *       *       *
        GAG GCC CAA AAA GCC TCA GTG GCT TTG GCC TTT ATA GGA CAG TCA GCC
        Glu Ala Gln Lys Ala Ser Val Ala Leu Ala Phe Ile Gly Gln Ser Ala>

1750            1760            1770            1780            1790
  *       *       *       *       *       *       *       *       *       *
TTG GAT ATT AGA AAG AAG CTT CAG AGA CTG GAA GGG TTA CAG GAG GCT
Leu Asp Ile Arg Lys Lys Leu Gln Arg Leu Glu Gly Leu Gln Glu Ala>

1800            1810            1820            1830            1840
          *       *       *       *       *       *       *       *       *
        GAG TTA CGT GAT CTA GTG AAG GAG GCA GAG AAA GTA TAT TAC AAA AGG
        Glu Leu Arg Asp Leu Val Lys Glu Ala Glu Lys Val Tyr Tyr Lys Arg>

1850            1860            1870            1880            1890
          *       *       *       *       *       *       *       *       *       *
        GAG ACA GAA GAA GAA AGG GAA CAA AGA AAA GAG AGA GAA AGA GAG GAA
        Glu Thr Glu Glu Glu Arg Glu Gln Arg Lys Glu Arg Glu Arg Glu Glu>
```

FIGURE 3, CONT.

(SEQ ID NO: 3) cont'd

```
              1900        1910        1920        1930        1940
               *           *           *           *           *
        AGG GAG GAA AGA CGT AAT AAA CGG CAA GAG AAG AAT TTG ACT AAG ATC
        Arg Glu Glu Arg Arg Asn Lys Arg Gln Glu Lys Asn Leu Thr Lys Ile>

1950        1960        1970        1980
                    *           *           *           *           *
        TTG GCT GCA GTG GTT GAA GGG AAA AGC AAT ACG GAA AGA GAG AGA GAT
        Leu Ala Ala Val Val Glu Gly Lys Ser Asn Thr Glu Arg Glu Arg Asp>

1990        2000        2010        2020        2030
      *           *           *           *           *           *
     TTT AGG AAA ATT AGG TCA GGC CCT AGA CAG TCA GGG AAC CTG GGC AAT
     Phe Arg Lys Ile Arg Ser Gly Pro Arg Gln Ser Gly Asn Leu Gly Asn>

2040        2050        2060        2070        2080
          *           *           *           *           *
        AGG ACC CCA CTC GAC AAG GAC CAA TGT GCA TAT TGT AAA GAA AGA GGA
        Arg Thr Pro Leu Asp Lys Asp Gln Cys Ala Tyr Cys Lys Glu Arg Gly>

2090        2100        2110        2120        2130
              *           *           *           *           *
        CAC TGG GCA AGG AAC TGC CCC AAG AAG GGA AAC AAA GGA CCA AGG ATC
        His Trp Ala Arg Asn Cys Pro Lys Lys Gly Asn Lys Gly Pro Arg Ile>

2140        2150        2160        2170        2180
                  *           *           *           *           *
        CTA GCT CTA GAA GAA GAT AAA GAT TAGG GGAGACGGGG TTCGGACCCC
        Leu Ala Leu Glu Glu Asp Lys Asp>

2190        2200        2210        2220        2230        2240
                      *           *           *           *           *           *
        CTCCCCGAGC CCAGGGTAAC TTTGAAGGTG GAGGGGCAAC CAGTTGAGTT CCTGGTTGAT 2250        2260        2270        2280        2290        2300
                      *           *           *           *           *           *
        ACCGGAGCGA AACATTCAGT GCTACTACAG CCATTAGGAA AACTAAAAGA TAAAAAATCC 2310        2320        2330        2340        2350
                          *           *           *           *           *
        TGGGTG ATG GGT GCC ACA GGG CAA CAA CAG TAT CCA TGG ACT ACC CGA AGA
               Met Gly Ala Thr Gly Gln Gln Gln Tyr Pro Trp Thr Thr Arg Arg>

2360        2370        2380        2390
                      *           *           *           *
        ACA GTT GAC TTG GGA GTG GGA CGG GTA ACC CAC TCG TTT CTG GTC ATA
        Thr Val Asp Leu Gly Val Gly Arg Val Thr His Ser Phe Leu Val Ile>

2400        2410        2420        2430        2440
      *           *           *           *           *
     CCT GAG TGC CCA GCA CCC CTC TTA GGT AGA GAC TTA TTG ACC AAG ATG
     Pro Glu Cys Pro Ala Pro Leu Leu Gly Arg Asp Leu Leu Thr Lys Met>

2450        2460        2470        2480        2490
          *           *           *           *           *
        GGA GCA CAA ATT TCT TTT GAA CAA GGG AAA CCA GAA GTG TCT GCA AAT
        Gly Ala Gln Ile Ser Phe Glu Gln Gly Lys Pro Glu Val Ser Ala Asn>
```

FIGURE 3, CONT.

(SEQ ID NO: 3) cont'd

```
         2500          2510          2520          2530          2540
           *       *     *       *     *       *     *       *     *
        AAC AAA CCT ATC ACT GTG TTG ACC CTC CAA TTA GAT GAC GAA TAT CGA
        Asn Lys Pro Ile Thr Val Leu Thr Leu Gln Leu Asp Asp Glu Tyr Arg>

2550          2560          2570          2580          2590
          *       *     *       *     *       *     *       *     *     *
        CTA TAC TCT CCC CTA GTA AAG CCT GAT CAA AAT ATA CAA TTC TGG TTG
        Leu Tyr Ser Pro Leu Val Lys Pro Asp Gln Asn Ile Gln Phe Trp Leu>

2600          2610          2620          2630
          *       *     *       *     *       *     *       *     *
        GAA CAG TTT CCC CAA GCC TGG GCA GAA ACC GCA GGG ATG GGT TTG GCA
        Glu Gln Phe Pro Gln Ala Trp Ala Glu Thr Ala Gly Met Gly Leu Ala>

2640          2650          2660          2670          2680
     *       *     *       *     *       *     *       *     *     *
   AAG CAA GTT CCC CCA CAA GTT ATT CAA CTG AAG GCC AGT GCC ACA CCA
   Lys Gln Val Pro Pro Gln Val Ile Gln Leu Lys Ala Ser Ala Thr Pro>

2690          2700          2710          2720          2730
      *       *     *       *     *       *     *       *     *     *
    GTG TCA GTC AGA CAG TAC CCC TTG AGT AAA GAA GCT CAA GAA GGA ATT
    Val Ser Val Arg Gln Tyr Pro Leu Ser Lys Glu Ala Gln Glu Gly Ile>

2740          2750          2760          2770          2780
         *       *     *       *     *       *     *       *     *
       CGG CCG CAT GTC CAA AGA TTA ATC CAA CAG GGC ATC CTA GTT CCT GTC
       Arg Pro His Val Gln Arg Leu Ile Gln Gln Gly Ile Leu Val Pro Val>

2790          2800          2810          2820          2830
          *       *     *       *     *       *     *       *     *     *
        CAA TCT CCC TGG AAT ACT CCC CTG CTA CCG GTT AGA AAG CCT GGG ACT
        Gln Ser Pro Trp Asn Thr Pro Leu Leu Pro Val Arg Lys Pro Gly Thr>

2840          2850          2860          2870
          *       *     *       *     *       *     *       *     *
        AAT GAC TAT CGA CCA GTA CAG GAC TTG AGA GAG GTC AAT AAA CGG GTG
        Asn Asp Tyr Arg Pro Val Gln Asp Leu Arg Glu Val Asn Lys Arg Val>

2880          2890          2900          2910          2920
     *       *     *       *     *       *     *       *     *     *
   CAG GAT ATA CAC CCA ACA GTC CCG AAC CCT TAT AAC CTC TTG TGT GCT
   Gln Asp Ile His Pro Thr Val Pro Asn Pro Tyr Asn Leu Leu Cys Ala>

2930          2940          2950          2960          2970
      *       *     *       *     *       *     *       *     *     *
    CTC CCA CCC CAA CGG AGC TGG TAT ACA GTA TTG GAC TTA AAG GAT GCC
    Leu Pro Pro Gln Arg Ser Trp Tyr Thr Val Leu Asp Leu Lys Asp Ala>

2980          2990          3000          3010          3020
         *       *     *       *     *       *     *       *     *
       TTC TTC TGC CTG AGA TTA CAC CCC ACT AGC CAA CCA CTT TTT GCC TTC
       Phe Phe Cys Leu Arg Leu His Pro Thr Ser Gln Pro Leu Phe Ala Phe>

3030          3040          3050          3060          3070
          *       *     *       *     *       *     *       *     *     *
        GAA TGG AGA GAT CCA GGT ACG GGA AGA ACC GGG CAG CTC ACC TGG ACC
        Glu Trp Arg Asp Pro Gly Thr Gly Arg Thr Gly Gln Leu Thr Trp Thr>
```

FIGURE 3, CONT.

(SEQ ID NO: 3) cont'd

```
              3080         3090         3100         3110
               *    *    *    *    *    *    *    *    *
              CGA  CTG  CCC  CAA  GGG  TTC  AAG  AAC  TCC  CCG  ACC  ATC  TTT  GAC  GAA  GCC
              Arg  Leu  Pro  Gln  Gly  Phe  Lys  Asn  Ser  Pro  Thr  Ile  Phe  Asp  Glu  Ala>

3120         3130         3140         3150         3160
   *    *    *    *    *    *    *    *    *    *
  CTA  CAC  AGA  GAC  CTG  GCC  AAC  TTC  AGG  ATC  CAA  CAC  CCT  CAG  GTG  ACC
  Leu  His  Arg  Asp  Leu  Ala  Asn  Phe  Arg  Ile  Gln  His  Pro  Gln  Val  Thr>

3170         3180         3190         3200         3210
   *    *    *    *    *    *    *    *    *    *
  CTC  CTC  CAG  TAC  GTG  GAT  GAC  CTG  CTT  CTG  GCG  GGA  GCC  ACC  AAA  CAG
  Leu  Leu  Gln  Tyr  Val  Asp  Asp  Leu  Leu  Leu  Ala  Gly  Ala  Thr  Lys  Gln>

3220         3230         3240         3250         3260
           *    *    *    *    *    *    *    *    *    *
          GAC  TGC  TTA  GAA  GGC  ACG  AAG  GCA  CTA  CTG  CTG  GAA  TTG  TCT  GAC  CTA
          Asp  Cys  Leu  Glu  Gly  Thr  Lys  Ala  Leu  Leu  Leu  Glu  Leu  Ser  Asp  Leu>

3270         3280         3290         3300         3310
                *    *    *    *    *    *    *    *    *    *
               GGC  TAC  AGA  GCC  TCT  GCT  AAG  AAG  GCC  CAG  ATT  TGC  AGG  AGA  GAG  GTA
               Gly  Tyr  Arg  Ala  Ser  Ala  Lys  Lys  Ala  Gln  Ile  Cys  Arg  Arg  Glu  Val>

3320         3330         3340         3350
           *    *    *    *    *    *    *    *    *
          ACA  TAC  TTG  GGG  TAC  AGT  TTG  CGG  GAC  GGG  CAG  CGA  TGG  CTG  ACG  GAG
          Thr  Tyr  Leu  Gly  Tyr  Ser  Leu  Arg  Asp  Gly  Gln  Arg  Trp  Leu  Thr  Glu>

3360         3370         3380         3390         3400
   *    *    *    *    *    *    *    *    *    *
  GCA  CGG  AAG  AAA  ACT  GTA  GTC  CAG  ATA  CCG  GCC  CCA  ACC  ACA  GCC  AAA
  Ala  Arg  Lys  Lys  Thr  Val  Val  Gln  Ile  Pro  Ala  Pro  Thr  Thr  Ala  Lys>

3410         3420         3430         3440         3450
   *    *    *    *    *    *    *    *    *    *
  CAA  ATG  AGA  GAG  TTT  TTG  GGG  ACA  GCT  GGA  TTT  TGC  AGA  CTG  TGG  ATC
  Gln  Met  Arg  Glu  Phe  Leu  Gly  Thr  Ala  Gly  Phe  Cys  Arg  Leu  Trp  Ile>

3460         3470         3480         3490         3500
           *    *    *    *    *    *    *    *    *
          CCG  GGG  TTT  GCG  ACC  TTA  GCA  GCC  CCA  CTC  TAC  CCG  CTA  ACC  AAA  GAA
          Pro  Gly  Phe  Ala  Thr  Leu  Ala  Ala  Pro  Leu  Tyr  Pro  Leu  Thr  Lys  Glu>

3510         3520         3530         3540         3550
                *    *    *    *    *    *    *    *    *    *
               AAA  GGG  GAA  TTC  TCC  TGG  GCT  CCT  GAG  CAC  CAG  AAG  GCA  TTT  GAT  GCT
               Lys  Gly  Glu  Phe  Ser  Trp  Ala  Pro  Glu  His  Gln  Lys  Ala  Phe  Asp  Ala>

3560         3570         3580         3590
           *    *    *    *    *    *    *    *    *
          ATC  AAA  AAG  GCC  CTG  CTG  AGC  GCA  CCT  GCT  CTG  GCC  CTC  CCT  GAC  GTA
          Ile  Lys  Lys  Ala  Leu  Leu  Ser  Ala  Pro  Ala  Leu  Ala  Leu  Pro  Asp  Val>

3600         3610         3620         3630         3640
   *    *    *    *    *    *    *    *    *    *
  ACT  AAA  CCC  TTT  ACC  CTT  TAT  GTG  GAT  GAG  CGT  AAG  GGA  GTA  GCC  CGG
  Thr  Lys  Pro  Phe  Thr  Leu  Tyr  Val  Asp  Glu  Arg  Lys  Gly  Val  Ala  Arg>
```

FIGURE 3, CONT.

(SEQ ID NO: 3) cont'd

```
      3650        3660        3670        3680        3690
        *     *     *     *     *     *     *     *     *     *
      GGA GTT TTA ACC CAA ACC CTA GGA CCA TGG AGA AGA CCT GTC GCC TAC
      Gly Val Leu Thr Gln Thr Leu Gly Pro Trp Arg Arg Pro Val Ala Tyr>

3700        3710        3720        3730        3740
        *     *     *     *     *     *     *     *     *
      CTG TCA AAG AAG CTC GAT CCT GTA GCC AGT GGT TGG CCC ATA TGC CTG
      Leu Ser Lys Lys Leu Asp Pro Val Ala Ser Gly Trp Pro Ile Cys Leu>

3750        3760        3770        3780        3790
        *     *     *     *     *     *     *     *     *     *
      AAG GCT ATC GCA GCT GTG GCC ATA CTG GTC AAG GAC GCT GAC AAA TTG
      Lys Ala Ile Ala Ala Val Ala Ile Leu Val Lys Asp Ala Asp Lys Leu>

3800        3810        3820        3830
        *·    *     *     *     *     *     *     *     *
      ACT TTG GGA CAG AAT ATA ACT GTA ATA GCC CCC CAT GCA TTG GAG AAC
      Thr Leu Gly Gln Asn Ile Thr Val Ile Ala Pro His Ala Leu Glu Asn>

3840        3850        3860        3870        3880
  *     *     *     *     *     *     *     *     *     *
ATC GTT CGG CAG CCC CCA GAC CGA TGG ATG ACC AAC GCC CGC ATG ACC
Ile Val Arg Gln Pro Pro Asp Arg Trp Met Thr Asn Ala Arg Met Thr>

3890        3900        3910        3920        3930
  *     *     *     *     *     *     *     *     *     *
CAC TAT CAA AGC CTG CTT CTC ACA GAG AGG GTC ACG TTC GCT CCA CCA
His Tyr Gln Ser Leu Leu Leu Thr Glu Arg Val Thr Phe Ala Pro Pro>

3940        3950        3960        3970        3980
        *     *     *     *     *     *     *     *     *
      GCC GCT CTC AAC CCT GCC ACT CTT CTG CCT GAA GAG ACT GAT GAA CCA
      Ala Ala Leu Asn Pro Ala Thr Leu Leu Pro Glu Glu Thr Asp Glu Pro>

3990        4000        4010        4020        4030
        *     *     *     *     *     *     *     *     *     *
      GTG ACT CAT GAT TGC CAT CAA CTA TTG ATT GAG GAG ACT GGG GTC CGC
      Val Thr His Asp Cys His Gln Leu Leu Ile Glu Glu Thr Gly Val Arg>

4040        4050        4060        4070
        *     *     *     *     *     *     *     *     *
      AAG GAC CTT ACA GAC ATA CCG CTG ACT GGA GAA GTG CTA ACC TGG TTC
      Lys Asp Leu Thr Asp Ile Pro Leu Thr Gly Glu Val Leu Thr Trp Phe>

4080        4090        4100        4110        4120
  *     *     *     *     *     *     *     *     *     *
ACT GAC GGA AGC AGC TAT GTG GTG GAA GGT AAG AGG ATG GCT GGG GCG
Thr Asp Gly Ser Ser Tyr Val Val Glu Gly Lys Arg Met Ala Gly Ala>

4130        4140        4150        4160        4170
        *     *     *     *     *     *     *     *     *     *
      GCG GTG GTG GAC GGG ACC CGC ACG ATC TGG GCC AGC AGC CTG CCG GAA
      Ala Val Val Asp Gly Thr Arg Thr Ile Trp Ala Ser Ser Leu Pro Glu>

4180        4190        4200        4210        4220
        *     *     *     *     *     *     *     *     *
      GGA ACT TCA GCA CAA AAG GCT GAG CTC ATG GCC CTC ACG CAA GCT TTG
      Gly Thr Ser Ala Gln Lys Ala Glu Leu Met Ala Leu Thr Gln Ala Leu>
```

FIGURE 3, CONT.

(SEQ ID NO: 3) cont'd

```
          4230        4240        4250        4260        4270
            *           *           *           *           *
    CGG CTG GCC GAA GGG AAA TCC ATA AAC ATT TAT ACG GAC AGC AGG TAT
    Arg Leu Ala Glu Gly Lys Ser Ile Asn Ile Tyr Thr Asp Ser Arg Tyr>

4280        4290        4300        4310
                *           *           *           *
    GCC TTT GCG ACT GCA CAC GTA CAT GGG GCC ATC TAT AAA CAA AGG GGG
    Ala Phe Ala Thr Ala His Val His Gly Ala Ile Tyr Lys Gln Arg Gly>

4320        4330        4340        4350        4360
    *           *           *           *           *
    TTG CTT ACC TCA GCA GGG AGG GAA ATA AAG AAC AAA GAG GAA ATT CTA
    Leu Leu Thr Ser Ala Gly Arg Glu Ile Lys Asn Lys Glu Glu Ile Leu>

4370        4380        4390        4400        4410
    *           *           *           *           *
    AGC CTA TTA GAA GCC GTA CAT TTA CCA AAA AGG CTA GCT ATT ATA CAC
    Ser Leu Leu Glu Ala Val His Leu Pro Lys Arg Leu Ala Ile Ile His>

4420        4430        4440        4450        4460
            *           *           *           *           *
    TGT CCT GGA CAT CAG AAA GCT AAA GAT CTC ATA TCC AGA GGA AAC CAG
    Cys Pro Gly His Gln Lys Ala Lys Asp Leu Ile Ser Arg Gly Asn Gln>

4470        4480        4490        4500        4510
                *           *           *           *           *
    ATG GCT GAC CGG GTT GCC AAG CAG GCA GCC CAG GGT GTT AAC CTT CTG
    Met Ala Asp Arg Val Ala Lys Gln Ala Ala Gln Gly Val Asn Leu Leu>

4520        4530        4540        4550
                *           *           *           *
    CCT ATA ATA GAA ATG CCC AAA GCC CCA GAA CCC AGA CGA CAG TAC ACC
    Pro Ile Ile Glu Met Pro Lys Ala Pro Glu Pro Arg Arg Gln Tyr Thr>

4560        4570        4580        4590        4600
    *           *           *           *           *
    CTA GAA GAC TGG CAA GAG ATA AAA AAG ATA GAC CAG TTC TCT GAG ACT
    Leu Glu Asp Trp Gln Glu Ile Lys Lys Ile Asp Gln Phe Ser Glu Thr>

4610        4620        4630        4640        4650
    *           *           *           *           *
    CCG GAA GGG ACC TGC TAT ACC TCA GAT GGG AAG GAA ATC CTG CCC CAC
    Pro Glu Gly Thr Cys Tyr Thr Ser Asp Gly Lys Glu Ile Leu Pro His>

4660        4670        4680        4690        4700
            *           *           *           *           *
    AAA GAA GGG TTA GAA TAT GTC CAA CAG ATA CAT CGT CTA ACC CAC CTA
    Lys Glu Gly Leu Glu Tyr Val Gln Gln Ile His Arg Leu Thr His Leu>

4710        4720        4730        4740        4750
            *           *           *           *           *
    GGA ACT AAA CAC CTG CAG CAG TTG GTC AGA ACA TCC CCT TAT CAT GTT
    Gly Thr Lys His Leu Gln Gln Leu Val Arg Thr Ser Pro Tyr His Val>

4760        4770        4780        4790
                *           *           *           *
    CTG AGG CTA CCA GGA GTG GCT GAC TCG GTG GTC AAA CAT TGT GTG CCC
    Leu Arg Leu Pro Gly Val Ala Asp Ser Val Val Lys His Cys Val Pro>
```

FIGURE 3, CONT.

(SEQ ID NO: 3) cont'd

```
4800        4810        4820        4830        4840
 *     *     *     *     *     *     *     *     *     *
TGC   CAG   CTG   GTT   AAT   GCT   AAT   CCT   TCC   AGA   ATG   CCT   CCA   GGG   AAG   AGA
Cys   Gln   Leu   Val   Asn   Ala   Asn   Pro   Ser   Arg   Met   Pro   Pro   Gly   Lys   Arg>

4850        4860        4870        4880        4890
  *     *     *     *     *     *     *     *     *     *
CTA   AGG   GGA   AGC   CAC   CCA   GGC   GCT   CAC   TGG   GAA   GTG   GAC   TTC   ACT   GAG
Leu   Arg   Gly   Ser   His   Pro   Gly   Ala   His   Trp   Glu   Val   Asp   Phe   Thr   Glu>

4900        4910        4920        4930        4940
  *     *     *     *     *     *     *     *     *     *
GTA   AAG   CCG   GCT   AAA   TAC   GGA   AAC   AAA   TAC   CTA   TTG   GTT   TTT   GTA   GAC
Val   Lys   Pro   Ala   Lys   Tyr   Gly   Asn   Lys   Tyr   Leu   Leu   Val   Phe   Val   Asp>

4950        4960        4970        4980        4990
  *     *     *     *     *     *     *     *     *     *
ACC   TTT   TCA   GGA   TGG   GTA   GAG   GCT   TAT   CCT   ACT   AAG   AAA   GAG   ACT   TCA
Thr   Phe   Ser   Gly   Trp   Val   Glu   Ala   Tyr   Pro   Thr   Lys   Lys   Glu   Thr   Ser>

5000        5010        5020        5030
  *     *     *     *     *     *     *     *     *
ACC   GTG   GTG   GCT   AAA   AAA   ATA   CTG   GAA   GAA   ATT   TTT   CCA   AGA   TTT   GGA
Thr   Val   Val   Ala   Lys   Lys   Ile   Leu   Glu   Glu   Ile   Phe   Pro   Arg   Phe   Gly>

5040        5050        5060        5070        5080
 *     *     *     *     *     *     *     *     *     *
ATA   CCT   AAG   GTA   ATA   GGG   TCA   GAC   AAT   GGT   CCA   GCT   TTT   GTT   GCC   CAC
Ile   Pro   Lys   Val   Ile   Gly   Ser   Asp   Asn   Gly   Pro   Ala   Phe   Val   Ala   Gln>

5090        5100        5110        5120        5130
 *     *     *     *     *     *     *     *     *     *
GTA   AGT   CAG   GGA   CTG   GCC   AAG   ATA   TTG   GGG   ATT   GAT   TGG   AAA   CTG   CAT
Val   Ser   Gln   Gly   Leu   Ala   Lys   Ile   Leu   Gly   Ile   Asp   Trp   Lys   Leu   His>

5140        5150        5160        5170        5180
  *     *     *     *     *     *     *     *     *     *
TGT   GCA   TAC   AGA   CCC   CAA   AGC   TCA   GGA   CAG   GTA   GAG   AGG   ATG   AAT   AGA
Cys   Ala   Tyr   Arg   Pro   Gln   Ser   Ser   Gly   Gln   Val   Glu   Arg   Met   Asn   Arg>

5190        5200        5210        5220        5230
  *     *     *     *     *     *     *     *     *     *
ACC   ATT   AAA   GAG   ACC   CTT   ACT   AAA   TTG   ACC   GCG   GAG   ACT   GGC   GTT   AAT
Thr   Ile   Lys   Glu   Thr   Leu   Thr   Lys   Leu   Thr   Ala   Glu   Thr   Gly   Val   Asn>

5240        5250        5260        5270
  *     *     *     *     *     *     *     *     *
GAT   TGG   ATA   GCT   CTC   CTG   CCC   TTT   GTG   CTT   TTT   AGG   GTT   AGG   AAC   ACC
Asp   Trp   Ile   Ala   Leu   Leu   Pro   Phe   Val   Leu   Phe   Arg   Val   Arg   Asn   Thr>

5280        5290        5300        5310        5320
 *     *     *     *     *     *     *     *     *     *
CCT   GGA   CAG   TTT   GGG   CTG   ACC   CCC   TAT   GAA   TTA   CTC   TAC   GGG   GGA   CCC
Pro   Gly   Gln   Phe   Gly   Leu   Thr   Pro   Tyr   Glu   Leu   Leu   Tyr   Gly   Gly   Pro>

5330        5340        5350        5360        5370
 *     *     *     *     *     *     *     *     *     *
CCC   CCA   TTG   GTA   GAA   ATT   GCT   TCT   GTA   CAT   AGT   GCT   GAC   GTG   CTG   CTT
Pro   Pro   Leu   Val   Glu   Ile   Ala   Ser   Val   His   Ser   Ala   Asp   Val   Leu   Leu>
```

FIGURE 3, CONT.

(SEQ ID NO: 3) cont'd

```
         5380          5390          5400          5410          5420
           *     *       *     *       *     *       *     *       *     *
         TCC CAG CCT TTG TTC TCT AGG CTC AAG GCA CTT GAG TGG GTG AGA CAA
         Ser Gln Pro Leu Phe Ser Arg Leu Lys Ala Leu Glu Trp Val Arg Gln>

5430          5440          5450          5460          5470
           *     *       *     *       *     *       *     *       *     *
         CGA GCG TGG AGG CAA CTC CGG GAG GCC TAC TCA GGA GGA GGA GAC TTG
         Arg Ala Trp Arg Gln Leu Arg Glu Ala Tyr Ser Gly Gly Gly Asp Leu>

5480          5490          5500          5510
           *     *       *     *       *     *       *     *       *
         CAG ATC CCA CAT CGT TTC CAA GTG GGA GAT TCA GTC TAC GTT AGA CGC
         Gln Ile Pro His Arg Phe Gln Val Gly Asp Ser Val Tyr Val Arg Arg>

5520          5530          5540          5550          5560
     *     *       *     *       *     *       *     *       *     *
   CAC CGT GCA GGA AAC CTC GAG ACT CGG TGG AAG GGC CCT TAT CTC GTA
   His Arg Ala Gly Asn Leu Glu Thr Arg Trp Lys Gly Pro Tyr Leu Val>

5570          5580          5590          5600          5610
          *     *       *     *       *     *       *     *       *     *
        CTT TTG ACC ACA CCA ACG GCT GTG AAA GTC GAA GGA ATC TCC ACC TGG
        Leu Leu Thr Thr Pro Thr Ala Val Lys Val Glu Gly Ile Ser Thr Trp>

5620          5630          5640          5650          5660
             *     *       *     *       *     *       *     *       *
           ATC CAT GCA TCC CAC GTT AAA CCG GCG CCA CCT CCC GAT TCG GGG TGG
               Met His Pro Thr Leu Asn Arg Arg His Leu Pro Ile Arg Gly Gly>

Ile His Ala Ser His Val Lys Pro Ala Pro Pro Pro Asp Ser Gly Trp>

5670          5680          5690          5700          5710
                *     *       *     *       *     *       *     *       *     *
              AAA GCC GAA AAG ACT GAA AAT CCC CTT AAG CTT CGC CTC CAT CGC GTG
              Lys Pro Lys Arg Leu Lys Ile Pro Leu Ser Phe Ala Ser Ile Ala Trp>

Lys Ala Glu Lys Thr Glu Asn Pro Leu Lys Leu Arg Leu His Arg Val>

5720          5730          5740          5750          5760
                   *     *       *     *       *      *      *     *       *     *
                 GTT CCT TAC TCT GTC AAT AAC CTC TCA GAC T AAT GGT ATG CGC ATA GGA
                 Phe Leu Thr Leu Ser Ile Thr Ser Gln Thr   Asn Gly Met Arg Ile Gly>

Val Pro Tyr Ser Val Asn Asn Leu Ser Asp>

5770          5780          5790          5800
                      *     *       *     *       *     *       *     *       *
                    GAC AGC CTG AAC TCC CAT AAA CCC TTA TCT CTC ACC TGG TTA ATT ACT
                    Asp Ser Leu Asn Ser His Lys Pro Leu Ser Leu Thr Trp Leu Ile Thr>

5810          5820          5830          5840          5850
     *     *       *     *       *     *       *     *       *     *
   GAC TCC GGC ACA GGT ATT AAT ATC AAC AAC ACT CAA GGG GAG GCT CCT
   Asp Ser Gly Thr Gly Ile Asn Ile Asn Asn Thr Gln Gly Glu Ala Pro>
```

FIGURE 3, CONT.

(SEQ ID NO: 3) cont'd

```
          5860          5870          5880          5890          5900
            *       *       *       *       *       *       *       *       *
          TTA GGA ACC TGG TGG CCT GAT CTA TAC GTT TGC CTC AGA TCA GTT ATT
          Leu Gly Thr Trp Trp Pro Asp Leu Tyr Val Cys Leu Arg Ser Val Ile>

5910          5920          5930          5940          5950
            *       *       *       *       *       *       *       *       *       *
          CCT AGT CTG ACC TCA CCC CCA GAT ATC CTC CAT GCT CAC GGA TTT TAT
          Pro Ser Leu Thr Ser Pro Pro Asp Ile Leu His Ala His Gly Phe Tyr>

5960          5970          5980          5990          6000
                *       *       *       *       *       *       *       *       *       *
          GTT TGC CCA GGA CCA CCA AAT AAT GGA AAA CAT TGC GGA AAT CCC AGA
          Val Cys Pro Gly Pro Pro Asn Asn Gly Lys His Cys Gly Asn Pro Arg>

6010          6020          6030          6040
                        *       *       *       *       *       *       *       *       *
          GAT TTC TTT TGT AAA CAA TGG AAC TGT GTA ACC TCT AAT GAT GGA TAT
          Asp Phe Phe Cys Lys Gln Trp Asn Cys Val Thr Ser Asn Asp Gly Tyr>

6050          6060          6070          6080          6090
            *       *       *       *       *       *       *       *       *       *
          TGG AAA TGG CCA ACC TCT CAG CAG GAT AGG GTA AGT TTT TCT TAT GTC
          Trp Lys Trp Pro Thr Ser Gln Gln Asp Arg Val Ser Phe Ser Tyr Val>

6100          6110          6120          6130          6140
            *       *       *       *       *       *       *       *       *
          AAC ACC TAT ACC AGC TCT GGA CAA TTT AAT TAC CTG ACC TGG ATT AGA
          Asn Thr Tyr Thr Ser Ser Gly Gln Phe Asn Tyr Leu Thr Trp Ile Arg>

6150          6160          6170          6180          6190
                *       *       *       *       *       *       *       *       *       *
          ACT GGA AGC CCC AAG TGC TCT CCT TCA GAC CTA GAT TAC CTA AAA ATA
          Thr Gly Ser Pro Lys Cys Ser Pro Ser Asp Leu Asp Tyr Leu Lys Ile>

6200          6210          6220          6230          6240
                *       *       *       *       *       *       *       *       *       *
          AGT TTC ACT GAG AAA GGA AAA CAA GAA AAT ATC CTA AAA TGG GTA AAT
          Ser Phe Thr Glu Lys Gly Lys Gln Glu Asn Ile Leu Lys Trp Val Asn>

6250          6260          6270          6280
                        *       *       *       *       *       *       *       *       *
          GGT ATG TCT TGG GGA ATG GTA TAT TAT GGA GGC TCG GGT AAA CAA CCA
          Gly Met Ser Trp Gly Met Val Tyr Tyr Gly Gly Ser Gly Lys Gln Pro>

6290          6300          6310          6320          6330
            *       *       *       *       *       *       *       *       *       *
          GGC TCC ATT CTA ACT ATT CGC CTC AAA ATA AAC CAG CTG GAG CCT CCA
          Gly Ser Ile Leu Thr Ile Arg Leu Lys Ile Asn Gln Leu Glu Pro Pro>

6340          6350          6360          6370          6380
                *       *       *       *       *       *       *       *       *
          ATG GCT ATA GGA CCA AAT ACG GTC TTG ACG GGT CAA AGA CCC CCA ACC
          Met Ala Ile Gly Pro Asn Thr Val Leu Thr Gly Gln Arg Pro Pro Thr>

6390          6400          6410          6420          6430
                *       *       *       *       *       *       *       *       *       *
          CAA GGA CCA GGA CCA TCC TCT AAC ATA ACT TCT GGA TCA GAC CCC ACT
          Gln Gly Pro Gly Pro Ser Ser Asn Ile Thr Ser Gly Ser Asp Pro Thr>
```

FIGURE 3, CONT.

(SEQ ID NO: 3) cont'd

```
              6440          6450          6460          6470          6480
                *       *     *       *     *       *     *       *     *
            GAG TCT AAC AGC ACG ACT AAA ATG GGG GCA AAA CTT TTT AGC CTC ATC
            Glu Ser Asn Ser Thr Thr Lys Met Gly Ala Lys Leu Phe Ser Leu Ile>

6490          6500          6510          6520
                *       *     *       *     *       *     *       *     *
            CAG GGA GCT TTT CAA GCT CTT AAC TCC ACG ACT CCA GAG GCT ACC TCT
            Gln Gly Ala Phe Gln Ala Leu Asn Ser Thr Thr Pro Glu Ala Thr Ser>

6530          6540          6550          6560          6570
      *       *     *       *     *       *     *       *     *       *
    TCT TGT TGG CTA TGC TTA GCT TCG GGC CCA CCT TAC TAT GAA GGA ATG
    Ser Cys Trp Leu Cys Leu Ala Ser Gly Pro Pro Tyr Tyr Glu Gly Met>

6580          6590          6600          6610          6620
                *       *     *       *     *       *     *       *     *
            GCT AGA AGA GGG AAA TTC AAT GTG ACA AAA GAA CAT AGA GAC CAA TGC
            Ala Arg Arg Gly Lys Phe Asn Val Thr Lys Glu His Arg Asp Gln Cys>

6630          6640          6650          6660          6670
                   *       *     *       *     *       *     *       *     *
            ACA TGG GGA TCC CAA AAT AAG CTT ACC CTT ACT GAG GTT TCT GGA AAA
            Thr Trp Gly Ser Gln Asn Lys Leu Thr Leu Thr Glu Val Ser Gly Lys>

6680          6690          6700          6710          6720
                *       *     *       *     *       *     *       *     *
            GGC ACC TGC ATA GGA AAG GTT CCC CCA TCC CAC CAA CAC CTT TGT AAC
            Gly Thr Cys Ile Gly Lys Val Pro Pro Ser His Gln His Leu Cys Asn>

6730          6740          6750          6760
                   *     *       *     *       *     *       *     *
            CAC ACT GAA GCC TTT AAT CAA ACC TCT GAG AGT CAA TAT CTG GTA CCT
            His Thr Glu Ala Phe Asn Gln Thr Ser Glu Ser Gln Tyr Leu Val Pro>

6770          6780          6790          6800          6810
      *       *     *       *     *       *     *       *     *       *
    GGT TAT GAC AGG TGG TGG GCA TGT AAT ACT GGA TTA ACC CCT TGT GTT
    Gly Tyr Asp Arg Trp Trp Ala Cys Asn Thr Gly Leu Thr Pro Cys Val>

6820          6830          6840          6850          6860
      *       *     *       *     *       *     *       *     *
    TCC ACC TTG GTT TTT AAC CAA ACT AAA GAT TTT TGC ATT ATG GTC AAA
    Ser Thr Leu Val Phe Asn Gln Thr Lys Asp Phe Cys Ile Met Val Gln>

6870          6880          6890          6900          6910
           *     *       *     *       *     *       *     *       *
    ATT GTT CCC CGA GTG TAT TAC TAT CCC GAA AAA GCA ATC CTT GAT GAA
    Ile Val Pro Arg Val Tyr Tyr Tyr Pro Glu Lys Ala Ile Leu Asp Glu>

6920          6930          6940          6950          6960
                *       *     *       *     *       *     *       *     *
            TAT GAC TAC AGA AAT CAT CGA CAA AAG AGA GAA CCC ATA TCT CTG ACA
            Tyr Asp Tyr Arg Asn His Arg Gln Lys Arg Glu Pro Ile Ser Leu Thr>

6970          6980          6990          7000
                   *     *       *     *       *     *       *     *
            CTT GCT GTG ATG CTC GGA CTT GGA GTG GCA GCA GGT GTA GGA ACA GGA
            Leu Ala Val Met Leu Gly Leu Gly Val Ala Ala Gly Val Gly Thr Gly>
```

FIGURE 3, CONT.

(SEQ ID NO: 3) cont'd

```
      7010        7020        7030        7040        7050
        *     *     *     *     *     *     *     *     *     *
      ACA GCT GCC CTG GTC ACG GGA CCA CAG CAG CTA GAA ACA GGA CTT AGT
      Thr Ala Ala Leu Val Thr Gly Pro Gln Gln Leu Glu Thr Gly Leu Ser>

7060        7070        7080        7090        7100
           *     *     *     *     *     *     *     *     *
         AAC CTA CAT CGA ATT GTA ACA GAA GAT CTC CAA GCC CTA GAA AAA TCT
         Asn Leu His Arg Ile Val Thr Glu Asp Leu Gln Ala Leu Glu Lys Ser>

7110        7120        7130        7140        7150
              *     *     *     *     *     *     *     *     *     *
            GTC AGT AAC CTG GAG GAA TCC CTA ACC TCC TTA TCT GAA GTA GTC CTA
            Val Ser Asn Leu Glu Glu Ser Leu Thr Ser Leu Ser Glu Val Val Leu>

7160        7170        7180        7190        7200
                 *     *     *     *     *     *     *     *     *     *
               CAG AAT AGA AGA GGG TTA GAT TTA TTA TTT CTA AAA GAA GGA GGA TTA
               Gln Asn Arg Arg Gly Leu Asp Leu Leu Phe Leu Lys Glu Gly Gly Leu>

7210        7220        7230        7240
                    *     *     *     *     *     *     *     *     *
                  TGT GTA GCC TTG AAG GAG GAA TGC TGT TTT TAT GTG GAT CAT TCA GGG
                  Cys Val Ala Leu Lys Glu Glu Cys Cys Phe Tyr Val Asp His Ser Gly>

7250        7260        7270        7280        7290
        *     *     *     *     *     *     *     *     *     *
      GCC ATC AGA GAC TCC ATG AAC AAG CTT AGA GAA AGG TTG GAC AAG CGT
      Ala Ile Arg Asp Ser Met Asn Lys Leu Arg Glu Arg Leu Glu Lys Arg>

7300        7310        7320        7330        7340
           *     *     *     *     *     *     *     *     *
         CGA AGG GAA AAG GAA ACT ACT CAA GGG TGG TTT GAG GGA TGG TTC AAC
         Arg Arg Glu Lys Glu Thr Thr Gln Gly Trp Phe Glu Gly Trp Phe Asn>

7350        7360        7370        7380        7390
              *     *     *     *     *     *     *     *     *     *
            AGG TCT CTT TGG TTG GCT ACC CTA CTT TCT GCT TTA ACA GGA CCC TTA
            Arg Ser Leu Trp Leu Ala Thr Leu Leu Ser Ala Leu Thr Gly Pro Leu>

7400        7410        7420        7430        7440
                 *     *     *     *     *     *     *     *     *     *
               ATA GTC CTC CTC CTG TTA CTC ACA GTT GGG CCA TGT ATT ATT AAC AAG
               Ile Val Leu Leu Leu Leu Leu Thr Val Gly Pro Cys Ile Ile Asn Lys>

7450        7460        7470        7480
                    *     *     *     *     *     *     *     *     *
                  TTA ATT GCC TTC ATT AGA GAA CGA ATA AGT GCA GTC CAG ATC ATG GTA
                  Leu Ile Ala Phe Ile Arg Glu Arg Ile Ser Ala Val Gln Ile Met Val>

7490        7500        7510        7520        7530
        *     *     *     *     *     *     *     *     *
      CTT AGA CAA CAG TAC CAA AGC CCG TCT AGC AGG GAA GCT GGC CGC
      Leu Arg Gln Gln Tyr Gln Ser Pro Ser Ser Arg Glu Ala Gly Arg>

7540        7550        7560        7570        7580        7590
           *     *     *     *     *     *     *     *     *     *     *     *
         TAGCTCT ACCAGTTCTA AGATTAGAAC TATTAACAAG AGAAGAAGTG GGGAATGAAA
```

FIGURE 3, CONT.

```
          7600       7610       7620       7630       7640       7650     (SEQ ID NO: 3) cont'd
           *   *      *   *      *   *      *   *      *   *      *   *
       GGATGAAAAT ACAACCTAAG CTAATGAGAA GCTTAAAATT GTTCTGAATT CCAGAGTTTG 7660       7670       7680       7690       7700       7710
           *   *      *   *      *   *      *   *      *   *      *   *
       TTCCTTATAG GTAAAAGATT AGGTTTTTTG CTGTTTTAAA ATATGCGGAA GTAAAATAGG 7720       7730       7740       7750       7760       7770
           *   *      *   *      *   *      *   *      *   *      *   *
       CCCTGAGTAC ATGTCTCTAG GCATGAAACT TCTTGAAACT ATTTGAGATA ACAAGAAAAG 7780       7790       7800       7810       7820       7830
           *   *      *   *      *   *      *   *      *   *      *   *
       GGAGTTTCTA ACTGCTTGTT TAGCTTCTGT AAAACTGGTT GCGCCATAAA GATGTTGAAA 7840       7850       7860       7870       7880       7890
           *   *      *   *      *   *      *   *      *   *      *   *
       TGTTGATACA CATATCTTGG TGACAACATG TCTCCCCCAC CCCGAAACAT GCGCAAATGT 7900       7910       7920       7930       7940       7950
           *   *      *   *      *   *      *   *      *   *      *   *
       GTAACTCTAA AACAATTTAA ATTAATTGGT CCACGAAGCG CGGGCTCTCG AAGTTTTAAA 7960       7970       7980       7990       8000       8010
           *   *      *   *      *   *      *   *      *   *      *   *
       TTGACTGGTT TGTGATATTT TGAAATGATT GGTTTGTAAA GCGCGGGCTT TGTTGTGAAC 8020       8030       8040       8050       8060       8070
           *   *      *   *      *   *      *   *      *   *      *   *
       CCCATAAAAG CTGTCCCGAC TCCACACTCG GGGCCGCAGT CCTCTACCCC TGCGTGGTGT 8080       8090       8100       8110       8120       8130
           *   *      *   *      *   *      *   *      *   *      *   *
       ACGACTGTGG GCCCCAGCGC GCTTGGAATA AAAATCCTCT TGCTGTTTGC ATCAAAAAAA
       AA
```

MOLECULAR SEQUENCE OF SWINE RETROVIRUS

CROSS-REFERENCE TO RELATED APPLICATIONS

This application is a divisional of U.S. patent application Ser. No. 08/766,528, filed on Dec. 13, 1996 now U.S. Pat. No. 6,190,861, which is a continuation part of U.S. patent application Ser. No. 08/572,645, filed on Dec. 14, 1995 now abandoned, both of which applications are hereby incorporated by reference.

FIELD OF THE INVENTION

The invention relates to porcine retroviral sequences, peptides encoded by porcine retroviral sequences, and methods of using the porcine retroviral nucleic acids and peptides.

BACKGROUND OF THE INVENTION

Advances in solid organ transplantation and a chronic shortage of suitable organ donors have made xenotransplantation an attractive alternative to the use of human allografts. However, the potential for introduction of a new group of infectious diseases from donor animals into the human population is a concern with the use of these methods.

The term applied to the natural acquisition by humans of infectious agents carried by other species is zoonosis. The transplantation of infection from nonhuman species into humans is best termed "direct zoonosis" or "xenosis."

Nonhuman primates and swine have been considered the main potential sources of organs for xenotransplantation (Niekrasz et al.,(1992) *Transplant Proc* 24:625; Starzl et al. (1993) *Lancet* 341:65; Murphy et al. (1970) *Trans Proc* 4:546; Brede and Murphy (1972) *Primates Med* 7:18; Cooper et al. In *Xenotransplantation: The Transplantation of Organs and Tissues between Species*, eds. Cooper et al. (1991) p. 457; R Y Calne (1970) *Transplant Proc* 2:550; H. Auchincloss, Jr. (1988) *Transplantation* 46:1; and Chiche et al. (1993) *Transplantation* 6:1418). The infectious disease issues for primates and swine are similar to those of human donors. The prevention of infection depends on the ability to predict, to recognize, and to prevent common infections in the immunocompromised transplantation recipient (Rubin et al. (1993) *Antimicrob Agents Chemother* 37:619). Because of the potential carriage by nonhuman primates of pathogens easily adopted to humans, ethical concerns, and the cost of maintaining large colonies of primates, other species have received consideration as organ donors (Brede and Murphy (1972) *Primates Med* 7:18; Van Der Riet et al. (1987) *Transplant Proc* 19:4069; Katler In *Xenotransplantation: The Transplantation of Organs and Tissues between Species*, eds. Cooper et al. (1991) p. 457; Metzger et al. (1981) *J Immunol* 127:769; McClure et al. (1987) *Nature* 330:487; Letvin et al. (1987) *J Infect Dis* 156:406; Castro et al. (1991) *Virology* 184:219; Benveniste and Todaro (1973) *Proc Natl Acad Sci USA* 70:3316; and Teich, in *RNA Tumor viruses*, eds. Weiss et. al. (1985) p. 25) The economic importance of swine and experience in studies of transplantation in the miniature swine model have allowed some of the potential pathogens associated with these animals to be defined (Niekrasz et al. (1992) *Transplant Proc* 24:625; Cooper et al. In *Xenotransplantation: The Transplantation of Organs and Tissues between Species*, eds. Cooper et al. (1991) 457; and Leman et al. (1992) *Diseases of Swine*, 7th ed. Ames, Iowa:Iowa State University). Miniature swine have received consideration as organ donors because of a number of features of the species. The structure and function of the main pig organs are comparable to those of man. Swine attain body weights and organ sizes adequate to the provision of organs for human use. Lastly, veterinarians and commercial breeders have developed approaches to creation of specific-pathogen-free (SPF) swine with the ability to eliminate known pathogens from breeding colonies (Alexander et al. (1980) *Proc 6th Int Congr Pig Vet Soc*, Copenhagen; Betts (1961) *Vet Rec* 73:1349; Betts et al. (1960) *Vet Rec* 72:461; Caldwell et al. (1959) *J Am Vet Med Assoc* 135:504; and Yong (1964) *Adv Vet Sci* 9:61).

Concern exists over the transfer of porcine retroviruses by xenotransplantation (Smith (1993) *N Engl J Med* 328:141). Many of the unique properties of the retroviruses are due to the synthesis of a complementary DNA copy from the RNA template (by reverse transcriptase), and integration of this DNA into the host genome. The integrated retroviral copy (which is referred to as an endogenous copy or "provirus") can be transmitted via the germ line.

SUMMARY OF THE INVENTION

In general, the invention features a purified swine or miniature swine retroviral nucleic acid, e.g., a Tsukuba nucleic acid, a purified miniature swine retroviral nucleic acid sequence of SEQ ID NO:1 or its complement, SEQ ID NO:2 or its complement, or SEQ ID NO:3 or its complement, and methods of their use in detecting the presence of porcine, e.g., miniature swine, retroviral sequences.

In another aspect, the invention features a purified nucleic acid, e.g., a probe or primer, which can specifically hybridize with a purified swine or miniature swine retroviral genome, e.g., a Tsukuba genome, the sequence of SEQ ID NO:1 or its complement, SEQ ID NO:2 or its complement, or SEQ ID NO:3 or its complement.

In preferred embodiments the nucleic acid is other than the entire retroviral genome of SEQ ID NO:1 or its complement, SEQ ID NO:2 or its complement, or SEQ ID NO:3 or its complement, e.g., it is at least 1 nucleotide longer, or at least 1 nucleotide shorter, or differs in sequence at at least one position, e.g., the nucleic acid is a fragment of the sequence of SEQ ID NO:1 or its complement SEQ ID NO:2 or its complement, or SEQ ID NO:3 or its complement, or it includes sequence additional to that of SEQ ID NO:1, or its complement, SEQ ID NO:2 or its complement, or SEQ ID NO:3 or its complement.

In preferred embodiments, the nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other embodiments: the sequence of the nucleic acid differs from the corresponding sequence of SEQ ID NO: 1 or its complement, SEQ ID NO:2 or its complement, or SEQ ID NO:3 or its complement, by 1, 2, 3, 4, or 5 base pairs; the sequence of the nucleic acid differs from the corresponding sequence of SEQ ID NO: 1 or its complement, SEQ ID NO:2 or its complement, or SEQ ID NO:3 or its complement, by at least 1, 2, 3, 4, or 5 base pairs but less than 6, 7, 8, 9, or 10 base pairs.

In other preferred embodiments: the nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length.

In yet other preferred embodiments: the nucleic acid can specifically hybridize with a translatable region of a miniature swine retroviral genome, e.g., the retroviral genome of SEQ ID NO: 1, or its complement, SEQ ID NO:2 or its complement, or SEQ ID NO:3 or its complement, e.g., a region from the gag, pol, or env gene; the probe or primer can specifically hybridize with an untranslated region of a miniature swine retroviral genome, e.g., the retroviral genome of SEQ ID NO: 1, or its complement SEQ ID NO:2 or its complement, or SEQ ID NO:3 or its complement; the probe or primer can specifically hybridize with a non-conserved region of a miniature swine retroviral genome, e.g., the retroviral genome of SEQ ID NO: 1, or its complement, SEQ ID NO:2 or its complement, or SEQ ID NO:3 or its complement; the probe or primer can specifically hybridize with the highly conserved regions of a miniature swine retroviral genome, e.g., the retroviral genome of SEQ ID NO: 1, or its complement, SEQ ID NO:2 or its complement, or SEQ ID NO:3 or its complement.

In preferred embodiments, the primer is selected from the group consisting of SEQ ID NOs:4–74.

In preferred embodiments, hybridization of the probe to retroviral sequences can be detected by standard methods, e.g., by radiolabeled probes or by probes bearing nonradioactive markers such as enzymes or antibody binding sites. For example, a probe can be conjugated with an enzyme such as horseradish peroxidase, where the enzymatic activity of the conjugated enzyme is used as a signal for hybridization. Alternatively, the probe can be coupled to an epitope recognized by an antibody, e.g., an antibody conjugated to an enzyme or another marker.

In another aspect, the invention features a reaction mixture which includes a target nucleic acid, e.g., a human, swine or a miniature swine nucleic acid, and a purified second nucleic acid, e.g., a probe or primer, as, e.g., is described herein, which specifically hybridizes with the sequence of SEQ ID NO:1 or its complement, SEQ ID NO:2 or its complement, or SEQ ID NO:3 or its complement, a swine or a miniature swine retroviral nucleic acid, e.g., a Tsukuba nucleic acid.

In preferred embodiments, the target nucleic acid includes RNA; or includes DNA.

In preferred embodiments, the target nucleic acid includes: genomic DNA isolated from a miniature swine; RNA or cDNA, e.g., cDNA made from an RNA template, isolated from a miniature swine; DNA, RNA or cDNA, e.g., cDNA made from an RNA template, isolated from a miniature swine organ, e.g., a kidney; RNA, DNA or cDNA, e.g., cDNA made from an RNA template, isolated from a miniature swine potential donor organ; RNA, DNA or cDNA, e.g., cDNA made from an RNA template, isolated from a miniature swine organ which has been transplanted into a organ recipient, e.g., a xenogeneic recipient, e.g., a primate, e.g., a human.

In preferred embodiments, the target nucleic acid includes: genomic DNA isolated from a swine; RNA or cDNA, e.g., cDNA made from an RNA template, isolated from a swine; DNA, RNA or cDNA, e.g., cDNA made from an RNA template, isolated from a swine organ, e.g., a kidney; RNA, DNA or cDNA, e.g., cDNA made from an RNA template, isolated from a swine potential donor organ; RNA, DNA or cDNA, e.g., cDNA made from an RNA template, isolated from a swine organ which has been transplanted into a organ recipient, e.g., a xenogeneic recipient, e.g., a primate, e.g., a human.

In a preferred embodiment: the second nucleic acid is a porcine retroviral sequence, probe or primer, e.g., as described herein, e.g., a Tsukuba-1 retroviral sequence the second nucleic acid is a sequence of SEQ ID NO:1 or its complement, SEQ ID NO:2 or its complement, or SEQ ID NO:3 or its complement, or a fragment of the sequence or complement at least 10, 20, or 30, basepairs in length.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In preferred embodiments the second nucleic acid is: a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof;

a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants hereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof.

In another aspect, the invention features a method for screening a cell or a tissue, e.g., a cellular or tissue transplant, e.g., a xenograft, for the presence or expression of a swine or a miniature swine retrovirus or retroviral sequence, e.g., an endogenous miniature swine retrovirus. The method includes:

contacting a target nucleic acid from the tissue with a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID.NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof, a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid under conditions in which hybridization can occur, hybridization being indicative of the presence or expression of an endogenous miniature swine retrovirus or retroviral sequence in the tissue or an endogenous swine retrovirus in the tissue.

In preferred embodiments, the method further includes amplifying the target nucleic acid with primers which specifically hybridize to the sequence of SEQ ID NO:1 or its complement, SEQ ID NO:2 or its complement, or SEQ ID NO:3 or its complement.

In preferred embodiments, the tissue or cellular transplant is selected from the group consisting of: heart, lung, liver, bone marrow, kidney, brain cells, neural tissue, pancreas or pancreatic cells, thymus, or intestinal tissue.

In other preferred embodiments, the target nucleic acid is: DNA; RNA; or cDNA.

In other preferred embodiments, the target nucleic acid is taken from: a tissue sample, or a blood sample, e.g., a tissue biopsy sample, e.g., a tissue sample suitable for in situ hybridization or immunohistochemistry.

In preferred embodiments, the target nucleic acid includes: genomic DNA isolated from a miniature swine; RNA or cDNA, e.g., cDNA made from an RNA template, isolated from a miniature swine; DNA, RNA or cDNA, e.g., cDNA made from an RNA template, isolated from a miniature swine organ, e.g., a kidney; RNA, DNA or cDNA, e.g., cDNA made from an RNA template, isolated from a miniature swine potential donor organ; RNA, DNA or cDNA, e.g., cDNA made from an RNA template, isolated from a miniature swine organ which has been transplanted into a organ recipient, e.g., a xenogeneic recipient, e.g., a primate, e.g., a human.

In preferred embodiments, the target nucleic acid includes: genomic DNA isolated from a swine; RNA or cDNA, e.g., cDNA made from an RNA template, isolated from a swine; DNA, RNA or cDNA, e.g., cDNA made from an RNA template, isolated from a swine organ, e.g., a kidney; RNA, DNA or cDNA, e.g., cDNA made from an RNA template, isolated from a swine potential donor organ; RNA, DNA or cDNA, e.g., cDNA made from an RNA template, isolated from a swine organ which has been transplanted into a organ recipient, e.g., a recipient swine or a xenogeneic recipient, e.g., a primate, e.g., a human.

In a preferred embodiment the target nucleic acid is RNA, or a nucleic acid amplified from RNA in the tissue, and hybridization is correlated with expression of an endogenous miniature swine retrovirus or retroviral sequence or an endogenous swine retrovirus.

In a preferred embodiment the target nucleic acid is DNA, or a nucleic acid amplified from DNA in the tissue, and hybridization is correlated with the presence of an endogenous miniature swine retrovirus or an endogenous swine retrovirus.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a method of screening a porcine derived cell or tissue for the presence of an activatable porcine retrovirus, e.g., an activatable porcine provirus. The method includes:

stimulating a porcine derived cell or tissue with a treatment which can activate a retrovirus;

contacting a target nucleic acid from the porcine derived cell or tissue with a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g. from nucleotides 3112–4683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g; from nucleotides 86–1999) of SEQ ID NO:1, nucleotides 4738–6722 (e.g. from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid hybridization being indicative of the presence of an activatable porcine provirus in the porcine derived cell or tissue.

In preferred embodiments the treatment is: contact with a drug, e.g., a steroid or a cytotoxic agent, infection or contact with a virus, the induction of stress, e.g., nutritional stress or immunologic stress, e.g., contact with a T-cell, e.g., a reactive T-cell.

In preferred embodiments, the method further includes amplifying the target nucleic acid with primers which specifically hybridize to the sequence of SEQ ID NO:1 or its complement, SEQ ID NO:2 or its complement, or SEQ ID NO:3 or its complement.

In other preferred embodiments, the target nucleic acid is taken from: a tissue sample, or a blood sample, e.g., a tissue biopsy sample, e.g., a tissue sample suitable for in situ hybridization or immunohistochemistry.

In preferred embodiments, the target nucleic acid includes: genomic DNA isolated from a miniature swine; RNA or cDNA, e.g., cDNA made from an RNA template, isolated from a miniature swine; DNA, RNA or cDNA, e.g., cDNA made from an RNA template, isolated from a miniature swine organ, e.g., a kidney; RNA, DNA or cDNA, e.g., cDNA made from an RNA template, isolated from a miniature swine potential donor organ; RNA, DNA or cDNA, e.g., cDNA made from an RNA template, isolated from a miniature swine organ which has been transplanted into a organ recipient, e.g., a xenogeneic recipient, e.g., a primate, e.g., a human.

In preferred embodiments, the target nucleic acid includes: genomic DNA isolated from a swine; RNA or cDNA, e.g., cDNA made from an RNA template, isolated from a swine; DNA, RNA or cDNA, e.g., cDNA made from an RNA template, isolated from a swine organ, e.g., a kidney; RNA, DNA or cDNA, e.g., cDNA made from an RNA template, isolated from a swine potential donor organ; RNA, DNA or cDNA, e.g., cDNA made from an RNA template, isolated from a swine organ which has been transplanted into a organ recipient, e.g., a recipient swine or a xenogeneic recipient, e.g., a primate, e.g., a human.

In preferred embodiments, the second nucleic acid has at least 60%, 70%, 72%, more preferably at least 85%, more preferably at least 90%; more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a method for screening a miniature swine genome or a swine genome for the presence of a porcine retrovirus or retroviral sequence, e.g., an endogenous porcine retrovirus. The method includes:

contacting the miniature swine (or swine) genomic DNA with a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g., from nucleotides 3112–4683) of SEQ ID NO:1, nucleotides 598–2169 (e.g., from nucleotides 598–2169) of SEQ ID NO:2, or nucleotides 585–2156 (e.g, from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g., from nucleotides 86–1999) of SEQ ID NO:1, nucleotides 4738–6722 (e.g., from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid under conditions in which the sequences can hybridize, hybridization being indicative of the presence of the endogenous porcine retrovirus or retroviral sequence in the miniature swine (or swine) genome.

In preferred embodiments, the method further includes amplifying all or a portion of the miniature swine (or swine) genome with primers which specifically hybridize to the sequence of SEQ ID NO:1 or its complement, SEQ ID NO:2 or its complement, or SEQ ID NO:3 or its complement.

In a preferred embodiment: the second nucleic acid is a porcine retroviral sequence, probe or primer, e.g., as described herein, e.g., a Tsukuba-1 retroviral sequence; the second nucleic acid is a sequence of SEQ ID NO:1 or its complement, SEQ ID NO:2 or its complement, or SEQ ID NO:3 or its complement, or a fragment of the sequence or complement at least 10, 20, or 30, basepairs in length.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at,least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a method for screening a genetically modified miniature swine or a genetically modified swine for the presence or expression of a miniature swine or swine retrovirus or retroviral sequence, e.g., an endogenous miniature swine retrovirus. The method includes:

contacting a target nucleic acid from the genetically modified miniature swine or swine with a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof;

a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid under conditions in which hybridization can occur, hybridization being indicative of the presence or expression of an endogenous miniature swine retrovirus or retroviral sequence or swine retrovirus or retroviral sequence in the genetically modified miniature swine or swine.

In preferred embodiments, the method further includes amplifying the target nucleic acid with primers which specifically hybridize to the sequence of SEQ ID NO:1 or its complement, SEQ ID NO:2 or its complement, or SEQ ID NO:3 or its complement.

In preferred embodiments, the target nucleic acid includes: genomic DNA isolated from a miniature swine; RNA or cDNA, e.g., cDNA made from an RNA template, isolated from a miniature swine; DNA, RNA or cDNA, e.g., cDNA made from an RNA template, isolated from a miniature swine organ, e.g., a kidney; RNA, DNA or cDNA, e.g., cDNA made from an RNA template, isolated from a miniature swine potential donor organ; RNA, DNA or cDNA, e.g., cDNA made from an RNA template, isolated from a miniature swine organ which has been transplanted into a organ recipient, e.g., a xenogeneic recipient, e.g., a primate, e.g., a human.

In preferred embodiments, the target nucleic acid includes: genomic DNA isolated from a swine; RNA or cDNA, e.g., cDNA made from an RNA template, isolated from a swine; DNA, RNA or cDNA, e.g., cDNA made from an RNA template, isolated from a swine organ, e.g., a kidney; RNA, DNA or cDNA, e.g., cDNA made from an RNA template, isolated from a swine potential donor organ; RNA, DNA or cDNA, e.g., cDNA made from an RNA template, isolated from a swine organ which has been transplanted into a organ recipient, e.g., a recipient swine or a xenogeneic recipient, e.g., a primate, e.g., a human.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a method of assessing the potential risk associated with the transplantation of a graft from a donor miniature swine or swine into a recipient animal, e.g., a miniature swine or swine, a non-human primate, or a human. The method includes:

contacting a target nucleic acid from the donor, recipient or the graft, with a second sequence chosen from the group of: a nucleic acid sequence which specifically hybridizes a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof;

a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof;

a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid under conditions in which the sequences can hybridize, hybridization being indicative of a risk associated with the transplantation.

In a preferred embodiment: the second nucleic acid is a Tsukuba-1 retroviral sequence, probe or primer, e.g., as described herein; the second nucleic acid is a porcine retroviral sequence, probe or primer, e.g., as described herein; the second nucleic acid is the sequence of SEQ ID NO:1 or its complement, SEQ ID NO:2 or its complement, or SEQ ID NO:3 or its complement, or a fragment of the sequence or complement at least 10, 20, or 30, basepairs in length.

In preferred embodiments, the target nucleic acid includes: genomic DNA isolated from a miniature swine; RNA or cDNA, e.g., cDNA made from an RNA template, isolated from a miniature swine; DNA, RNA or cDNA, e.g., cDNA made from an RNA template, isolated from a miniature swine organ, e.g., a kidney; RNA, DNA or cDNA, e.g., cDNA made from an RNA template, isolated from a miniature swine potential donor organ; RNA, DNA or cDNA, e.g., cDNA made from an RNA template, isolated from a miniature swine organ which has been transplanted into a organ recipient, e.g.,a xenogeneic recipient, e.g., a primate, e.g., a human.

In preferred embodiments, the target nucleic acid includes: genomic DNA isolated from a swine; RNA or cDNA, e.g., cDNA made from an RNA template, isolated from a swine; DNA, RNA or cDNA, e.g., cDNA made from an RNA template, isolated from a swine organ, e.g., a kidney; RNA, DNA or cDNA, e.g., cDNA made from an RNA template, isolated from a swine potential donor organ; RNA, DNA or cDNA, e.g., cDNA made from an RNA template, isolated from a swine organ which has been transplanted into a organ recipient, e.g., a recipient swine or a xenogeneic recipient, e.g., a primate, e.g., a human.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a method of determining if an endogenous miniature swine or swine retrovirus or retroviral sequence genome includes a mutation which modulates its expression, e.g., results in misexpression. The method includes:

determining the structure of the endogenous retroviral genome, and comparing the structure of the endogenous retroviral genome with the retroviral sequence of SEQ ID NO:1 or its complement, SEQ ID NO:2 or its complement, or SEQ ID NO:3 or its complement, a difference being predictive of a mutation.

In preferred embodiments the method includes sequencing the endogenous genome and comparing it with a sequence from SEQ ID NO:1 or its complement, SEQ ID NO:2 or its complement, or SEQ ID NO:3 or its complement.

In preferred embodiments, the method includes using primers to amplify, e.g., by PCR, LCR (ligase chain reaction), or other amplification methods, a region of the endogenous retroviral genome, and comparing the structure of the amplification product to he sequence of SEQ ID NO:1 or its complement, SEQ ID NO:2 or its complement, or SEQ ID NO:3 or its complement to determine if there is difference in sequence between retroviral genome and SEQ ID NO:1 or its complement, SEQ ID NO:2 or its complement, or SEQ ID NO:3 or its complement. The method further includes determining if one or more restriction sites exist in the endogenous retroviral genome, and determining if the sites exist in SEQ ID NO:1 or its complement, SEQ ID NO:2 or its complement, or SEQ ID NO:3 or its complement.

In preferred embodiments, the mutation is a gross defect, e.g., an insertion, inversion, translocation or a deletion, of all or part of the retroviral genome.

In preferred embodiments, detecting the mutation can include: (i) providing a labeled PCR probe amplified from DNA (e.g., SEQ ID NO: 1, SEQ ID NO: 2, or SEQ ID NO: 3) containing a porcine retroviral nucleotide sequence which hybridizes to a sense or antisense sequence from the porcine retroviral genome (e.g., SEQ ID NO: 1, SEQ ID NO: 2, or SEQ ID NO: 3), or naturally occurring mutants thereof; (ii) exposing the probe/primer to nucleic acid of the tissue (e.g., genomic DNA) digested with a restriction endonuclease; and (iii) detecting by in situ hybridization of the probe/primer to the nucleic acid, the presence or absence of the genetic lesion. Alternatively, direct PCR analysis, using primers specific for porcine retroviral genes (e.g., genes comprising the nucleotide sequence shown in SEQ ID NO: 1, SEQ ID NO: 2, or SEQ ID NO: 3), can be used to detect the presence or absence of the genetic lesion in the porcine retroviral genome by comparing the products amplified.

In another aspect, the invention features a method of providing a miniature swine or a swine free of an endogenous retrovirus or retroviral sequence, e.g., activatable retrovirus, insertion at a preselected site. The method includes:

performing a breeding cross between a first miniature swine (or swine) having a retroviral insertion at the preselected site and a second miniature swine (or swine) not having a retroviral insertion at a preselected site, e.g., the same site, and recovering a progeny miniature swine (or swine), not having the insertion, wherein the presence or absence of the retroviral insertion is determined by contacting the genome of a miniature swine(or swine) with a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof;

a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid.

In preferred embodiments, the nucleic acid is hybridized to nucleic acid, e.g., DNA from the genome, of the first animal or one of its ancestors.

In preferred embodiments, the nucleic acid is hybridized to nucleic acid, e.g., DNA from the genome, of the second animal or one of its ancestors.

In preferred embodiments, the nucleic acid is hybridized to nucleic acid, e.g., DNA from the genome, of the progeny animal or one of its descendants.

In preferred embodiments, the nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the nucleic acid is a full length retroviral genome.

In another aspect, the invention features a method of evaluating a treatment, e.g., an immunosuppressive treatment, for the ability to activate a retrovirus, e.g., an endogenous porcine retrovirus. The method includes:

administering a treatment to a subject, e.g., a miniature swine (or a swine), having an endogenous porcine retrovirus; and detecting expression of the porcine retrovirus with a purified nucleic acid sequence which specifically hybridizes to the sequence of SEQ ID NO:1 or its complement, SEQ ID NO:2 or its complement, or SEQ ID NO:3 or its complement.

In preferred embodiments, the immunosuppresive treatment includes radiation, chemotherapy or drug treatment.

In preferred embodiments: the treatment is one which can induce immunological tolerance; the treatment is one which can introduce new genetic material, e.g., introduce new genetic material into a miniature swine genome (or a swine genome) or into the genome of a host which receives a swine or a miniature swine graft, e.g., the treatment is one which introduces a new genetic material via retroviral mediated transfer.

In a preferred embodiment: the purified nucleic acid is a Tsukuba-1 retroviral sequence, probe or primer, e.g., as described herein; the purified nucleic acid is a porcine: retroviral sequence, probe or primer, e.g., as described herein; the purified nucleic acid is the sequence of SEQ ID NO:1 or its complement, SEQ ID NO:2 or its complement, or SEQ ID NO:3 or its complement, or a fragment of such sequence or complement at least 10, 20, or 30, basepairs in length.

In preferred embodiments, the purified nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the purified nucleic acid is at least 10, more preferably at least 15, more preferably at least 20, most preferably at least 25, 30, 50, 100. 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the purified nucleic acid is a full length retroviral genome.

In preferred embodiments the second nucleic acid is: a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g., from nucleotides 598–2169) of SEQ ID NO:2, or nucleotides 585–2156 (e.g., from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof.

In another aspect, the invention features a method of localizing the origin of a porcine retroviral infection. The method includes:

contacting a target nucleic acid from the graft with a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g., from nucleotides 3112–4683) of SEQ ID NO:1, nucleotides 598–2169 (e.g, from nucleotides 598–10 2169) of SEQ ID NO:2, or nucleotides 585–2156 (e.g, from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof;

a nucleic acid of at least 10 consecutive nucleotides of sense or antisense sequence which encodes a env protein; a nucleic acid of at least 10 consecutive nucleotides of sense or antisense sequence from nucleotides 2–1999 (e.g., from nucleotides 86–1999) of SEQ ID NO:1, nucleotides 4738–6722 (e.g., from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid contacting a target nucleic acid from the recipient with a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g. from nucleotides 31124683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid; hybridization to the nucleic acid from the graft correlates with the porcine retroviral infection in the graft; and hybridization to the nucleic acid from the recipient correlates with the porcine retroviral infection in the recipient.

In preferred embodiments, the target nucleic acid includes: genomic DNA, RNA or cDNA, e.g., cDNA made from an RNA template.

In a preferred embodiment: the second nucleic acid is a porcine retroviral sequence, probe or primer, e.g., as described herein, e.g., a Tsukuba-1 retroviral sequence; the second nucleic acid is a sequence of SEQ ID NO:1 or its complement, SEQ ID NO:2 or its complement, or SEQ ID NO:3 or its complement, or a fragment of the sequence or complement at least 10, 20, or 30, basepairs in length.

In preferred embodiments, the recipient is an animal, e.g., a miniature swine, a swine, a non-human primate, or a human.

In preferred embodiments, the graft is selected from the group consisting of: heart, lung, liver, bone marrow or kidney.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a method of screening a cell, e.g., a cell having a disorder, e.g., a proliferative disorder, e.g., a tumor cell, e.g., a cancer cell, e.g., a lymphoma or a hepatocellular carcinoma, developing in a graft recipient, e.g., a xenograft, for the presence or expression of a porcine retrovirus or retroviral sequence. The method includes:

contacting a target nucleic acid from a tumor cell with a second sequence chosen from the group of: a sequence which can specifically hybridize to a porcine retroviral sequence; a sequence which can specifically hybridize to the sequence of SEQ ID.NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid, under conditions in which the sample and the nucleic acid sequence can hybridize, hybridization being indicative of the presence of the endogenous porcine retrovirus or retroviral sequence in the tumor cell.

In preferred embodiments, the target nucleic acid from a tumor cell includes: genomic DNA, RNA or cDNA, e.g., cDNA made from an RNA template.

In a preferred embodiment: the second nucleic acid is a porcine retroviral sequence, probe or primer, e.g., as described herein, e.g., a Tsukuba-1 retroviral sequence; the second nucleic acid is a sequence of SEQ ID NO:1 or its complement, SEQ ID NO:2 or complement, or SEQ ID NO:3 or its complement, or a fragment of the sequence or complement at least 10, 20, or 30, basepairs in length.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a method of screening a human subject for the presence or expression of an endogenous porcine retrovirus or retroviral sequence comprising:

contacting a target nucleic acid derived from the human subject with a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid under conditions in which the sequences can hybridize, hybridization being indicative of the presence of the endogenous porcine retrovirus or retroviral sequence in the human subject.

In preferred embodiments, the target nucleic acid derived from a human subject is DNA, RNA or cDNA sample, nucleic acid from a blood sample or a tissue sample, e.g., a tissue biopsy sample.

In preferred embodiments, the human subject is a miniature swine or swine xenograft recipient, or a person who has come into contact with a miniature swine or swine xenograft recipient.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In preferred embodiments: the recipient is tested for the presence of porcine retroviral sequences prior to implantation of swine or miniature swine tissue.

In another aspect, the invention features a method of screening for viral mutations which modulate, e.g., increase or decrease, susceptibility of a porcine retrovirus to an antiviral agent, e.g., an antiviral antibiotic. The method includes:

administering a treatment, e.g., an antiviral agent, e.g., an antiviral antibiotic;

isolating a putative mutant porcine retroviral strain;

determining a structure of the putative mutant retroviral strain; and comparing the structure to SEQ ID NO:1 or its complement, SEQ ID NO:2 or its complement, or SEQ ID NO:3 or its complement.

In another aspect, the invention features a method of screening for viral mutations which modulate, e.g., increase or decrease, susceptibility of a porcine retrovirus to an antiviral agent, e.g., an antiviral antibiotic. The method includes:

growing the porcine retrovirus in a presence of a treatment, e.g., an antiviral agent, e.g., an antiviral antibiotic; and determine the amount of porcine retroviral DNA synthesized by hybridizing the porcine retroviral DNA to a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid, of at least 10 consecutive nucleotides of sense or antisense sequence which encodes a gag protein; a nucleic acid of at least 10 consecutive nucleotides of sense or antisense sequence from nucleotides 2452–4839 (e.g., from nucleotides 3112–4683) of SEQ ID NO:1, nucleotides 598–2169 (e.g., from nucleotides 598–2169) of SEQ ID NO:2, or nucleotides 585–2156 (e.g, from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid.

In preferred embodiments, the method further includes amplifying the porcine retroviral nucleic acid with primers which specifically hybridize to the sequence of SEQ ID NO:1 or its complement, SEQ ID NO:2 or its complement, or SEQ ID NO:3 or its complement, e.g., by polymerase chain reaction quantitative DNA testing (PDQ).

In a preferred embodiment: the second nucleic acid is a Tsukuba-1 retroviral sequence, probe or primer, e.g., as described herein; the second nucleic acid is a porcine retroviral sequence, probe or primer, e.g., as described herein; the second nucleic acid is the sequence of SEQ ID NO:1 or its complement, SEQ ID NO:2 or its complement, or SEQ ID NO:3 or its complement.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1060, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a method for screening a porcine-derived product for the presence or expression of a swine or miniature swine retrovirus or retroviral sequence, e.g., an endogenous miniature swine retrovirus. The method includes:

contacting a target nucleic acid from the porcine-derived product with a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737, of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid, under conditions in which hybridization can occur, hybridization being indicative of the presence or expression of an endogenous miniature swine or swine retrovirus or retroviral sequences in the porcine-derived product.

In preferred embodiments the product is: a protein product, e.g., insulin; a food product; or a cellular transplant, e.g., a swine or miniature swine cell which is to be transplanted into a host, e.g., a swine or miniature swine cell which is genetically engineered to express a desired product.

In preferred embodiments, the method further includes amplifying the target nucleic acid with primers which specifically hybridize to the sequence of SEQ ID NO:1 or its complement, SEQ ID NO:2 or its complement, or SEQ ID NO:3 or its complement.

In other preferred embodiments, the target nucleic acid is: DNA; RNA; or cDNA.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a transgenic miniature swine or swine having a transgenic element, e.g., a base change, e.g., a change from A to G, or an insertion or a deletion of one or more nucleotides at an endogenous porcine retroviral insertion site, e.g., a retroviral insertion which corresponds to the retroviral genome of SEQ ID NO:1 or its complement, SEQ ID NO:2 or its complement, or SEQ ID NO:3 or its complement.

In preferred embodiments, the transgenic element is a knockout, e.g., a deletion, insertion or a translocation, of one or more nucleic acids, which alters the activity of the endogenous porcine retrovirus.

In another aspect, the invention features a method of inhibiting expression of an endogenous porcine retrovirus, including: inserting a mutation, e.g. a deletion into the endogenous retrovirus.

In preferred embodiments, the endogenous porcine retrovirus is inactivated.

In preferred embodiments, the mutation can be a point mutation, an inversion, translocation or a deletion of one or more nucleotides of SEQ ID NO:1 or its complement, SEQ ID NO:2 or its complement, or SEQ ID NO:3 or its complement.

In another aspect, the invention features a method of detecting a recombinant virus or other pathogen, e.g., a protozoa or fungi. The method includes:

providing a pathogen having porcine retroviral sequence, and determining if the pathogen includes non-porcine retroviral sequence, the presence of non-porcine retroviral sequence being indicative of viral recombination.

In preferred embodiments, the method further includes determining the structure of a retrovirus by comparing the retrovirus sequence with sequence of SEQ ID NO:1 or its complement, SEQ ID NO:2 or its complement, or SEQ ID NO:3 or its complement, a difference being indicative of viral recombination.

In preferred embodiments, the method further includes comparing the structure of the retrovirus with a human retroviral sequence, e.g., HTLV1, HIV1, or HIV2, a similarity in structure being indicative of viral recombination.

In another aspect, the invention features a method of determining the copy number, size, or completeness of a porcine retrovirus or retroviral sequence , e.g., in the genome of a donor, recipient or a graft. The method includes:

contacting a target nucleic acid from the donor, recipient or a graft, with a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g, from nucleotides 598–2169):of SEQ ID NO:2, or nucleotides 585–2156 (e.g, from nucleotides 585–2156) of SEQ ID NO:3, or naturally occurring mutants thereof;

a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof;

a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid.

In preferred embodiments, the method further includes amplifying the porcine retroviral nucleic acid with primers which specifically hybridize to the sequence of SEQ ID NO:1 or its complement, SEQ ID NO:2 or its complement, or SEQ ID NO:3 or its complement, e.g., by polymerase chain reaction quantitative DNA testing (PDQ) or nested PCR.

In preferred embodiments, the target nucleic acid includes: genomic DNA isolated from a miniature swine; RNA or cDNA, e.g., cDNA made from an RNA template, isolated from a miniature swine; DNA, RNA or cDNA, e.g., cDNA made from an RNA template, isolated from a miniature swine organ, e.g., a kidney; RNA, DNA or cDNA, e.g., cDNA made from an RNA template, isolated from a miniature swine organ which has been transplanted into a organ recipient, e.g., a xenogeneic recipient, e.g., a primate, e.g., a human.

In preferred embodiments, the target nucleic acid includes: genomic DNA isolated from a swine; RNA or cDNA, e.g., cDNA made from an RNA template, isolated from a swine; DNA, RNA or cDNA, e.g., cDNA made from an RNA template, isolated from a swine organ, e.g., a kidney; RNA, DNA or cDNA, e.g., cDNA made from an RNA template, isolated from a swine organ which has been transplanted into a organ recipient, e.g., a xenogeneic recipient, e.g., a primate, e.g., a human.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a method for screening a tissue, e.g., a cellular or tissue transplant, e.g., a xenograft, or a tissue from a graft recipient, for the presence or expression of a swine or a miniature swine retroviral sequence, e.g., an endogenous miniature swine retrovirus. The method includes: contacting a tissue sample with an antibody specific for a retroviral protein, e.g., an anti-gag, pol, or env antibody, and thereby determining if the sequence is present or expressed.

In preferred embodiments the protein is encoded by a sequence from: the sequence of SEQ ID NO:1 or its complement, SEQ ID NO:2 or its complement, or SEQ ID NO:3 or its complement.

In preferred embodiments, the tissue is selected from the group consisting of: heart, lung, liver, bone marrow, kidney, brain cells, neural tissue, pancreas or pancreatic cells, thymus, or intestinal tissue.

A "purified preparation" or a "substantially pure preparation" of a polypeptide as used herein, means a polypeptide which is free from one or more other proteins, lipids, and nucleic acids with which it naturally occurs. Preferably, the polypeptide, is also separated from substances which are used to purify it, e.g., antibodies or gel matrix, such as polyacrylamide. Preferably, the polypeptide constitutes at least 10, 20, 50 70, 80 or 95% dry weight of the purified preparation. Preferably, the preparation contains: sufficient polypeptide to allow protein sequencing; at least 1, 10, or 100 μg of the polypeptide; at least 1, 10, or 100 mg of the polypeptide.

Specifically hybridize, as used herein, means that a nucleic acid hybridizes to a target sequence with substantially greater degree than it does to other sequences in a reaction mixture. By substantially greater means a difference sufficient to determine if the target sequence is present in the mixture.

A "treatment", as used herein, includes any therapeutic treatment, e.g., the administration of a therapeutic agent or substance, e.g., a drug or irradiation.

A "purified preparation of nucleic acid", is a nucleic acid which is one or both of: not immediately contiguous with one or both of the coding sequences with which it is immediately contiguous (i.e., one at the 5' end and one at the 3' end) in the naturally-occurring genome of the organism from which the nucleic acid is derived; or which is substantially free of a nucleic acid sequence or protein with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant DNA which is part of a hybrid gene encoding additional sequences. A purified retroviral genome is a nucleic acid which is substantially free of host nucleic acid or viral protein.

"Homologous", as used herein, refers to the sequence similarity between two polypeptide molecules or between two nucleic acid molecules. When a position in both of the two compared sequences is occupied by the same amino acid or base monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10, of the positions in two sequences are matched or homologous then the two sequences are 60% homologous. By way of example, the DNA sequences ATTGCC and TATGGC share 50% homology. Generally, a comparison is made when two sequences are aligned to give maximum homology. The term sequence identity has substantially the same meaning.

The term "provirus" or "endogenous retrovirus," as used herein, refers to an integrated form of the retrovirus.

The terms "peptides", "proteins", and "polypeptides" are used interchangeably herein.

As used herein, the term "transgenic element" means a nucleic acid sequence, which is partly or entirely heterologous, i.e., foreign, to the animal or cell into which it is introduced but which is designed to be inserted, or is inserted, into the animal's genome in such a way as to alter the genome of the cell into which it is inserted. The term includes elements which cause a change in the sequence, or in the ability to be activated, of an endogenous retroviral sequence. Examples of transgenic elements include those which result in changes, e.g., substitutions (e.g., A for G), insertions or deletions of an endogenous retroviral sequence (or flanking regions) which result in inhibition of activation or misexpression of a retroviral product.

As used herein, the term "transgenic cell" refers to a cell containing a transgenic element.

As used herein, a "transgenic animal" is any animal in which one or more, and preferably essentially all, of the cells of the animal includes a transgenic element. The transgenic element can be introduced into the cell, directly or indirectly by introduction into a precursor of the cell, by way of deliberate genetic manipulation, such as by microinjection. This molecule may be integrated within a chromosome, or it may be extrachromosomally replicating DNA.

As described herein, one aspect of the invention features a pure (or recombinant) nucleic acid which includes a miniature swine (or swine) retroviral genome or fragment thereof, e.g., nucleotide sequence encoding a gag-pol or env polypeptide, and/or equivalents of such nucleic acids. The term "nucleic acid", as used herein, can include fragments and equivalents. The term "equivalent" refers to nucleotide sequences encoding functionally equivalent polypeptides or functionally equivalent polypeptides which, for example, retain the ability to react with an antibody specific for a gag-pol or env polypeptide. Equivalent nucleotide sequences will include sequences that differ by one or more nucleotide substitutions, additions or deletions, such as allelic variants, and will, therefore, include sequences that differ from the nucleotide sequence of gag, pol, or env shown in herein due to the degeneracy of the genetic code.

"Misexpression", as used herein, refers to a non-wild type pattern of gene expression, e.g.,porcine retroviral, e.g., Tsukuba-1 gene expression, e.g., gag, pol or env gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing, size, amino acid sequence, post-translational modification, stability, or biological activity of the expressed ,porcine retroviral, e.g.,Tsukuba-1, polypeptides; a pattern of expression that differs from wild type in terms of the effect of an environmental stimulus or extracellular stimulus on expression of the porcine retroviral, e.g., Tsukuba-1 genes, e.g., a pattern of increased or decreased expression (as compared with wild type) in the presence of an increase or decrease in the strength of the stimulus.

Methods of the invention can be used with swine or miniature swine.

Endogenous retrovirus is a potential source of infection not always susceptible to conventional breeding practices. Many proviruses are defective and unable to replicate. Provirus, if intact, can be activated by certain stimuli and then initiate viral replication using the host's cellular mechanisms. Retroviral infection will often not harm the host cell. However, replication of virus may result in viremia, malignant transformation (e.g., via insertion of retroviral oncogenes), degeneration, or other insertional effects (e.g., gene inactivation). The effects of such infection may not emerge for many years. The spectrum of behavior of active lentiviral infection in humans is well described relative to HIV. These include AIDS, unusual infections and tumors, recombinant and other viruses, and antigenic variation which may prevent the generation of protective immunity by the infected host.

Screening of animals will allow elimination of donors with active replication of known viruses. Inactive proviruses can be detected with genetic probes and removed or inactivated. These novel approaches will allow the identification and elimination of potential human pathogens derived from swine in a manner not possible in the outbred human organ donor population and, thus, will be important to the development of human xenotransplantation.

The porcine retroviral sequences of the invention are also useful as diagnostic probes to detect activation of endogenous porcine retroviruses following transplantation and xenotransplantation of organs derived from swine or miniature swine. The porcine retroviral sequences of the invention also provide diagnostic tools necessary to assess the risks associated with transplantation of organs from swine or miniature swine into human recipients. These sequences are also useful for the longitudinal evaluation of retroviral activation in the human recipient of miniature swine-derived organs.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

Although methods and materials similar or equivalent to those described herein can be used in the practice or testing of the present invention, the preferred methods and materials are described below. All publications mentioned herein are incorporated by reference. In addition, the materials, methods, and examples are illustrative only and not intended to be limiting.

DETAILED DESCRIPTION OF THE DRAWINGS

FIG. 1 is the nucleotide sequence (SEQ ID NO: 1) of the Tsukuba-1 cDNA.

FIG. 2 is the nucleotide sequence (SEQ ID NO: 2) of a defective retroviral genome isolated from the retrovirus from the PK-15 cell line.

FIG. 3 is the nucleotide sequence (SEQ ID NO: 3) of a retrovirus found in miniature swine.

DETAILED DESCRIPTION

Miniature Swine Retroviruses

Transplantation may increase the likelihood of retroviral activation, if intact and infectious proviruses are present. Many phenomena associated with transplantation, e.g., immune suppression, graft rejection, graft-versus-host disease, viral co-infection, cytotoxic therapies, radiation therapy or drug treatment, can promote activation of retroviral expression.

Many species are thought to carry retroviral sequences in their genomic DNA. The number of intact (complete) retroviral elements that could be activated is often unknown. Once activated, swine-derived viruses would require the appropriate receptor on human tissues to spread beyond the transplanted organ. Most intact endogenous proviruses (usually types B and C), once activated, are not pathogenic. However, coinfection with other viruses, recombination with other endogenous viruses, or modification of viral behavior in the foreign human environment may alter the pathogenicity, organ specificity or replication of the retroviruses or other infectious agents.

The lack of sequence data on pig viruses has impeded efforts to assess the number of porcine sequences, or porcine retroviral sequences, that have incorporated into the human genome or the frequency of incorporation.

The inventor, by showing that the Tsukuba-1 retrovirus is found in miniature swine, and by providing the entire sequence of the porcine retroviral (Tsukuba-1) genome, has allowed assessment of the risk of endogenous retroviruses in general clinical practice and more importantly in xenotransplantation.

The porcine retroviral sequences of the invention can be used to determine the level (e.g., copy number) of intact (i.e., potentially replicating) porcine provirus sequences in a strain of xenograft transplantation donors. For example, the copy number of the miniature swine retroviral sequences can be determined by the Polymerase Chain Reaction DNA Quantitation (PDQ) method, described herein, or by other methods known to those skilled in the art. This quantitation technique will allow for the selection of animal donors, e.g., miniature swine donors, without an intact porcine retroviral sequence or with a lower copy number of viral elements.

The porcine retroviral sequences of the invention can be used to determine if mutations, e.g., inversions, translocations, insertions or deletions, have occurred in the endogenous porcine retroviral sequence. Mutated viral genomes may be expression-deficient. For example, genetic lesions can be identified by exposing a probe/primer derived from porcine retrovirus sequence to nucleic acid of the tissue (e.g., genomic DNA) digested with a restriction endonucleases or by in situ hybridization of the probe/primer derived from the porcine retroviral sequence to the nucleic acid derived from donor, e.g., miniature swine, tissue. Alternatively, direct PCR analysis, using primers specific for porcine retroviral genes (e.g., genes comprising the nucleotide sequence shown in SEQ ID NO: 1, 2, or 3), can be used to detect the presence or absence of the genetic lesion in the porcine retroviral genome.

Miniature swine retroviral sequences of the invention can also be use to detect viral recombinants within the genome, or in the circulation, cells, or transplanted tissue, between the porcine retrovirus and other endogenous human viruses or opportunistic pathogens (e.g. cytomegalovirus) of the immunocompromised transplant recipient. For example, pieces of the viral genome can be detected via PCR or via hybridization, e.g., Southern or Northern blot hybridization, using sequences derived from SEQ ID NO: 1, 2, or 3 as primers for amplification or probes for hybridization.

Miniature swine retroviral sequences of the invention, e.g., PCR primers, allow quantitation of activated virus. Sequences of the invention also allow histologic localization (e.g., by in situ hybridization) of activated retrovirus. Localization allows clinicians to, determine whether a graft should be removed as a source of potential retroviral infection of the human host or whether the retroviral infection was localized outside the graft.

Sequences of the invention, e.g., PCR primers, allow the detection of actively replicating virus, e.g., by using reverse transcribed PCR techniques known in the art. Standard techniques for reverse transcriptase measurements are often complicated, species-specific, and are of low sensitivity and specificity, and false positive results may develop using full-length probes for Southern and Northern molecular blotting. Sequences of the invention allow for sensitive and specific assays for the activation of virus and this will allow performance of a wide variety of tests, some of which are outlined below.

The invention provides for the testing and development of donor animals having reduced numbers of intact proviral insertions. It also provides for the testing of immunosuppressive regimens less likely to provide the conditions for active replication of retrovirus. Conditions likely to activate one retrovirus are generally more likely to activate other viruses including unknown retroviruses and known human pathogens including cytomegalovirus, hepatitis B and C viruses, Human Immunodeficiency Viruses (I and II). Given the availability of preventative therapies for these infections, these therapies could be used prophylactically in patients known to be susceptible to the activation of porcine retrovirus.

The miniature swine retroviral sequences of the invention can be used to measure the response of the miniature swine retroviral infection in humans to therapy, e.g., immunomodulatory or antiviral therapy, e.g., antiviral agents, e.g., antiviral antibiotics. With HIV, susceptibility to antiviral antibiotics is determined by the genetic sequence of the reverse transcriptase gene (RT pol region) and other genes. The ability to determine the exact sequence of the retroviral genes will allow the detection of mutations occurring during infection which would then confer resistance of this virus to antiviral agents. Primers, e.g., for the RT-pol region, of the invention can be used to detect and to sequence clinical viral isolates from patients which have developed mutations by PDQ method;described herein. The primers of the invention can also be used to determine whether tumor cells, e.g., cancer cells, e.g. lymphoma or hepatocellular carcinoma, developing in xenograft recipients contain porcine retroviral elements.

The porcine retroviral sequences of the invention can also be used to detect other homologous retroviruses and to determine whether these are the same or different as compared to the Tusukuba-1 retroviral sequences. For example, within a species, the polymerase genes are highly conserved. PCR assays aimed at the gag-pol region followed by sequence analysis allow for this detection of homologous viruses. The appropriate regions of the Tsukuba-1 virus can be determined by using sequences derived from SEQ ID NO:1, described herein, to identify additional 5' and 3' viral genomic sequences. As is discussed elsewhere herein, the sequences from SEQ ID NO: 1 were used to obtain the sequence of the PK-15 retroviral insert (SEQ ID NO:2) and of a retroviral insertion in a miniature swine (SEQ ID NO:3).

Miniature swine retroviral sequences of the invention can be used to screen donor animals and xenograft recipients after transplantation both for infection, and as a measure of the appropriate level of immune suppression, regarding susceptibility to infection. Physicians, medical staff, family, or individuals who come into contact with graft recipients, and others, can be screened for infection with virus derived from the xenograft recipient. Members of the population in general can also be screened. Such screening can be used for broad epidemiologic studies of the community. These methods can help in meeting the requirements of the F.D.A. regarding enhancing the safety of the recipients and of the community to exposure to new viruses introduced into the community by xenograft transplantation.

As is shown in Suzuka et al., 1986, FEBS 198:339, the swine retroviruses such as the Tsukuba-1 genome can exist as a circular molecule. Upon cloning the circular molecule is generally cleaved to yield a linear molecule. As will be understood by one skilled in the art, the start point and end point of the resulting linear molecule, and the relative subregions of the viral sequence will of course vary with the point of cleavage. For example, in the Suzuka et al. reference the LTR is shown to be in an internal fragment. This is indicated herein in that the order of gag, pol, env in SEQ ID NO 1 is shown as env, gag, pol, while elsewhere herein the order of these regions is given as the naturally occurring gag, pol, env order.

Primers Derived From the Porcine Retroviral (Tsukuba-1) Genome Sequence

A number of different primers useful in the methods of the invention have been described herein. One skilled in the art can identify additional primers from the viral sequence of SEQ ID NO:1 by using methods known in the art. For example, when trying to identify potentially useful primers one skilled in the art would look for sequences (sequences should be between about 15 and 30 nucleotides in length) which hybridize to SEQ ID NO:1 with high melting temperature; have a balanced distribution of nucleotides, e.g., a balanced distribution of A, T, C and Gs; have a terminal C or G; do not self-hybridize or internally complement.

Use of Primers Derived From the Porcine Retroviral (Tsukuba-1) Genome Sequence

I. Testing of Organs or Cells Prior to Transplantation

Potential donor animals can be screened for active retroviral replication prior to being used in transplantation. This allows avoidance of animals undergoing active viral replication. Replicating virus is often infectious in 100% of recipients, while nonreplicating, latent provirus generally causes infection in 5 to 25% of recipients.

II. Testing of Recipients

Serial samples, e.g., of white blood cells, can be obtained from a graft recipient monthly, e.g., for the first month and every three months thereafter. Tissue biopsies obtained for evaluation of graft function can be used to evaluate the activation of retroviral sequences or of the expression retroviral sequences in graft tissue. Samples can be screened for the presence of retrovirus infection both specifically for the homologous virus, for viral recombinants containing portions of the viral genome, and for other retroviruses, using, e.g., PCR primers for the pol region of the virus, which is the region most likely to be conserved. If virus is detected, quantitative PCR can be used to determine the relative stability of viral production. Cells isolated from xenograft recipients can be tested by cocultivation with permissive human and porcine (e.g., pig fallopian tube, pig macrophage, or pig testis) cell lines known to contain endogenous viruses. Isolated virus will be tested for homology with the parental strain and for mutations which might affect susceptibility to antiviral agents, e.g., antiviral antibiotics.

III. Testing of Surgical and Medical Personnel and Family Members of Graft Recipient Samples, e.g., white blood cells, can be banked (archived) from the surgical and medical personnel and from family members of the recipient prior to transplantation and at three months intervals for the first year and at least annually thereafter. Epidemiologic studies can be performed on these samples as well. These samples can be tested if the recipient becomes viremic or if unusual clinical manifestations are noted in these individuals.

IV. Testing of Tumor Cells

Tumor cells which develop from a graft, or a graft recipient, can be tested for the presence of active retrovirus and for proviruses.

V. Testing of Patients

Patients can be retested for any significant change in clinical condition or for increased immune suppression of graft rejection which may be associated with an increased risk of viral activation.

Sequencing of the Porcine Retroviral (Tsukuba-1) Genome

A clone (Pλ8.8) containing the 8060 bp XhoI porcine retrovirus (Tsukuba-1) insert was used to transfect competent *E. coli*, and DNA was isolated for sequencing. The strategy used to sequence the 8060 bp porcine retrovirus genome included a combination of procedures which are outlined below Random fragments (1–3 kb) of the clone (Pλ8.8) were generated by sonication. The fragments were blunt-ended and were subcloned into the EcoRV site of the pBluescript SK vector. Plasmid DNA was prepared using a modified alkaline lysis procedure. DNA sequencing was performed using DyeDeoxy termination reactions (ABI). Base specific fluorescent dyes were used as labels. Sequencing reactions were analyzed on 4.75% polyacrylamide gels by an ABI 373A-S or 373S automated sequencer. Subsequent data analysis was performed on Sequencer™ 3.0 software. The following internal sequencing primers were synthesized:

| | | |
|---|---|---|
| AP1 | 5' GATGAACAGGCAGACATCTG 3' | (SEQ ID NO:48) |
| AP2 | 5' CGCTTACAGACAAGCTGTGA 3' | (SEQ ID NO:49) |
| AP3 | 5' AGAACAAAGGCTGGGAAAGC 3' | (SEQ ID NO:50) |
| AP4 | 5' ATAGGAGACAGCCTGAACTC 3' | (SEQ ID NO:51) |
| AP5 | 5' GGACCATTGTCTGACCCTAT 3' | (SEQ ID NO:52) |
| AP6 | 5' GTCAACACCTATACCAGCTC 3' | (SEQ ID NO:53) |
| AP7 | 5' CATCTGAGGTATAGCAGGTC 3' | (SEQ ID NO:54) |
| AP8 | 5' GCAGGTGTAGGAACAGGAAC 3' | (SEQ ID NO:55) |
| AP9 | 5' ACCTGTTGAACCATCCCTCA 3' | (SEQ ID NO:56) |
| AP10 | 5' CGAATGGAGAGATCCAGGTA 3' | (SEQ ID NO:57) |
| AP11 | 5' CCTGCATCACTTCTCTTACC 3' | (SEQ ID NO:58) |
| AP12 | 5' TTGCCTGCTTGTGGAATACG 3' | (SEQ ID NO:59) |
| AP13 | 5' CAAGAGAAGAAGTGGGAATG 3' | (SEQ ID NO:60) |
| AP14 | 5' CACAGTCGTACACCACGCAG 3' | (SEQ ID NO:61) |
| AP15 | 5' GGGAGACAGAAGAAGAAAGG 3' | (SEQ ID NO:62) |
| AP16 | 5' CGATAGTCATTAGTCCCAGG 3' | (SEQ ID NO:63) |
| AP17 | 5' TGCTGGTTTGCATCAAGACCG 3' | (SEQ ID NO:64) |
| AP18 | 5' GTCGCAAAGGCATACCTGCT 3' | (SEQ ID NO:65) |
| AP19 | 5' ACAGAGCCTCTGCTAAGAAG 3' | (SEQ ID NO:66) |
| AP20 | 5' GCAGCTGTTGACAATCATC 3' | (SEQ ID NO:67) |
| AP21 | 5' TATGAGGAGAGGGCTTGACT 3' | (SEQ ID NO:68) |
| AP22 | 5' AGCAGACGTGCTAGGAGGT 3' | (SEQ ID NO:69) |
| AP23 | 5' TCCTCTTGCTGTTTGCATC 3' | (SEQ ID NO:70) |
| AP24 | 5' CAGACACTCAGAACAGAGAC 3' | (SEQ ID NO:71) |
| AP25 | 5' ACATCGTCTAACCCACCTAG 3' | (SEQ ID NO:72) |
| AP26 | 5' CTCGTTTCTGGTCATACCTGA 3' | (SEQ ID NO:73) |
| AP27 | 5' GAGTACATCTCTCTAGGCA 3' | (SEQ ID NO:74) |
| AP28 | 5' TGCCTAGAGACATGTACTC 3' | (SEQ ID NO:4) |
| AP29 | 5' CCTCTTCTAGCCATTCCTTCA 3' | (SEQ ID NO:5) |

The clone (Pλ8.8) containing the 8060 bp XhoI porcine retrovirus (Tsukuba-1) insert was deposited with ATCC on Dec. 27, 1995 (ATCC Deposit No97396).

Determination of the Porcine Retroviral (Tsukuba-1) Copy Number in a Miniature Swine Total genomic DNA was isolated from miniature swine kidney by the methods known in the art. The isolated genomic DNA was digested with either EcoRI or HindIII restriction enzyme. The DNA digests were electrophoresed on an agarose gel, Southern blotted and hybridized to the full-length, purified, Tsukuba-1 sequence (SEQ ID NO:1) under high stringency conditions (0.1×SSC, 65° C.). In both digested samples (EcoRI or HindIII) at least six copies of the high molecular fragments of the miniature swine genome (over 16 Kb in size) hybridized to SEQ ID NO:1, indicating the presence of homologous retroviral sequences in porcine DNA.

Susceptibility Testing by Polymerase Chain Reaction DNA Quantitation (PDQ)

Polymerase chain reaction (PCR) DNA quantitation (PDQ) susceptibility testing can be used to rapidly and directly measure nucleotide sensitivity of porcine retrovirus isolates. PCR can be used to quantitate the amount of porcine retroviral RNA synthesized after in vitro infection of peripheral blood mononuclear cells. The relative amounts of porcine retroviral RNA in cell lysates from cultures maintained at different drug concentrations reflect drug inhibition of virus replication. With the PDQ method both infectivity titration and susceptibility testing can be performed on supernatants from primary cultures of peripheral blood mononuclear cells.

The PDQ experiments can be performed essentially as described by Eron et al., *PNAS USA* 89:3241–3245, 1992. Briefly, aliquots (150 $\mu$l) of serial dilutions of virus sample can be used to infect $2\times10^6$ PHA-stimulated donor PBMCs in 1.5 ml of growth medium per well of a flat-bottom 24-well plate (Coming). Separate cell samples can be counted, harvested, and lysed at 48, 72 and 96 hr. Quantitative PCR and porcine retrovirus copy-number determination can then be performed in duplicate on each lysate.

The results of a PDQ infectivity titration assay can be used to determine the virus dilution and length of culture time employed in a subsequent PDQ susceptibility test. These parameters should be chosen so that the yield of porcine retrovirus specific PCR product for the untreated control infection would fall on the porcine retrovirus copy-number standard curve before the curve approached its asymptotic maximum, or plateau. PHA-stimulated donor PBMCs can be incubated with drug for 4 hr prior to infection. Duplicate wells in a 24-well plate should receive identical porcine retrovirus inocula for each drug concentration tested and for the untreated infected controls. Uninfected controls and drug toxicity controls should be included in each experiment. All cultures can be harvested and cells lysed for PCT after either 48 or 72 hr. Previously characterized isolates can be used as assay standards in each experiment.

Cell pellets can be lysed in various volumes of lysis buffer (50 mM KCl/10 mM Tris.HCl, pH 8.3/2.5 mM $MgCl_2$/0.5% Nonidet P-40/0.5% Tween 20/0.01% proteinase K) to yield a concentration of $1.2\times10^4$ cell equivalents/$\mu$l. Uniformity to cell lysate DNA concentrations should be confirmed in representative experiments by enhancement of Hoechst 33258 fluorescence (Mini-Fluorometer, Hoefer).

A conserved primer pair can be synthesized according to the pol gene sequences. The primers can than be used to amplify a 1580-base pair fragment of the porcine retrovirus pol gene from $1.2\times10^5$ cell equivalents of lysate by using PCR (GeneAmp, Cetus) under standard conditions. Amplifications should be repeated if porcine retrovirus DNA is amplifiable from reagent controls.

Porcine retrovirus pol gene amplification products can be specifically detected and quantitated as described (Conway, B. C. (1990) in *Techniques in HIV Research*, (Aldovani & Walker, eds.) (Stockton, N.Y.) pp40–46). Heat-denatured PCR products can be hybridized in a Streptavidin-coated microtiter plate well with both biotinylated capture probe and horseradish peroxidase (HRP)-labeled detector probe [enzyme-linked oligonucleotide solution sandwich hybridization assay ((ELOSA), DuPont Medical Products, Billerica, Mass.) for 60 min at 37° C. After extensive washing to remove all reactants except probe-DNA hybrids, an HRP chromogen, tetramethylbenzidine (TMBlue, Transgenic Sciences, Worcester, Mass.), should be added to each well. The HRP-catalyzed color development should be stopped after 1 hr by addition of sulfuric acid to 0.65 M. Absorbance (OD) at 450 nm can be measured in an automated microtiter plate reader (SLT Labinstruments, Hillsborough, N.C.).

A standard curve of porcine retrovirus DNA copy number can be generated in each PCR by using a dilution series of cells containing one porcine proviral genome per cell.

Preparation of a Miniature Swine Having a Knockout of Tsukuba-1 Viral Sequence Using Isogenic DNA Targeting Vectors Isogenic DNA, or DNA that is substantially identical in sequence between the targeting vector and the target DNA in the chromosomes, greatly increases the frequency for homologous recombination events and gene targeting efficiency. Using isogenic-DNA targeting vectors, targeting frequencies of 80% or higher can be achieved in mouse embryonic stem cells. This is in contrast to non-isogenic DNA vectors which normally yield targeting frequencies of around 0.5% to 5%, i.e., approximately two orders of magnitude lower than isogenic DNA vectors. Isogenic DNA constructs are predominantly integrated into chromosomes by homologous recombination rather than random integration. As a consequence, targeted mutagenesis of viral sequences, e.g., viral genes, can be carried out in biological systems including zygotes, which do not lend themselves to the use of elaborate selection protocols, resulting in production of animals, e.g., miniature swine, free of, or having a reduced number of, activatable viral sequences. In order for the isogenic DNA approach to be feasible, targeting vectors should be constructed from a source of DNA that is identical to the DNA of the organism to be targeted. Ideally, isogenic DNA targeting is carried out in inbred strains of animals, e.g., inbred miniature swine, in which all genetic loci are homozygous. Any animal of that strain can serve as a source for generating isogenic targeting vectors. This protocol for isogenic gene targeting is outlined in TeRiele et al., PNAS 89:5128–5132, 1992 and PCTIUS92/07184, herein incorporated by reference. A protocol for producing Tsukuba-1 knockout miniature swine is described briefly below.

An insertion vector is designed as described by Hasty and Bradley (Gene Targeting Vectors for Mammalian Cells, in Gene Targeting: A Practical Approach, ed, Alexandra L. Joyner, IRL Press 1993). Insertion vectors require that only one crossover event occur for integration by homologous recombination into the native locus. The double strand breaks, the two ends of the vector which are known to be highly recombinogenic, are located on adjacent sequences on the chromosome. The targeting frequencies of such constructions will be in the range of 30 to 50%. One disadvantage of insertion vectors, in general, concerns the sequence duplications that are introduced and that potentially make the locus unstable. All these constructions are made using standard cloning procedures.

Replacement vectors have also been extensively described by Hasty and Bradley. Conceptually more straight forward than the insertion vector, replacement vectors use an essentially co-linear fragment of a stretch of Tsukuba-1 genomic sequence. Preferably, the DNA sequence from which an isogenic replacement vector is constructed includes approximately 6 to 10 kb of uninterrupted DNA. Two crossovers, one on either side of the selectable marker causes the mutant targeting vector to become integrated and replace the wild-type gene.

Microinjection of the isogenic transgene DNA into one of the pronuclei of a porcine embryo at the zygote stage (one-cell embryo) is accomplished by modification of a protocol described earlier (Hammer et al. 1985, Nature 315, 680; Pursel et al. 1989, Science 244, 1281). The age and the weight of the donor pigs, e.g., haplotype specific miniswine, are critical to success. Optimally, the animals are of age 8 to 10 months and weigh 70 to 85 lbs. This increases the probability of obtaining an adequate supply of one-cell embryos for microinjection of the transgenes. In order to allow for accurate timing of the embryo collections at this stage from a number of embryo donors, the gilts are synchronized using a preparation of synthetic progesterone (Regumate). Hormone implants are applied to designated gilts 30 days prior to the date of embryo collection. Twenty days later, ten days prior to the date of collection, the implants are removed and the animals are treated with additional hormones to induce superovulation to increase the number of embryos for microinjection. Three days following implant removal, the animals are treated with 400 to 1000 IU of pregnant mare serum gonadotropin (PMSG) and with 750 IU of human chorionic gonadotropin (hCG) three to four days later. These animals are bred by artificial insemination (AI) on two consecutive days following injection of hCG.

Embryo collections are performed as follows: three days following the initial injection of hCG, the animals are anesthetized with an intramuscular injection of Telazol (3 mg/lb), Rompum (2 mg/lb) and Atropine (1 mg/lb). A midline laparotomy is performed and the reproductive tract exteriorized. Collection of the zygotes is performed by cannulating the ampulla of the oviduct and flushing the oviduct with 10 to 15 ml phosphate buffered saline, prewarmed to 39° C. Following the collection the donor animals are prepared for recovery from surgery according to USDA guidelines. Animals used twice for embryo collections are euthanized according to USDA guidelines.

Injection of the transgene DNA into the pronuclei of the zygotes is carried out as summarized below: Zygotes are maintained in medium HAM F-12 supplemented with 10% fetal calf serum at 38° C. in 5% $CO_2$ atmosphere. For injection the zygotes are placed into BMOC-2 medium, centrifuged at 13,000 g to partition the embryonic lipids and visualize the pronuclei. The embryos are placed in an injection chamber (depression slide) containing the same medium overlaid with light paraffin oil. Microinjection is performed on a Nikon Diaphot inverted-microscope equipped with Nomarski optics and Narishige micromanipulators. Using 40×lens power the embryos are held in place with a holding pipette and injected with a glass needle which is back-filled with the solution of DNA containing the transgenic element, e.g., a mutant viral gene (2 µg/ml). Injection of approximately 2 picoliters of the solution (4 femptograms of DNA), which is equivalent to around 500 copies of the transgenic element, e.g., a mutant viral gene, is monitored by the swelling of the pronucleus by about 50%. Embryos that are injected are placed into the incubator prior to transfer to recipient animals.

Recipient animals are prepared similarly to the donor animals, but not superovulated. Prior to the transfer of the injected embryos, recipient gilts are anesthetized, the abdomen opened surgically by applying a longitudinal incision and the ovaries exteriorized The oviduct ipsilateral to the ovary with the larger number of corpus lutei is flushed, the embryos checked to evaluate if the animals is reproductively sound. Approximately 4 to 6 zygotes injected with the transgenic element, e.g., a mutant viral gene, are transferred to the flushed oviduct, the abdominal incision sutured and the animals placed in a warm area for recovery. The status of the pregnancy is monitored by ultrasound starting at day 25, or approximately one week following the expected date of implantation. Pregnant recipients are housed separately until they are due to farrow.

Newborn piglets are analyzed for integration of the transgenic element into chromosomal DNA. Genomic DNA is extracted from an ear punch or a blood sample and initial screening is performed using PCR. Animals that are potentially transgenic element-positive are confirmed by Southern analysis. Transgenic founder animals are subjected to further analysis regarding the locus of transgenic element integration using Southern analysis.

The Isolation and Sequencing of an Endogenous Swine Retroviral Insert and of a Retroviral Insert in Porcine PK-15 Cells Cloning of PK15 and PAL Endogenous Retroviruses I. Poly A+ RNA Isolation Peripheral blood lymphocytes (PBLs) were prepared from haplotype d/d miniswine using standard protocols known in the art. The PBLs were cultured in the presence of 1% phytohemagglutinin (PHA) for about 84 hours. The activated PBLs were collected and total RNA was isolated using commercially available kits, such at Gentra's (Minneapolis, Minn.) PUREscript Kit. Poly A+RNA was isolated from the total RNA using another commercially available product, Dynal Dynabeads (Lake Success, N.Y.). Northern analysis of the RNA using a pig retroviral probe confirmed the presence of potentially full-length retroviral genome RNA. RNA from PK15 cells was isolated using similar protocols.

II. Construction of the cDNA Libraries

Using Superscript Choice System (Life Technologies Ltd, Gibco BRL, Gaithersburg, Md.) for cDNA Synthesis, a cDNA library was constructed using oligo dT to make the first strand cDNA. The use of Superscript reverse transcriptase was important in order to obtain full-length retroviral (RV) cDNAs, due to the length of the RV RNA. The cDNA library was enriched for large cDNA fragments by size selecting >4 kb fragments by gel electrophoresis. The cDNAs were cloned into Lambda ZAP Express (Clontech Laboratories, Inc. Palo Alto, Calif.), which is one of the few commercially available cDNA vectors that would accept inserts in the 1–12 kb range.

III. Screening of the cDNA Libraries $0.75-1.2 \times 10^6$ independent clones were screened using either gag and pol or gag and env probes. Double positive clones were further purified until single isolates were obtained (1 or 2 additional rounds of screening).

IV. Characterization of the Clones

Between 18 and 30 double positive clones were selected for evaluation. Lambda DNA was prepared using standard protocols, such as the Lambda DNA Kit (Qiagen Inc., Chatsworth, Calif.). The clones were analyzed by PCR to check for (a) RV genes, and (b) determine the size of insert and LTR regions. Restriction digests were also done to confirm the size of insert and to attempt to categorize the clones. Clones containing the longest inserts and having consistent and predicted PCR data were sequenced.

Development of a PCR-based Assay for the Detection of the Presence of an Endogenous Retrovirus in Cells, Tissues, Organs, Miniswine or Recipient Hosts (e.g., Primates, Humans)

Using a commercially available computer software program (such as RightPrimer, Oligo 4.0, MacVector or Geneworks), one can analyze sequences disclosed herein for the selection of PCR primer pairs. The criteria for the general selection of primer pairs includes:

a. The Tm of each primer is between 65–70° C.

b. The Tm's for each pair differ by no more than 3° C.

c. The PCR fragment is between 200–800 bp in length d. There are no repeats, self complementary bases, primer-dimer issues, etc for each pair A. Additional Criteria for: A Pig-specific PCR Assay a. Primers are selected within porcine-specific regions of the sequence—such as within gag, env, or U3. Porcine-specific primers are defined as sequences which overall have <70% homology to the corresponding region in human, mouse and primate retroviruses. In addition, the last five bases at the 3' end of the primer should be unique to the pig retroviral sequence.

b. Primers should have no more than one or two mismatched bases based on the miniswine, and retroviral sequences disclosed herein. These mismatched bases should, not be within the last three or four bases of the 3' end of the primer.

B. Additional Criteria for: Miniswine-specific PCR Assay a. Primers are selected such that there are at least one or two mismatches between miniswine and domestic pig sequences. At least one of these mismatches should be located within the last three or four bases at the 3' end of the primer. Preferably, these mismatches would be a change from either a G or C in miniswine to either an A or T in domestic pig.

RT-PCR Strategy

There are a number of commercially available RT-PCR Kits for routine amplification of fragments. Several primer pairs should be tested to confirm Tm and specificity. Location of primers within the sequence depends in part on what question is being answered. RT-PCR should answer questions about expression and presence of RV sequences. PCR will not necessarily answer the question of whether the retroviral sequence is full-length or encodes a replication competent retrovirus. A positive signal in these tests only says there is RV sequence present. Indication of the possibility of full-length viral genomes being present can be obtained by performing long PCR using primers in U5 and U3. A commercial kit for long RT-PCR amplification is available (Takara RNA LA PCR Kit). Confirmation of full-length viral genomes requires infectivity studies and/or isolation of viral particles.

Northern analyses would complement RT-PCR data. Detection of bands at the predicted size of full-length viral genomes with hybridization probes from env, U3 or U5 would provide stronger evidence. The presence of other small bands hybridizing would indicate the amount of defective viral fragments present.

ELISA-BASED ASSAY TO DETECT THE PRESENCE OF PORCINE RETROVIRAL PROTEINS, POLYPEPTIDES OR PEPTIDES

In addition to the use of nucleic acid-based, e.g., PCR-based assays, to detect the presence of retroviral sequences, ELISA based assays can detect the presence of porcine retroviral proteins, polypeptides and peptides.

The basic steps to developing an ELISA include (a) generation of porcine retroviral specific peptides, polypeptides and proteins; (b) generation of antibodies which are specific for the porcine retroviral sequences; (c) developing the assay.

Using the retroviral sequences disclosed herein, antigenic peptides can be designed using computer based programs such as MacVector or Geneworks to analyse the retroviral sequences. Alternatively, it is possible to express the porcine retroviral sequences in gene expression systems and to purify the expressed polypeptides or proteins . After synthesis, the peptides, polypeptides or proteins are used to immunize mice or rabbits and to develop serum containing antibodies.

Having obtained the porcine retroviral specific antibodies the ELISA can be developed as follows. ELISA plates are coated with a volume of polyclonal or monoclonal antibody (capture antibody) which is reactive with the analyte to be tested. Such analytes include porcine retroviruses or retroviral proteins such as env or p24. The ELISA plates are then incubated at 4° C. overnight. The coated plates are then washed and blocked with a volume of a blocking reagent to reduce or prevent non-specific hybridization. Such blocking reagents include bovine serum albumin (BSA), fetal bovine serum (FBS), milk, or gelatin. The temperature for the blocking process is 37° C. Plates can be used immediately or stored frozen at −20° C. until needed. The plates are then washed, loaded with a serial dilution of the analyte, incubated at 37° C., and washed again. Bound analyte is detected using a detecting antibody. Detecting antibodies include enzyme-linked, fluoresceinated, biotin-conjugated or other tagged polyclonal or monoclonal antibodies which are reactive with the analyte. If monoclonal antibodies are used the detecting antibody should recognize an epitope which is different from the capture antibody.

Other Embodiments

In another aspect, the invention provides a substantially pure nucleic acid having, or comprising, a nucleotide sequence which encodes a swine or miniature swine, e.g., a Tsukuba-1 retroviral gag polypeptide.

In preferred embodiments: the nucleic acid is or includes the nucleotide sequence from nucleotides 2452–4839 of SEQ ID NO:1; the nucleic acid is at least 60%, 70%, 80%, 90%, 95%, 98%, or 99% homologous with a nucleic acid sequence corresponding to nucleotides 2452–4839 of SEQ ID NO:1; or by a sequence which, hybridizes under high stringency conditions to nucleotides 2452–4839 of SEQ ID NO:1; the nucleic acid includes a fragment of SEQ ID NO:1 which is at least 25, 50, 100, 200, 300, 400, 500, or 1,000 bases in length; the nucleic acid differs from the nucleotide sequence corresponding to nucleotides 2452–4839 of SEQ ID NO:1 due to degeneracy in the genetic code; the nucleic acid differs from the nucleic acid sequence corresponding to nucleotides 2452–4839 of SEQ ID NO:1 by at least one nucleotide but by less than 5, 10, 15 or 20 nucleotides and preferably which encodes an active peptide.

In yet another preferred embodiment, the nucleic acid of the invention hybridizes under stringent conditions to a nucleic acid probe corresponding to at least 12 consecutive nucleotides from nucleotides 2452–4839 of SEQ ID NO:1, or more preferably to at least 20 consecutive nucleotides from nucleotides 2452–4839 of SEQ ID NO:1, or more preferably to at least 40 consecutive nucleotides from nucleotides 2452–4839 of SEQ ID NO:1.

In another aspect, the invention features, a purified recombinant nucleic acid having at least 50%, 60%, 70%, 80%, 90%, 95%, 98%, or 99% homology with a nucleotide sequence corresponding to nucleotides 2452–4839 of SEQ ID NO:1.

The invention also provides a probe or primer which includes or comprises a substantially purified oligonucleotide. The oligonucleotide includes a region of nucleotide sequence which hybridizes under stringent conditions to at least 10 consecutive nucleotides of sense or antisense sequence from nucleotides 2452–4839 of SEQ ID NO:1, or naturally occurring mutants thereof. In preferred embodiments, the probe or primer further includes a label attached thereto. The label can be, e.g., a radioisotope, a fluorescent compound, an enzyme, and/or an enzyme co-factor. Preferably the oligonucleotide is at least 10 and less than 20, 30, 50, 100, or 150 nucleotides in length. Preferred primers of the invention include oligonucleotides having a nucleotide sequence shown in any of SEQ ID NOs:32–37.

The invention involves nucleic acids, e.g., RNA or DNA, encoding a polypeptide of the invention. This includes double stranded nucleic acids as well as coding and antisense single strands.

In another aspect, the invention provides a substantially pure nucleic acid having, or comprising, a nucleotide sequence which encodes a swine or miniature swine, e.g., a Tsukuba-1 retroviral pol polypeptide.

In preferred embodiments: the nucleic acid is or includes the nucleotide sequence corresponding to nucleotides 4871–8060 of SEQ ID NO:1; the nucleic acid is at least 60%, 70%, 80%, 90%, 95%, 98%, or 99% homologous with a nucleic acid sequence corresponding to nucleotides 4871–8060 of SEQ ID NO:1; or by a sequence which, hybridizes under high stringency conditions to nucleotides 4871–8060 of SEQ ID NO1; the nucleic acid includes a fragment of SEQ ID NO:1 which is at least 25, 50, 100, 200, 300, 400, 500, or 1,000 bases in length; the nucleic acid differs from the nucleotide sequence corresponding to nucleotides 4871–8060 of SEQ ID NO:1 due to degeneracy in the genetic code; the nucleic acid differs from the nucleic acid sequence corresponding to nucleotides 4871–8060 of SEQ ID NO:1 by at least one nucleotide but by less than 5, 10, 15 or 20 nucleotides and preferably which encodes an active peptide.

In yet another preferred embodiment, the nucleic acid of the invention hybridizes under stringent conditions to a nucleic acid probe corresponding to at least 12 consecutive nucleotides from nucleotides 4871–8060 of SEQ ID NO:1, or more preferably to at least 20 consecutive nucleotides from nucleotides 4871–8060 of SEQ ID NO:1, or more preferably to at least 40 consecutive nucleotides from nucleotides 4871–8060 of SEQ ID NO:1.

In another aspect, the invention features, a purified recombinant nucleic acid having at least 50%, 60%, 70%, 80%, 90%, 95%, 98%, or 99% homology with a nucleotide sequence corresponding to nucleotides 4871–8060 of SEQ ID NO:1.

The invention also provides a probe or primer which includes or comprises a substantially purified oligonucleotide. The oligonucleotide includes a region of nucleotide sequence which hybridizes under stringent conditions to at least 10 consecutive nucleotides of sense or antisense sequence from nucleotides 4871–8060 of SEQ ID NO:1, or naturally, occurring mutants thereof. In preferred embodiments, the probe or primer further includes a label attached thereto. The label can be, e.g., a radioisotope, a fluorescent compound, an enzyme, and/or an enzyme co-factor. Preferably the oligonucleotide is at least 10 and less than 20, 30, 50, 100, or 150 nucleotides in length. Preferred primers of the invention include oligonucleotides having a nucleotide sequence shown in any of SEQ ID NOs:38–47.

The invention involves nucleic acids, e.g., RNA or DNA, encoding a polypeptide of the invention. This includes double stranded nucleic acids as well as coding and antisense single strands.

In another aspect, the invention provides a substantially pure nucleic acid having, or comprising, a nucleotide sequence which encodes a swine or miniature swine, e.g., a Tsukuba-1 retroviral env polypeptide.

In preferred embodiments: the nucleic acid is or includes the nucleotide sequence corresponding to nucleotides 2–1999 of SEQ ID NO:1; the nucleic acid is at least 60%, 70%, 80%, 90%, 95%, 98%, or 99% homologous with a nucleic acid sequence corresponding to nucleotides 2–1999 of SEQ ID NO:1; or by a sequence which, hybridizes under high stringency conditions to nucleotides 2–1999 of SEQ ID NO:1; the nucleic acid includes a fragment of SEQ ID NO:1 which is at least 25, 50, 100, 200, 300, 400, 500, or 1,000 bases in length; the nucleic acid differs from the nucleotide sequence corresponding to nucleotides 2–1999 of SEQ ID NO:1 due to degeneracy in the genetic code; the nucleic acid differs from the nucleic acid sequence corresponding to nucleotides 2–1999 of SEQ ID NO:1 by at least one nucleotide but by less than 5, 10, 15 or 20 nucleotides and preferably which encodes an active peptide.

In yet another preferred embodiment, the nucleic acid of the invention hybridizes under stringent conditions to a nucleic acid probe corresponding to at least 12 consecutive nucleotides from nucleotides 2–1999 of SEQ ID NO:1, or more preferably to at least 20 consecutive nucleotides from nucleotides 2–1999 of SEQ ID NO:1, or more preferably to at least 40 consecutive nucleotides from nucleotides 2–1999 of SEQ ID NO:1.

In another aspect, the invention features, a purified recombinant nucleic acid having at least 50%, 60%, 70%, 80%, 90%, 95%, 98%, or 99% homology with a nucleotide sequence corresponding to nucleotides 2–1999 of SEQ ID NO:1.

The invention also provides a probe or primer which inch ides or comprises a substantially purified oligonucleotide. The oligonucleotide includes a region of nucleotide sequence which hybridizes under stringent conditions to at least 10 consecutive nucleotides of sense or antisense sequence from nucleotides 2–1999 of SEQ ID NO:1, or naturally occurring mutants thereof. In preferred embodiments, the probe or primer further includes a label attached thereto. The label can be, e.g., a radioisotope, a fluorescent compound, an enzyme, and/or an enzyme co-factor. Preferably the oligonucleotide is at least 10 and less than 20, 30, 50, 100, or 150 nucleotides in length. Preferred primers of the invention include oligonucleotides having a nucleotide sequence shown in any of SEQ ID NOs:6–31.

The invention includes nucleic acids, e.g., RNA or DNA, encoding a polypeptide of the invention. This includes double stranded nucleic acids as well as coding and antisense single strands.

Included in the invention are: allelic variations, natural mutants, induced mutants, that hybridize under high or low stringency conditions to the nucleic acid of SEQ ID NO:1, 2, or 3 (for definitions of high and low stringency see Current Protocols in Molecular Biology, John Wiley & Sons, New York, 1989, 6.3.1–6.3.6, hereby incorporated by reference).

The invention also includes purified preparations of swine or miniature swine retroviral polypeptides, e.g., gag pol, or env polypeptides, or fragments thereof, preferably biologically active fragments, or analogs, of such polypeptides. In preferred embodiments: the polypeptides are miniature swine retroviruses polypeptides; the polypeptides are Tsukuba polypeptides; the polypeptides are gag, pol, or env polypeptides encoded by SEQ ID NO:1 or its complement, SEQ ID NO:2 or its complement, or SEQ ID NO:3 or its complement, or naturally occuring variants thereof.

A biologically active fragment or analog is one having any in vivo or in vitro activity which is characteristic of the Tsukuba-1 polypeptides described herein, or of other naturally occurring Tsukuba-1 polypeptides. Fragments include those expressed in native or endogenous cells, e.g., as a result of post-translational processing, e.g., as the result of the removal of an amino-terminal signal sequence, as well as those made in expression systems, e.g., in CHO cells. A useful polypeptide fragment or polypeptide analog is one which exhibits a biological activity in any biological assay for Tusukuba-1 polypeptide activity. Most preferably the fragment or analog possesses 10%, preferably 40%, or at least 90% of the activity of Tsukuba-1 polypeptides, in any in vivo or in vitro Tsukuba-1 polypeptide assay.

In order to obtain a such polypeptides, polypeptide-encoding DNA can be introduced into an expression vector, the vector introduced into a cell suitable for expression of the desired protein, and the peptide recovered and purified, by prior art methods. Antibodies to the polypeptides can be made by immunizing an animal, e.g., a rabbit or mouse, and recovering antibodies by prior art methods.

The invention also features a purified nucleic acid, which has least 60%, 70%, 72%, more preferably at least 85%, more preferably at least 90%, more preferably at least 95%, most preferably at least 98%, 99% or 100% sequence identity or homology with SEQ ID NO:1 or its complement, SEQ ID NO: 2 or its complement, or SEQ ID NO: 3 or its complement.

In preferred embodiments the nucleic acid is other than the entire retroviral genome of SEQ ID NO:1 or its complement, SEQ ID NO:2 or its complement, or SEQ ID NO:3 or its complement, e.g., it is at least 1 nucleotide longer, or at least 1 nucleotide shorter, or differs in sequence at at least one position. E.g., the nucleic acid is a fragment of the sequence of SEQ ID NO:1 or its complement, SEQ ID NO:2 or its complement, or SEQ ID NO:3 or its complement, or it includes sequence additional to that of SEQ ID NO:1, or its complement, SEQ ID NO:2 or its complement, or SEQ ID NO:3 or its complement.

In preferred embodiments: the sequence of the nucleic acid differs from the corresponding sequence of SEQ ID NO: 1 or its complement, SEQ ID NO:2 or its complement, or SEQ ID NO:3 or its complement, by 1, 2, 3, 4, or 5 base pairs; the sequence of the nucleic acid differs from the corresponding sequence of SEQ ID NO: 1 or its complement, SEQ ID NO:2 or its complement, or SEQ ID NO:3 or its complement, by at least 1, 2, 3, 4, or 5 base pairs but less than 6, 7, 8, 9, or 10 base pairs.

In other preferred embodiments: the nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length.

Equivalents

Those skilled in the art will be able to recognize, or be able to ascertain using no more than routine experimentation, numerous equivalents to the specific procedures described herein. Such equivalents are considered to be within the scope of this invention and are covered by the following claims.

What is claimed is:

1. A purified nucleic acid molecule at least 85% identical to a molecule selected from the group consisting of SEQ ID NO:1, the fully complementary sequence of SEQ ID NO:1, SEQ ID NO:2, the fully complementary sequence of SEQ ID NO:2, SEQ ID NO:3, the fully complementary sequence of SEQ ID NO:3.

2. The purified nucleic acid molecule of claim 1 that is SEQ ID NO:1.

3. The purified nucleic acid molecule of claim 1 that is the fully complementary sequence of SEQ ID NO:1.

4. The purified nucleic acid molecule of claim 1 that is SEQ ID NO:2.

5. The purified nucleic acid molecule of claim 1 that is the fully complementary sequence of SEQ ID NO:2.

6. The purified nucleic acid molecule of claim 1 that is SEQ ID NO:3.

7. The purified nucleic acid molecule of claim 1 that is the fully complementary sequence of SEQ ID NO:3.

8. A purified nucleic acid molecule selected from the group consisting of:
   (a) nucleotides 2–1999 of SEQ ID NO:1;
   (b) nucleotides 2452–4839 of SEQ ID NO:1;
   (c) nucleotides 4871–8060 of SEQ ID NO:1;
   (d) nucleotides 598–2169 of SEQ ID NO:2;
   (e) nucleotides 2320–4737 of SEQ ID NO:2;
   (f) nucleotides 4738–6722 of SEQ ID NO:2;
   (g) nucleotides 585–2156 of SEQ ID NO:3;
   (h) nucleotides 2307–5741 of SEQ ID NO:3; and
   (i) nucleotides 5620–7533 of SEQ ID NO:3.

9. The purified nucleic acid molecule of claim 8 that is nucleotides 2–1999 of SEQ ID NO:1.

10. The purified nucleic acid molecule of claim 8 that is nucleotides 2452–4839 of SEQ ID NO:1.

11. The purified nucleic acid molecule of claim 8 that is nucleotides 4871–8060 of SEQ ID NO:1.

12. The purified nucleic acid molecule of claim 8 that is nucleotides 598–2169 of SEQ ID NO:2.

13. The purified nucleic acid molecule of claim 8 that is nucleotides 2320–4737 of SEQ ID NO:2.

14. The purified nucleic acid molecule of claim 8 that is nucleotides 4738–6722 of SEQ ID NO:2.

15. The purified nucleic acid molecule of claim 8 that is nucleotides 585–2156of SEQ ID NO:3.

16. The purified nucleic acid molecule of claim 8 that is nucleotides 2307–5741 of SEQ ID NO:3.

17. The purified nucleic acid molecule of claim 8 that is nucleotides 5620–7533 of SEQ ID NO:3.

18. A purified nucleic acid sequence at least 15 base pairs in length selected from a polynucleotide sequence, the polynucleotide sequence selected from the group consisting of SEQ ID NO:1, the fully complementary sequence of SEQ ID NO:1, SEQ ID NO:2, the fully complementary sequence of SEQ ID NO:2, SEQ ID NO:3, and the fully complementary sequence of SEQ ID NO:3, and further characterized by having less than 70% homology with the corresponding region in human, mouse and primate retroviral sequences, wherein the last five 3' bases are unique to the selected sequence.

19. The purified nucleic acid sequence of claim 18 wherein the sequence is selected from SEQ ID NO:1.

20. The purified nucleic acid sequence of claim 18, wherein the sequence is selected from the fully complementary sequence of SEQ ID NO:1.

21. The purified nucleic acid sequence of claim 18, wherein the sequence is selected from SEQ ID NO:2.

22. The purified nucleic acid sequence of claim 18, wherein the sequence is selected from the fully complementary sequence of SEQ ID NO:2.

23. The purified nucleic acid sequence of claim 18, wherein the sequence is selected from SEQ ID NO:3.

24. The purified nucleic acid sequence of claim 18, wherein the sequence is selected from the fully complementary sequence of SEQ ID NO:3.

25. A purified nucleic acid sequence selected from the group consisting of SEQ ID NO:4 through SEQ ID NO:74.

26. A purified nucleic acid molecule at least 20 nucleotides in length that hybridizes under stringent conditions to a molecule selected from the group consisting of SEQ ID NO:1, the fully complementary sequence of SEQ ID NO:1, SEQ ID NO:2, the fully complementary sequence of SEQ ID NO:2, SEQ ID NO:3, the fully complementary sequence of SEQ ID NO:3.

27. A method of determining the copy number or size of a porcine retrovirus, comprising:
   contacting a target nucleic acid from the donor, recipient, or a graft, with a second nucleic acid selected from the group of: a sequence which can specifically hybridize to the sequence of SEQ ID NO:1, or its complement of the same length; a sequence which can specifically hybridize to the sequence of SEQ ID NO:2, or its complement of the sane length; a sequence which can specifically hybridize to the sequence of SEQ ID NO:3, or its complement of the same length; a nucleic acid which can specifically hybridize to a sense or antisense sequence which encodes a gag protein, said sense or antisense sequence being selected from the group consisting of gag-encoding nucleotides of SEQ ID NO:1, gag-encoding nucleotides of SEQ ID NO:2, and gag-encoding nucleotides of SEQ ID NO:3; a nucleic acid which can specifically hybridize to a sense or antisense sequence from nucleotides 2452–4939 or nucleotides 3112–4683 of SEQ ID NO:1, nucleotides 598–2169 of SEQ ID NO:2, or nucleotides 585–2156, of SEQ ID NO:3; a nucleic acid which can specifically hybridize to sense or antisense sequence which encodes a pol protein, said sense or antisense sequence being selected from the group consisting of pol-encoding nucleotides of SEQ ID NO:1, pol-encoding nucleotides of SEQ ID NO:2, and pol-encoding nucleotides of SEQ ID NO:3; a nucleic acid which can specifically hybridize to a sense or antisense sequence from a nucleotides 4871–8060 of SEQ ID NO:1, nucleotides 2320–4737 of SEQ ID NO:2, or nucleotides 2307–5741 of SEQ ID NO:3; a nucleic acid which can specifically hybridize to a sense or antisense sequence which encodes an env protein, said sense or antisense sequence being selected from the group consisting of env-encoding nucleotides of SEQ ID NO:1, env-encoding nucleotides of SEQ ID NO:2, and env-encoding nucleotides of SEQ ID NO:3; a nucleic acid which can specifically hybridize to a sense or antisense sequence from nucleotides 2–1999 or nucleotides 86–1999 of SEQ ID NO:], nucleotides 4738–6722 of SEQ ID NO:2, or nucleotides 1820–7533 of SEQ ID NO:3, wherein the target nucleic acid is from a human recipient.

\

UNITED STATES PATENT AND TRADEMARK OFFICE
CERTIFICATE OF CORRECTION

PATENT NO. : 6,699,663 B1  Page 1 of 1
DATED : March 2, 2004
INVENTOR(S) : Jay A. Fishman It is certified that error appears in the above-identified patent and that said Letters Patent is hereby corrected as shown below:

Title page,
Item [54], Title, delete "RETROVIRUS" and replace with -- RETROVIRUSES --.
Item [56], References Cited, OTHER PUBLICATIONS, "Calne,:" reference, delete "Transplatation" and replace with -- Transplantation --.
Please add missing references:
-- Fishman, "Preventing infections in xenotransplantation: xenosis from miniature swine," *Xeno* 3(4):72-77 (1995) --; and
-- Leman et al., "Diseases of Swine" 7$^{th}$ Edition, Ames, Iowa, Iowa State University Press, Table of Contents Only. (1992) --.

Column 87,
Line 60, delete "2156of" and replace with -- 2156 of --.

Column 88,
Line 55, delete "sane" and replace with -- same --.

Column 89,
Line 8, after "from" delete "a".

Column 90,
Line 7, delete "]" and replace with -- 1 --.
Line 9, delete "1820" and replace with -- 5620 --.

Signed and Sealed this

Fifteenth Day of November, 2005

JON W. DUDAS
*Director of the United States Patent and Trademark Office*

SEQUENCE LISTING (1) GENERAL INFORMATION:

(iii) NUMBER OF SEQUENCES: 74

(2) INFORMATION FOR SEQ ID NO: 1:

(i) SEQUENCE CHARACTERISTICS:
      (A) LENGTH: 8060 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

```
CTCGAGACTC GGTGGAAGGG CCCTTATCTC GTACTTTTGA CCACACCAAC GGCTGTGAAA      60

GTCGAAGGAA TCTCCACCTG GATCCATGCA TCCCACGTTA AGCCGGCGCC ACCTCCCGAT     120

TCGGGGTGGA AAGCCGAAAA GACTGAAAAT CCCCTTAAGC TTCGCCTCCA TCGCGTGGTT     180

CCTTACTCTG TCAATAACCT CTCAGACTAA TGGTATGCGC ATAGGAGACA GCCTGAACTC     240

CCATAAACCC TTATCTCTCA CCTGGTTAAT TACTGACTCC GGCACAGGTA TTAATATCAA     300

CAACACTCAA GGGGAGGCTC CTTTAGGAAC CTGGTGGCCT GATCTATACG TTTGCCTCAG     360

ATCAGTTATT CCTAGTCTGA CCTCACCCCC AGATATCCTC CATGCTCACG GATTTTATGT     420

TTGCCCAGGA CCACCAAATA ATGGAAAACA TTGCGGAAAT CCCAGAGATT TCTTTTGTAA     480

ACAATGGAAC TGTGTAACCT CTAATGATGG ATATTGGAAA TGGCCAACCT CTCAGCAGGA     540

TAGGGTAAGT TTTTCTTATG TCAACACCTA TACCAGCTCT GGACAATTTA ATTACCTGAC     600

CTGGATTAGA ACTGGAAGCC CCAAGTGCTC TCCTTCAGAC CTAGATTACC TAAAAATAAG     660

TTTCACTGAG AAAGGAAAAC AAGAAAATAT CCTAAAATGG GTAAATGGTA TGTCTTGGGG     720

AATGGTATAT TATGGAGGCT CGGGTAAACA ACCAGGCTCC ATTCTAACTA TTCGCCTCAA     780

AATAAACCAG CTGGAGCCTC CAATGGCTAT AGGACCAAAT ACGGTCTTGA CGGGTCAAAG     840

ACCCCCAACC CAAGGACCAG GACCATCCTC TAACATAACT TCTGGATCAG ACCCCACTGA     900

GTCTAGCAGC ACGACTAAAA TGGGGGCAAA ACTTTTTAGC CTCATCCAGG GAGCTTTTCA     960

AGCTCTTAAC TCCACGACTC CAGAGGCTAC CTCTTCTTGT TGGCTATGCT TAGCTTTGGG    1020

CCCACCTTAC TATGAAGGAA TGGCTAGAAG AGGGAAATTC AATGTGACAA AAGAACATAG    1080

AGACCAATGC ACATGGGGAT CCCAAAATAA GCTTACCCTT ACTGAGGTTT CTGGAAAAGG    1140

CACCTGCATA GGAAAGGTTC CCCCATCCCA CCAACACCTT TGTAACCACA CTGAAGCCTT    1200

TAATCAAACC TCTGAAAGTC AATATCTGGT ACCTGGTTAT GACAGGTGGT GGGCATGTAA    1260

TACTGGATTA ACCCCTTGTG TTTCCACCTT GGTTTTTAAC CAAACTAAAG ATTTTTGCAT    1320

TATGGTCCAA ATTGTTCCCC GAGTGTATTA CTATCCCGAA AAAGCAATCC TTGATGAATA    1380

TGACTACAGA AATCATCGAC AAAAGAGAGA ACCCATATCT CTGACACTTG CTGTGATGCT    1440

CGGACTTGGA GTGGCAGCAG GTGTAGGAAC AGGAACAGCT GCCCTGGTCA CGGGACCACA    1500
```

-continued

```
GCAGCTAGAA ACAGGACTTA GTAACCTACA TCGAATTGTA ACAGAAGATC TCCAAGCCCT    1560

AGAAAAATCT GTCAGTAACC TGGAGGAATC CCTAACCTCC TTATCTGAAG TAGTCCTACA    1620

GAATAGAAGA GGGTTAGATT TATTATTTCT AAAAGAAGGA GGATTATGTG TAGCCTTGAA    1680

GGAGGAATGC TGTTTTTATG TGGATCATTC AGGGGCCATC AGAGACTCCA TGAACAAACT    1740

TAGAGAAAGG TTGGAGAAGC GTCGAAGGGA AAAGGAAACT ACTCAAGGGT GGTTTGAGGG    1800

ATGGTTCAAC AGGTCTCCTT GGTTGGCTAC CCTACTTTCT GCTTTAACAG GACCCTTAAT    1860

AGTCCTCCTC CTGTTACTCA CAGTTGGGCC ATGTATTATT AACAAGTTAA TTGCCTTCAT    1920

TAGAGAACGA ATAAGTGCAG TCCAGATCAT GGTACTTAGA CAACAGTACC AAAGCCCGTC    1980

TAGCAGGGAA GCTGGCCGCT AGCTCTACCA GTTCTAAGAT TAGAACTATT AACAAGAGAA    2040

GAAGTGGGGA ATGAAAGGAT GAAAATACAA CCTAAGCTAA TGAGAAGCTT AAAATTGTTC    2100

TGAATTCCAG AGTTTGTTCC TTATAGGTAA AAGATTAGGT TTTTTGCTGT TTTAAAATAT    2160

GCGGAAGTAA AATAGGCCCT GAGTACATGT CTCTAGGCAT GAAACTTCTT GAAACTATTT    2220

GAGATAACAA GAAAAGGGAG TTTCTAACTG CTTGTTTAGC TTCTGTAAAA CTGGTTGCGC    2280

CATAAAGATG TTGAAATGTT GATACACATA TCTTGGTGAC AACATGTCTC CCCCACCCCG    2340

AAACATGCGC AAATGTGTAA CTCTAAAACA ATTTAAATTA ATTGGTCCAC GAAGCGCGGG    2400

CTCTCGAAGT TTTAAATTGA CTGGTTTGTG ATATTTTGAA ATGATTGGTT TGTAAAGCGC    2460

GGGCTTTGCT GTGAACCCCA TAAAAGCTGT CCCGACTCCA CACTCGGGGC CGCAGTCCTC    2520

TACCCCTGCG TGGTGTACGA CTGTGGGCCC CAGCGCGCTT GGAATAAAAA TCCTCTTGCT    2580

GTTTGCATCA AGACCGCTTC TCGTGAGTGA TTAAGGGGAG TCGCCTTTTC CGAGCCTGGA    2640

GGTTCTTTTT GCTGGTCTTA CATTTGGGGG CTCGTCCGGG ATCTGTCGCG GCCACCCCTA    2700

ACACCCGAGA ACCGACTTGG AGGTAAAAAG GATCCTCTTT TTAACGTGTA TGCATGTACC    2760

GGCCGGCGTC TCTGTTCTGA GTGTCTGTTT TCAGTGGTGC GCGCTTTCGG TTTGCAGCTG    2820

TCCTCTCAGG CCGTAAGGGC TGGGGGACTG TGATCAGCAG ACGTGCTAGG AGGATCACAG    2880

GCTGCTGCCC TGGGGGACGC CCCGGGAGGT GAGGAGAGCC AGGGACGCCT GGTGGTCTCC    2940

TACTGTCGGT CAGAGGACCG AATTCTGTTG CTGAAGCGAA AGCTTCCCCC TCCGCGACCG    3000

TCCGACTCTT TTGCCTGCTT GTGGAATACG TGGACGGGTC ACGTGTGTCT GGATCTGTTG    3060

GTTTCTGTTT TGTGTGTCTT TGTCTTGTGT GTCCTTGTCT ACAGTTTTAA TATGGGACAG    3120

ACGGTGACGA CCCCTCTTAG TTTGACTCTC GACCATTGGA CTGAAGTTAA ATCCAGGGCT    3180

CATAATTTGT CAGTTCAGGT TAAGAAGGGA CCTTGGCAGA CTTTCTGTGT CTCTGAATGG    3240

CCGACATTCG ATGTTGGATG GCCATCAGAG GGGACCTTTA ATTCTGAGAT TATCCTGGCT    3300

GTTAAAGCAA TTATTTTTCA GACTGGACCC GGCTCTCATC CCGATCAGGA GCCCTATATC    3360

CTTACGTGGC AAGATTTGGC AGAGGATCCT CCGCCATGGG TTAAACCATG GCTGAATAAG    3420

CCAAGAAAGC CAGGTCCCCG AATTCTGGCT CTTGGAGAGA AAAACAAACA CTCGGCTGAA    3480

AAAGTCAAGC CCTCTCCTCA TATCTACCCC GAGATTGAGG AACCACCGGC TTGGCCGGAA    3540

CCCCAATCTG TTCCCCCACC CCCTTATCTG GCACAGGGTG CCGCGAGGGG ACCCTTTGCC    3600

CCTCCTGGAG CTCCGGCGGT GGAGGGACCT TCTGCAGGGA CTCGGAGCCG GAGGGCGCC    3660

ACCCCGGAGC GGACAGACGA GATCGCGACA TTACCGCTGC GCACGTACGG CCCTCCCACA    3720

CCGGGGGGCC AATTGCAGCC CCTCCAGTAT TGGCCCTTTT CTTCTGCAGA TCTCTATAAT    3780

TGGAAAACTA ACCATCCCCC TTTCTCGGAG GATCCCCAAC GCCTCACGGG GTTGGTGGAG    3840
```

```
TCCCTTATGT TCTCTCACCA GCCTACTTGG GATGATTGTC AACAGCTGCT GCAGACACTC    3900

TTCACAACCG AGGAGCGAGA GAGAATTCTA TTAGAGGCTA GAAAAAATGT TCCTGGGGCC    3960

GACGGGCGAC CCACGCGGTT GCAAAATGAG ATTGACATGG GATTTCCCTT AACTCGCCCC    4020

GGTTGGGACT ACAACACGGC TGAAGGTAGG GAGAGCTTGA AAATCTATCG CCAGGCTCTG    4080

GTGGCGGGTC TCCGGGCGC CTCAAGACGG CCCACTAATT TGGCTAAGGT AAGAGAAGTG     4140

ATGCAGGGAC CGAATGAACC CCCCTCTGTT TTTCTTGAGA GGCTCTTGGA AGCCTTCAGG    4200

CGGTACACCC CTTTTGATCC CACCTCAGAG GCCCAAAAAG CCTCAGTGGC TTTGGCCTTT    4260

ATAGGACAGT CAGCCTTGGA TATTAGAAAG AAGCTTCAGA GACTGGAAGG GTTACAGGAG    4320

GCTGAGTTAC GTGATCTAGT GAAGGAGGCA GAGAAAGTAT ATTACAAAAG GGAGACAGAA    4380

GAAGAAAGGG AACAAAGAAA AGAGAGAGAA AGAGAGGAAA GGGAGGAAAG ACGTAATAAA    4440

CGGCAAGAGA AGAATTTGAC TAAGATCTTG GCTGCAGTGG TTGAAGGGAA AAGCAATACG    4500

GAAAGAGAGA GAGATTTTAG GAAAATTAGG TCAGGCCCTA GACAGTCAGG GAACCTGGGC    4560

AATAGGACCC CACTCGACAA GGACCAATGT GCATATTGTA AAGAAAGAGG ACACTGGGCA    4620

AGGAACTGCC CCAAGAAGGG AAACAAAGGA CCAAGGATCC TAGCTCTAGA AGAAGATAAA    4680

GATTAGGGGA GACGGGGTTC GGACCCCCTC CCCGAGCCCA GGGTAACTTT GAAGGTGGAG    4740

GGGCAACCAG TTGAGTTCCT GGTTGATACC GGAGCGAAAC ATTCAGTGCT ACTACAGCCA    4800

TTAGGAAAAC TAAAGATAA AAAATCCTGG GTGATGGGTG CACAGGGCAA CAACAGTATC     4860

CATGGACTAC CCGAAGACAG TTGACTTGGG AGTGGGACGG GTAACCCACT CGTTTCTGGT    4920

CATACCTGAG TGCCCAGCAC CCCTCTTAGG TAGAGACTTA TTGACCAAGA TGGGAGCACA    4980

AATTTCTTTT GAACAAGGGA AACCAGAAGT GTCTGCAAAT AACAAACCTA TCACTGTGTT    5040

GACCCTCCAA TTAGATGACG AATATCGACT ATACTCTCCC CTAGTAAAGC CTGATCAAAA    5100

TATACAATTC TGGTTGGAAC AGTTTCCCCA AGCCTGGGCA GAAACCGCAG GATGGGTTT     5160

GGCAAAGCAA GTTCCCCCAC AAGTTATTCA ACTGAAGGCC AGTGCCACAC CAGTGTCAGT    5220

CAGACAGTAC CCCTTGAGTA AAGAAGCTCA AGAAGGAATT CGGCCGCATG TCCAAAGATT    5280

AATCCAACAG GCATCCTAG TTCCTGTCCA ATCTCCCTGG AATACTCCCC TGCTACCGGT     5340

TAGAAAGCCT GGGACTAATG ACTATCGACC AGTACAGGAC TTGAGAGAGG TCAATAAACG    5400

GGTGCAGGAT ATACACCCAA CAGTCCCGAA CCCTTATAAC CTCTTGTGTG CTCTCCCACC    5460

CCAACGGAGC TGGTATACAG TATTGGACTT AAAGGATGCC TTCTTCTGCC TGAGATTACA    5520

CCCCACTAGC CAACCACTTT TTGCCTTCGA ATGGAGAGAT CCAGGTACGG GAAGAACCGG    5580

GCAGCTCACC TGGACCCGAC TGCCCCAAGG GTTCAAGAAC TCCCCGACCA TCTTTGACGA    5640

AGCCCTACAC AGAGACCTGG CCAACTTCAG GATCCAACAC CCTCAGGTGA CCCTCCTCCA    5700

GTACGTGGAT GACCTGCTTC TGGCGGGAGC CACCAAACAG GACTGCTTAG AAGGCACGAA    5760

GGCACTACTG CTGGAATTGT CTGACCTAGG CTACAGAGCC TCTGCTAAGA AGGCCCAGAT    5820

TTGCAGGAGA GAGGTAACAT ACTTGGGGTA CAGTTTACGG GACGGGCAGC GATGGCTGAC    5880

GGAGGCACGG AAGAAAACTG TAGTCCAGAT ACCGGCCCCA ACCACAGCCA AACAAATGAG    5940

AGAGTTTTTG GGGACAGCTG GATTTTGCAG ACTGTGGATC CCGGGGTTTG CGACCTTAGC    6000

AGCCCCACTC TACCCGCTAA CCAAAGAAAA AGGGGAATTC TCCTGGGCTC CTGAGCACCA    6060

GAAGGCATTT GATGCTATCA AAAGGCCCCT GCTGAGCGCA CCTGCTCTGG CCCTCCCTGA    6120

CGTAACTAAA CCCTTTACCC TTTATGTGGA TGAGCGTAAG GGAGTAGCCC GGGGAGTTTT    6180

AACCCAAACC CTAGGACCAT GGAGAAGACC TGTCGCCTAC CTGTCAAAGA AGCTCGATCC    6240
```

```
TGTAGCCAGT GGTTGGCCCA TATGCCTGAA GGCTATCGCA GCTGTGGCCA TACTGGTCAA      6300

GGACGCTGAC AAATTGACTT TGGGACAAGA ATATAACTGT AATAGCCCCC CATGCATTGG      6360

AGAACATCGT TCGGCAGCCC CCAGACCGAT GGATGACCAA CGCCCGCATG ACCCACTATC      6420

AAAGCCTGCT TCTCACAGAG AGGGTCACGT TCGCTCCACC AACCGCTCTC AACCCTGCCA      6480

CTCTTCTGCC TGAAGAGACT GATGAACCAG TGACTCATGA TTGCCATCAA CTATTGATTG      6540

AGGAGACTGG GGTCCGCAAG GACCTTACAG ACATACCGCT GACTGGAGAA GTGCTAACCT      6600

GGTTCACTGA CGGAAGCAGC TATGTGGTGG AAGGTAAGAG GATGGCTGGG GCGGCGGTGG      6660

TGGACGGGAC CCGCACGATC TGGGCCAGCA GCCTGCCGGG AGGAACTTCA GCACAAAAGG      6720

CTGAGCTCAT GGCCCTCACG CAAGCTTTGC GGCTGGCCGA AGGGAAATCC ATAAACATTT      6780

ATACGGACAG CAGGTATGCC TTTGCGACTG CACACGTACA TGGGGCCATC TATAAACAAA      6840

GGGGGTTGCT TACCTCAGCA GGGAGGGAAA TAAAGAACAA AGAGGAAATT CTAAGCCTAT      6900

TAGAAGCCGT ACATTTACCA AAAAGGCTAG CTATTATACA CTGTCCTGGA CATCAGAAAG      6960

CTAAAGATCT CATATCCAGA GGAAACCAGA TGGCTGACCG GGTTGCCAAG CAGGCAGCCC      7020

AGGGTGTTAA CCTTCTGCCT ATAATAGAAA TGCCCAAAGC CCCAGAACCC AGACGACAGT      7080

ACACCCTAGA AGACTGGCAA GAGATAAAAA AGATAGACCA TTCTCTGAGA CTCCGGAAGG      7140

GACCTGCTAT ACCTCAGATG GGAAGGAAAT CCTGCCCCAC AAAGAAGGGT TAGAATATGT      7200

CCAACAAGAT ACATCGTCTA ACCCACCTAG GAACTAAACA CCTGCAGCAG TTGGTCAGAA      7260

CATCCCCTTA TCATGTTCTG AGGCTACCAG GAGTGGCTGA CTCGGTGGTC AAACATTGTG      7320

TGCCCTGCCA GCTGGTTAAT GCTAATCCTT CCAGAATGCC TCCAGGGAAG AGACTAAGGG      7380

GAAGCCACCC AGGCGCTCAC TGGGAAGTGG ACTTCACTGA GGTAAAGCCG GCTAAATATG      7440

GAAACAAATA CCTATTGGTT TTTGTAGACA CCTTTTCAGG ATGGGTAGAG GCTTATCCTA      7500

CTAAGAAAGA GACTTCAACC GTGGTAGCTA AAAAAATACT GGAAGAAATT TTTCCAAGAT      7560

TTGGAATACC TAAGGTAATA GGGTCAGACA ATGGTCCAGC TTTTGTTGCC CAGGTAAGTC      7620

AGGGACTGGC CAAGATATTG GGGATTGATT GGAAACTGCA TTGTGCATAC AGACCCCAAA      7680

GCTCAGGACA GGTAGAGAGG ATGAATAGAA CCATTAAAGA GACCCTTACT AAATTGACCG      7740

CGGAGACTGG CGTTAATGAT TGGATAGCTC TCCTGCCCTT TGTGCTTTTT AGGGTTAGGA      7800

ACACCCCTGG ACAGTTTGGG CTGACCCCCT ATGAATTACT CTACGGGGGA CCCCCCCCAT      7860

TGGTAGAAAT TGCTTCTGTA CATAGTGCTG ATGTGCTGCT TTCCCAGCCT TTGTTCTCTA      7920

GGCTCAAGGC ACTTGAGTGG GTGAGACAAC GAGCGTGGAG GCAACTCCGG GAGGCCTACT      7980

CAGGAGGAGG AGACTTGCAG ATCCCACATC GTTTCCAAGT GGGAGATTCA GTCTACGTTA      8040

GACGCCACCG TGCAGGAAAC                                                  8060

(2) INFORMATION FOR SEQ ID NO: 2:

(i) SEQUENCE CHARACTERISTICS:
        (A) LENGTH: 7333 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

CTACCCCTGC GTGGTGTACG ACTGTGGGCC CCAGCGCGCT TGGAATAAAA ATCCTCTTGC        60

TGTTTGCATC AAGACCGCTT CTTGTGAGTG ATTTGGGGTG TCGCCTCTTC CGAGCCCGGA       120
```

```
CGAGGGGGAT TGTTCTTTTA CTGGCCTTTC ATTTGGTGCG TTGGCCGGGA AATCCTGCGA      180

CCACCCCTTA CACCCGAGAA CCGACTTGGA GGTAAAGGGA TCCCCTTTGG AACATATGTG      240

TGTGTCGGCC GGCGTCTCTG TTCTGAGTGT CTGTTTTCGG TGATGCGCGC TTTCGGTTTG      300

CAGCTGTCCT CTCAGACCGT AAGGACTGGA GGACTGTGAT CAGCAGACGT GCTAGGAGGA      360

TCACAGGCTG CCACCCTGGG GGACGCCCCG GGAGGTGGGG AGAGCCAGGG ACGCCTGGTG      420

GTCTCCTACT GTCGGTCAGA GGACCGAGTT CTGTTGTTGA AGCGAAAGCT TCCCCCTCCG      480

CGGCCGTCCG ACTCTTTTGC CTGCTTGTGG AAGACGCGGA CGGGTCGCGT GTGTCTGGAT      540

CTGTTGGTTT CTGTTTCGTG TGTCTTTGTC TTGTGCGTCC TTGTCTACAG TTTTAATATG      600

GGACAGACAG TGACTACCCC CCTTAGTTTG ACTCTCGACC ATTGGACTGA AGTTAGATCC      660

AGGGCTCATA ATTTGTCAGT TCAGGTTAAG AAGGGACCTT GGCAGACTTT CTGTGCCTCT      720

GAATGGCCAA CATTCGATGT TGGATGGCCA TCAGAGGGGA CCTTTAATTC TGAAATTATC      780

CTGGCTGTTA AGGCAATCAT TTTTCAGACT GGACCCGGCT CTCATCCTGA TCAGGAGCCC      840

TATATCCTTA CGTGGCAAGA TTTGGCAGAA GATCCTCCGC CATGGGTTAA ACCATGGCTA      900

AATAAACCAA GAAAGCCAGG TCCCCGAATC CTGGCTCTTG GAGAGAAAAA CAAACACTCG      960

GCCGAAAAAG TCGAGCCCTC TCCTCGTATC TACCCCGAGA TCGAGGAGCC GCCGACTTGG     1020

CCGGAACCCC AACCTGTTCC CCCACCCCCT TATCCAGCAC AGGGTGCTGT GAGGGGACCC     1080

TCTGCCCCTC CTGGAGCTCC GGTGGTGGAG GGACCTGCTG CCGGGACTCG GAGCCGGAGA     1140

GGCGCCACCC CGGAGCGGAC AGACGAGATC GCGATATTAC CGCTGCGCAC CTATGGCCCT     1200

CCCATGCCAG GGGGCCAATT GCAGCCCCTC CAGTATTGGC CCTTTTCTTC TGCAGATCTC     1260

TATAATTGGA AAACTAACCA TCCCCCTTTC TCGGAGGATC CCCAACGCCT CACGGGGTTG     1320

GTGGAGTCCC TTATGTTCTC TCACCAGCCT ACTTGGGATG ATTGTCAACA GCTGCTGCAG     1380

ACACTCTTCA CAACCGAGGA GCGAGAGAGA ATTCTGTTAG AGGCTAAAAA AAATGTTCCT     1440

GGGGCCGACG GCGACCCAC GCAGTTGCAA AATGAGATTG ACATGGGATT TCCCTTGACT     1500

CGCCCCGGTT GGGACTACAA CACGGCTGAA GGTAGGGAGA GCTTGAAAAT CTATCGCCAG     1560

GCTCTGGTGG CGGGTCTCCG GGGCGCCTCA AGACGGCCCA CTAATTTGGC TAAGGTAAGA     1620

GAGGTGATGC AGGGACCGAA CGAACCTCCC TCGGTATTTC TTGAGAGGCT CATGGAAGCC     1680

TTCAGGCGGT TCACCCCTTT TGATCCTACC TCAGAGGCCC AGAAAGCCTC AGTGGCCCTG     1740

GCCTTCATTG GGCAGTCGGC TCTGGATATC AGGAAGAAAC TTCAGAGACT GGAAGGGTTA     1800

CAGGAGGCTG AGTTACGTGA TCTAGTGAGA GAGGCAGAGA AGGTGTATTA CAGAAGGGAG     1860

ACAGAAGAGG AGAAGGAACA GAGAAAAGAA AAGGAGAGAG AAGAAAGGGA GGAAAGACGT     1920

GATAGACGGC AAGAGAAGAA TTTGACTAAG ATCTTGGCCG CAGTGGTTGA AGGGAAGAGC     1980

AGCAGGGAGA GAGAGAGAGA TTTTAGGAAA ATTAGGTCAG GCCCTAGACA GTCAGGGAAC     2040

CTGGGCAATA GGACCCCACT CGACAAGGAC CAGTGTGCGT ATTGTAAAGA AAAAGGACAC     2100

TGGGCAAGGA ACTGCCCCAA GAAGGGAAAC AAAGGACCGA AGGTCCTAGC TCTAGAAGAA     2160

GATAAAGATT AGGGGAGACG GGGTTCGGAC CCCCTCCCCG AGCCCAGGGT AACTTTGAAG     2220

GTGGAGGGGC AACCAGTTGA GTTCCTGGTT GATACCGGAG CGGAGCATTC AGTGCTGCTA     2280

CAACCATTAG GAAAACTAAA AGAAAAAAAA TCCTGGGTGA TGGGTGCCAC AGGGCAACGG     2340

CAGTATCCAT GGACTACCCG AAGAACCGTT GACTGGGAG TGGACGGGT AACCCACTCG      2400

TTTCTGGTCA TCCCTGAGTG CCCAGTACCC CTTCTAGGTA GAGACTTACT GACCAAGATG     2460
```

```
GGAGCTCAAA TTTCTTTTGA ACAAGGAAGA CCAGAAGTGT CTGTGAATAA CAAACCCATC    2520

ACTGTGTTGA CCCTCCAATT AGATGATGAA TATCGACTAT ATTCTCCCCA AGTAAAGCCT    2580

GATCAAGATA TACAGTCCTG GTTGGAGCAG TTTCCCCAAG CCTGGGCAGA AACCGCAGGG    2640

ATGGGTTTGG CAAAGCAAGT TCCCCCACAG GTTATTCAAC TGAAGGCCAG TGCTACACCA    2700

GTATCAGTCA GACAGTACCC CTTGAGTAGA GAGGCTCGAG AAGGAATTTG GCCGCATGTT    2760

CAAAGATTAA TCCAACAGGG CATCCTAGTT CCTGTCCAAT CCCCTTGGAA TACTCCCCTG    2820

CTACCGGTTA GGAAGCCTGG GACCAATGAT TATCGACCAG TACAGGACTT GAGAGAGGTC    2880

AATAAAAGGG TGCAGGACAT ACACCCAACG GTCCCGAACC CTTATAACCT CTTGAGCGCC    2940

CTCCCGCCTG AACGGAACTG GTACACAGTA TTGGACTTAA AAGATGCCTT CTTCTGCCTG    3000

AGATTACACC CCACTAGCCA ACCACTTTTT ACCTTCGAAT GGAGAGATCC AGGTACGGGA    3060

AGAACCGGGC AGCTCACCTG GACCCGACTG CCCCAAGGGT TCAAGAACTC CCCGACCATC    3120

TTTGACGAAG CCCTACACAG GGACCTGGCC AACTTCAGGA TCCAACACCC TCAGGTGACC    3180

CTCCTCCAGT ACGTGGATGA CCTGCTTCTG GCGGGAGCCA CCAAACAGGA CTGCTTAGAA    3240

GGTACGAAGG CACTACTGCT GGAATTGTCT GACCTAGGCT ACAGAGCCTC TGCTAAGAAG    3300

GCCCAGATTT GCAGGAGAGA GGTAACATAC TTGGGGTACA GTTTGCGGGG CGGGCAGCGA    3360

TGGCTGACGG AGGCACGGAA GAAAACTGTA GTCCAGATAC CGGCCCCAAC CACAGCCAAA    3420

CAAGTGAGAG AGTTTTTGGG GACAGCTGGA TTTTGCAGAC TGTGGATCCC GGGGTTTGCG    3480

ACCTTAGCAG CCCCACTCTA CCCGCTAACC AAAGAAAAAG GGGGTTGCTT ACCTCAGCAG    3540

GGAGGGAAAT AAAGAACAAA GAGGAAATTC TAAGCCTATT AGAAGCCTTA CATTTGCCAA    3600

AAAGGCTAGC TATTATACAC TGTCCTGGAC ATCAGAAAGC CAAAGATCTC ATATCTAGAG    3660

GGAACCAGAT GGCTGACCGG GTTGCCAAGC AGGCAGCCCA GGCTGTTAAC CTTCTGCCTA    3720

TAATAGAAAC GCCCAAAGCC CCAGAACCCA GACGACAGTA CACCCTAGAA GACTGGCAAG    3780

AGATAAAAAA GATAGACCAG TTCTCTGAGA CTCCGGAGGG GACCTGCTAT ACCTCATATG    3840

GGAAGGAAAT CCTGCCCCAC AAAGAAGGGT TAGAATATGT CCAACAGATA CATCGTCTAA    3900

CCCACCTAGG AACTAAACAC TGCAGCAGT TGGTCAGAAC ATCCCCTTAT CATGTTCTGA    3960

GGCTACCAGG AGTGGCTGAC TCGGTGGTCA AACATTGTGT GCCCTGCCAG CTGGTTAATG    4020

CTAATCCTTC CAGAATACCT CCAGGAAAGA GACTAAGGGG AAGCCACCCA GGCGCTCACT    4080

GGGAAGTGGA CTTCACTGAG GTAAAGCCGG CTAAATACGG AAACAAATAT CTATTGGTTT    4140

TTGTAGACAC CTTTTCAGGA TGGGTAGAGG CTTATCCTAC TAAAAAAGAG ACTTCAACCG    4200

TGGTGGCTAA GAAAATACTG GAGGAAATTT TTCCAAGATT TGGAATACCT AAGGTAATAG    4260

GGTCAGACAA TGGTCCAGCT TTCGTTGCCC AGGTAAGTCA GGGACTGGCC AAGATATTGG    4320

GGATTGATTG AAAACTGCAT TGTGCATACA GACCCCAAAG CTCAGGACAG GTAGAGAGGA    4380

TGAATAGAAC CATTAAAGAG ACCCTTACCA AATTGACCAC AGAGACTGGC ATTAATGATT    4440

GGATGGCTCT CCTGCCCTTT GTGCTTTTTA GGGTGAGGAA CACCCCTGGA CAGTTTGGGC    4500

TGACCCCCTA TAAATTGCTC TACGGGGAC CCCCCCCGTT GGCAGAAATT GCCTTTGCAC    4560

ATAGTGCTGA TGTGCTGCTT TCCCAGCCTT TGTTCTCTAG GCTCAAGGCG CTCGAGTGGG    4620

TGAGGCAGCG AGCGTGGAAG CAGCTCCGGG AGGCCTACTC AGGAGGAGAC TTGCAAGTTC    4680

CACATCGCTT CCAAGTTGGA GATTCAGTCT ATGTTAGACG CCACCGTGCA GGAAACCTCG    4740

AGACTCGGTA GAAGGGACCT TATCTCGTAC TTTTGACCAC ACCAACGGCT GTGAAAGTCG    4800

AAGGAATCCC CTTAAGCTTC GCCTCCATCG CGTGGTTCCT TACTCTGTCA ATAACTCCTC    4860
```

-continued

```
AAGTTAATGG TAAACGCCTT GTGGACAGCC CGAACTCCCA TAAACCCTTA TCTCTCACCT    4920
GGTTACTTAC TGACTCCGGT ACAGGTATTA ATATTAACAG CACTCAAGGG GAGGCTCCCT    4980
TGGGGACCTG GTGGCCTGAA TTATATGTCT GCCTTCGATC AGTAATCCCT GGTCTCAATG    5040
ACCAGGCCAC ACCCCCCGAT GTACTCCGTG CTTACGGGTT TTACGTTTGC CCAGGACCCC    5100
CAAATAATGA AGAATATTGT GGAAATCCTC AGGATTTCTT TTGCAAGCAA TGGAGCTGCA    5160
TAACTTCTAA TGATGGGAAT TGGAAATGGC CAGTCTCTCA GCAAGACAGA GTAAGTTACT    5220
CTTTTGTTAA CAATCCTACC AGTTATAATC AATTTAATTA TGGCCATGGG AGATGGAAAG    5280
ATTGGCAACA GCGGGTACAA AAAGATGTAC GAAATAAGCA AATAAGCTGT CATTCGTTAG    5340
ACCTAGATTA CTTAAAAATA AGTTTCACTG AAAAAGGAAA ACAAGAAAAT ATTCAAAAGT    5400
GGGTAAATGG TATATCTTGG GGAATAGTGT ACTATGGAGG CTCTGGGAGA AGAAAGGAT    5460
CTGTTCTGAC TATTCGCCTC AGAATAGAAA CTCAGATGGA ACCTCCGGTT GCTATAGGAC    5520
CAAATAAGGG TTTGGCCGAA CAAGGACCTC CAATCCAAGA ACAGAGGCCA TCTCCTAACC    5580
CCTCTGATTA CAATACAACC TCTGGATCAG TCCCCACTGA GCCTAACATC ACTATTAAAA    5640
CAGGGGCGAA ACTTTTTAGC CTCATCCAGG GAGCTTTTCA AGCTCTTAAC TCCACGACTC    5700
CAGAGGCTAC CTCTTCTTGT TGGCTTTGCT TAGCTTCGGG CCCACCTTAC TATGAGGGAA    5760
TGGCTAGAGG AGGGAAATTC AATGTGACAA AGGAACATAG AGACCAATGT ACATGGGGAT    5820
CCCAAAATAA GCTTACCCTT ACTGAGGTTT CTGGAAAAGG CACCTGCATA GGATGGTTC    5880
CCCCATCCCA CCAACACCTT TGTAACCACA CTGAAGCCTT TAATCGAACC TCTGAGAGTC    5940
AATATCTGGT ACCTGGTTAT GACAGGTGGT GGGCATGTAA TACTGGATTA ACCCCTTGTG    6000
TTTCCACCTT GGTTTTCAAC CAAACTAAAG ACTTTTGCGT TATGGTCCAA ATTGTCCCCC    6060
GGGTGTACTA CTATCCCGAA AAAGCAGTCC TTGATGAATA TGACTATAGA TATAATCGGC    6120
CAAAAAGAGA GCCCATATCC CTGACACTAG CTGTAATGCT CGGATTGGGA GTGGCTGCAG    6180
GCGTGGGAAC AGGAACGGCT GCCCTAATCA CAGGACCGCA ACAGCTGGAG AAAGGACTTA    6240
GTAACCTACA TCGAATTGTA ACGGAAGATC TCCAAGCCCT AGAAAAATCT GTCAGTAACC    6300
TGGAGGAATC CCTAACCTCC TTATCTGAAG TGGTTCTACA GAACAGAAGG GGGTTAGATC    6360
TGTTATTTCT AAAAGAAGGA GGGTTATGTG TAGCCTTAAA AGAGGAATGC TGCTTCTATG    6420
TAGATCACTC AGGAGCCATC AGAGACTCCA TGAGCAAGCT TAGAGAAAGG TTAGAGAGGC    6480
GTCGAAGGGA AAGAGAGGCT GACCAGGGGT GGTTTGAAGG ATGGTTCAAC AGGTCTCCTT    6540
GGATGACCAC CCTGCTTTCT GCTCTGACGG GGCCCCTAGT AGTCCTGCTC CTGTTACTTA    6600
CAGTTGGGCC TTGCTTAATT AATAGGTTTG TTGCCTTTGT TAGAGAACGA GTGAGTGCAG    6660
TCCAGATCAT GGTACTTAGG CAACAGTACC AAGGCCTTCT GAGCCAAGGA GAAACTGACC    6720
TCTAGCCTTC CCAGTTCTAA GATTAGAACT ATTAACAAGA CAAGAAGTGG GGAATGAAAG    6780
GATGAAAATG CAACCTAACC CTCCCAGAAC CCAGGAAGTT AATAAAAAGC TCTAAATGCC    6840
CCCGAATTCC AGACCCTGCT GGCTGCCAGT AAATAGGTAG AAGGTCACAC TTCCTATTGT    6900
TCCAGGGCCT GCTATCCTGG CCTAAGTAAG ATAACAGGAA ATGAGTTGAC TAATCGCTTA    6960
TCTGGATTCT GTAAAACTGA CTGGCACCAT AGAAGAATTG ATTACACATT GACAGCCCTA    7020
GTGACCTATC TCAACTGCAA TCTGTCACTC TGCCCAGGAG CCCACGCAGA TGCGGACCTC    7080
CGGAGCTATT TTAAAATGAT TGGTCCACGG AGCGCGGGCT CTCGATATTT TAAAATGATT    7140
GGTCCATGGA GCGCGGGCTC TCGATATTTT AAAATGATTG GTTGTGACG CACAGGCTTT    7200
```

-continued

```
GTTGTGAACC CCATAAAAGC TGTCCCGATT CCGCACTCGG GGCCGCAGTC CTCTACCCCT      7260

GCGTGGTGTA CGACTGTGGG CCCCAGCGCG CTTGGAATAA AAATCCTCTT GCTGTTTGCA      7320

TCAAAAAAAA AAA                                                        7333
```

(2) INFORMATION FOR SEQ ID NO: 3:

(i) SEQUENCE CHARACTERISTICS:
        (A) LENGTH: 8132 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

```
GCGTGGTGTA CGACTGTGGG CCCCAGCGCG CTTGGAATAA AAATCCTCTT GCTGTTTGCA        60

TCAAGACCGC TTCTCGTGAG TGATTAAGGG GAGTCGCCTT TTCCGAGCCT GGAGGTTCTT       120

TTTGCTGGTC TTACATTTGG GGGCTCGTCC GGGATCTGTC GCGGCCACCC CTAACACCCG       180

AGAACCGACT TGGAGGTAAA AAGGATCCTC TTTTTAACGT GTATGCATGT ACCGGCCGGC       240

GTCTCTGTTC TGAGTGTCTG TTTTCAGTGG TGCGCGCTTT CGGTTTGCAG CTGTCCTCTC       300

AGGCCGTAAG GGCTGGGGGA CTGTGATCAG CAGACGTGCT AGGAGGATCA CAGGCTGCTG       360

CCCTGGGGGA CGCCCCGGGA GGTGAGGAGA GCCAGGGACG CCTGGTGGTC TCCTACTGTC       420

GGTCAGAGGA CCGAATTCTG TTGCTGAAGC GAAAGCTTCC CCCTCCGCGA CCGTCCGACT       480

CTTTTGCCTG CTTGTGGAAG ACGTGGACGG GTCACGTGTG TCTGGATCTG TTGGTTTCTG       540

TTTTGTGTGT CTTTGTCTTG TGTGTCCTTG TCTACAGTTT TAATATGGGA CAGACGGTGA       600

CGACCCCTCT TAGTTTGACT CTCGACCATT GGACTGAAGT TAAATCCAGG GCTCATAATT       660

TGTCAGTTCA GGTTAAGAAG GGACCTTGGC AGACTTTCTG TGTCTCTGAA TGGCCGACAT       720

TCGATGTTGG ATGGCCATCA GAGGGGACCT TTAATTCTGA GATTATCCTG GCTGTTAAAG       780

CAGTTATTTT TCAGACTGGA CCCGGCTCTC ATCCCGATCA GGAGCCCTAT ATCCTTACGT       840

GGCAAGATTT GGCAGAGGAT CCTCCGCCAT GGGTTAAACC ATGGCTGAAT AAGCCAAGAA       900

AGCCAGGTCC CCGAATTCTG GCTCTTGGAG AGAAAAACAA ACACTCGGCT GAAAAAGTCA       960

AGCCCTCTCC TCATATCTAC CCCGAGATTG AGGAGCCACC GGCTTGGCCG GAACCCCAAT      1020

CTGTTCCCCC ACCCCCTTAT CTGGCACAGG GTGCCGCGAG GGGACCCTTT GCCCCTCCTG      1080

GAGCTCCGGC GGTGGAGGGA CCTGCTGCAG GGACTCGGAG CCGGAGGGGC GCCACCCCGG      1140

AGCGGACAGA CGAGATCGCG ACATTACCGC TGCGCACGTA CGGCCCTCCC ACACCGGGGG      1200

GCCAATTGCA GCCCCTCCAG TATTGGCCCT TTTCTTCTGC AGATCTCTAT AATTGGAAAA      1260

CTAACCATCC CCCTTTCTCG GAGGATCCCC AACGCCTCAC GGGGTTGGTG GAGTCCCTTA      1320

TGTTCTCTCA CCAGCCTACT TGGGATGATT GTCAACAGCT GCTGCAGACA CTCTTCACAA      1380

CCGAGGAGCG AGAGAGAATT CTATTAGAGG CTAGAAAAAA TGTTCCTGGG GCCGACGGGC      1440

GACCCACGCG GTTGCAAAAT GAGATTGACA TGGGATTTCC CTTAACTCGC CCCGGTTGGG      1500

ACTACAACAC GGCTGAAGGT AGGGAGAGCT TGAAAATCTA TCGCCAGGCT CTGGTGGCGG      1560

GTCTCCGGGG CGCCTCAAGA CGGCCCACTA ATTGGCTAA GTAAGAGAA GTGATGCAGG       1620

GACCGAATGA ACCCCCTCT GTTTTTCTTG AGAGGCTCTT GGAAGCCTTC AGGCGGTACA       1680

CCCCTTTTGA TCCCACCTCA GAGGCCCAAA AAGCCTCAGT GGCTTTGGCC TTTATAGGAC      1740

AGTCAGCCTT GGATATTAGA AAGAAGCTTC AGAGACTGGA AGGGTTACAG GAGGCTGAGT      1800
```

-continued

```
TACGTGATCT AGTGAAGGAG GCAGAGAAAG TATATTACAA AAGGGAGACA GAAGAAGAAA    1860

GGGAACAAAG AAAAGAGAGA GAAAGAGAGG AAAGGGAGGA AGACGTAAT AAACGGCAAG     1920

AGAAGAATTT GACTAAGATC TTGGCTGCAG TGGTTGAAGG GAAAAGCAAT ACGGAAAGAG    1980

AGAGAGATTT TAGGAAAATT AGGTCAGGCC CTAGACAGTC AGGGAACCTG GCAATAGGA    2040

CCCCACTCGA CAAGGACCAA TGTGCATATT GTAAAGAAAG AGGACACTGG GCAAGGAACT   2100

GCCCCAAGAA GGGAAACAAA GGACCAAGGA TCCTAGCTCT AGAAGAAGAT AAAGATTAGG   2160

GGAGACGGGG TTCGGACCCC CTCCCCGAGC CCAGGGTAAC TTTGAAGGTG GAGGGGCAAC   2220

CAGTTGAGTT CCTGGTTGAT ACCGGAGCGA ACATTCAGT GCTACTACAG CCATTAGGAA    2280

AACTAAAAGA TAAAAAATCC TGGGTGATGG GTGCCACAGG GCAACAACAG TATCCATGGA   2340

CTACCCGAAG AACAGTTGAC TTGGGAGTGG GACGGGTAAC CCACTCGTTT CTGGTCATAC   2400

CTGAGTGCCC AGCACCCCTC TTAGGTAGAG ACTTATTGAC CAAGATGGGA GCACAAATTT   2460

CTTTTGAACA AGGGAAACCA GAAGTGTCTG CAAATAACAA ACCTATCACT GTGTTGACCC   2520

TCCAATTAGA TGACGAATAT CGACTATACT CTCCCCTAGT AAAGCCTGAT CAAAATATAC   2580

AATTCTGGTT GGAACAGTTT CCCCAAGCCT GGGCAGAAAC CGCAGGGATG GGTTTGGCAA   2640

AGCAAGTTCC CCCACAAGTT ATTCAACTGA AGGCCAGTGC CACACCAGTG TCAGTCAGAC   2700

AGTACCCCTT GAGTAAAGAA GCTCAAGAAG GAATTCGGCC GCATGTCCAA AGATTAATCC   2760

AACAGGGCAT CCTAGTTCCT GTCCAATCTC CCTGGAATAC TCCCCTGCTA CCGGTTAGAA   2820

AGCCTGGGAC TAATGACTAT CGACCAGTAC AGGACTTGAG AGAGGTCAAT AAACGGGTGC   2880

AGGATATACA CCCAACAGTC CCGAACCCTT ATAACCTCTT GTGTGCTCTC CCACCCCAAC   2940

GGAGCTGGTA TACAGTATTG GACTTAAAGG ATGCTTCTT CTGCCTGAGA TTACACCCCA    3000

CTAGCCAACC ACTTTTTGCC TTCGAATGGA GAGATCCAGG TACGGAAGA ACCGGGCAGC    3060

TCACCTGGAC CCGACTGCCC CAAGGGTTCA AGAACTCCCC GACCATCTTT GACGAAGCCC   3120

TACACAGAGA CCTGGCCAAC TTCAGGATCC AACACCCTCA GGTGACCCTC CTCCAGTACG   3180

TGGATGACCT GCTTCTGGCG GGAGCCACCA ACAGGACTG CTTAGAAGGC ACGAAGGCAC    3240

TACTGCTGGA ATTGTCTGAC CTAGGCTACA GAGCCTCTGC TAAGAAGGCC CAGATTTGCA   3300

GGAGAGAGGT AACATACTTG GGGTACAGTT TGCGGGACGG GCAGCGATGG CTGACGGAGG   3360

CACGGAAGAA AACTGTAGTC CAGATACCGG CCCCAACCAC AGCCAAACAA ATGAGAGAGT   3420

TTTTGGGGAC AGCTGGATTT TGCAGACTGT GGATCCCGGG GTTTGCGACC TTAGCAGCCC   3480

CACTCTACCC GCTAACCAAA GAAAAGGGG AATTCTCCTG GGCTCCTGAG CACCAGAAGG    3540

CATTTGATGC TATCAAAAAG GCCCTGCTGA GCGCACCTGC TCTGGCCCTC CCTGACGTAA   3600

CTAAACCCTT TACCCTTTAT GTGGATGAGC GTAAGGGAGT AGCCCGGGGA GTTTTAACCC   3660

AAACCCTAGG ACCATGGAGA AGACCTGTCG CCTACCTGTC AAAGAAGCTC GATCCTGTAG   3720

CCAGTGGTTG GCCCATATGC CTGAAGGCTA TCGCAGCTGT GGCCATACTG GTCAAGGACG   3780

CTGACAAATT GACTTTGGGA CAGAATATAA CTGTAATAGC CCCCCATGCA TTGGAGAACA   3840

TCGTTCGGCA GCCCCCAGAC CGATGGATGA CCAACGCCCG CATGACCCAC TATCAAAGCC   3900

TGCTTCTCAC AGAGAGGGTC ACGTTCGCTC CACCAGCCGC TCTCAACCCT GCCACTCTTC   3960

TGCCTGAAGA GACTGATGAA CCAGTGACTC ATGATTGCCA TCAACTATTG ATTGAGGAGA   4020

CTGGGGTCCG CAAGGACCTT ACAGACATAC CGCTGACTGG AGAAGTGCTA ACCTGGTTCA   4080

CTGACGGAAG CAGCTATGTG GTGGAAGGTA AGAGGATGGC TGGGCGGCG GTGGTGGACG    4140

GGACCCGCAC GATCTGGGCC AGCAGCCTGC CGGAAGGAAC TTCAGCACAA AAGGCTGAGC   4200
```

```
TCATGGCCCT CACGCAAGCT TTGCGGCTGG CCGAAGGGAA ATCCATAAAC ATTTATACGG    4260

ACAGCAGGTA TGCCTTTGCG ACTGCACACG TACATGGGGC CATCTATAAA CAAAGGGGGT    4320

TGCTTACCTC AGCAGGGAGG GAAATAAAGA ACAAAGAGGA AATTCTAAGC CTATTAGAAG    4380

CCGTACATTT ACCAAAAAGG CTAGCTATTA TACACTGTCC TGGACATCAG AAAGCTAAAG    4440

ATCTCATATC CAGAGGAAAC CAGATGGCTG ACCGGGTTGC CAAGCAGGCA GCCCAGGGTG    4500

TTAACCTTCT GCCTATAATA GAAATGCCCA AGCCCCAGA ACCCAGACGA CAGTACACCC     4560

TAGAAGACTG GCAAGAGATA AAAAGATAG ACCAGTTCTC TGAGACTCCG GAAGGGACCT     4620

GCTATACCTC AGATGGGAAG GAAATCCTGC CCCACAAAGA AGGGTTAGAA TATGTCCAAC    4680

AGATACATCG TCTAACCCAC CTAGGAACTA AACACCTGCA GCAGTTGGTC AGAACATCCC    4740

CTTATCATGT TCTGAGGCTA CCAGGAGTGG CTGACTCGGT GGTCAAACAT TGTGTGCCCT    4800

GCCAGCTGGT TAATGCTAAT CCTTCCAGAA TGCCTCCAGG GAAGAGACTA AGGGGAAGCC    4860

ACCCAGGCGC TCACTGGGAA GTGGACTTCA CTGAGGTAAA GCCGGCTAAA TACGGAAACA    4920

AATACCTATT GGTTTTTGTA GACACCTTTT CAGGATGGGT AGAGGCTTAT CCTACTAAGA    4980

AAGAGACTTC AACCGTGGTG GCTAAAAAAA TACTGGAAGA AATTTTTCCA AGATTTGGAA    5040

TACCTAAGGT AATAGGGTCA GACAATGGTC CAGCTTTTGT TGCCCAGGTA AGTCAGGGAC    5100

TGGCCAAGAT ATTGGGGATT GATTGGAAAC TGCATTGTGC ATACAGACCC CAAAGCTCAG    5160

GACAGGTAGA GAGGATGAAT AGAACCATTA AAGAGACCCT TACTAAATTG ACCGCGGAGA    5220

CTGGCGTTAA TGATTGGATA GCTCTCCTGC CCTTTGTGCT TTTTAGGGTT AGGAACACCC    5280

CTGGACAGTT TGGGCTGACC CCCTATGAAT TACTCTACGG GGGACCCCCC CCATTGGTAG    5340

AAATTGCTTC TGTACATAGT GCTGACGTGC TGCTTTCCCA GCCTTTGTTC TCTAGGCTCA    5400

AGGCACTTGA GTGGGTGAGA CAACGAGCGT GGAGGCAACT CCGGGAGGCC TACTCAGGAG    5460

GAGGAGACTT GCAGATCCCA CATCGTTTCC AAGTGGGAGA TTCAGTCTAC GTTAGACGCC    5520

ACCGTGCAGG AAACCTCGAG ACTCGGTGGA AGGGCCCTTA TCTCGTACTT TTGACCACAC    5580

CAACGGCTGT GAAAGTCGAA GGAATCTCCA CCTGGATCCA TGCATCCCAC GTTAAACCGG    5640

CGCCACCTCC CGATTCGGGG TGGAAAGCCG AAAAGACTGA AAATCCCCTT AAGCTTCGCC    5700

TCCATCGCGT GGTTCCTTAC TCTGTCAATA ACCTCTCAGA CTAATGGTAT GCGCATAGGA    5760

GACAGCCTGA ACTCCCATAA ACCCTTATCT CTCACCTGGT TAATTACTGA CTCCGGCACA    5820

GGTATTAATA TCAACAACAC TCAAGGGGAG GCTCCTTTAG GAACCTGGTG GCCTGATCTA    5880

TACGTTTGCC TCAGATCAGT TATTCCTAGT CTGACCTCAC CCCCAGATAT CCTCCATGCT    5940

CACGGATTTT ATGTTTGCCC AGGACCACCA AATAATGGAA AACATTGCGG AAATCCCAGA    6000

GATTTCTTTT GTAAACAATG GAACTGTGTA ACCTCTAATG ATGGATATTG GAAATGGCCA    6060

ACCTCTCAGC AGGATAGGGT AAGTTTTTCT TATGTCAACA CCTATACCAG CTCTGGACAA    6120

TTTAATTACC TGACCTGGAT TAGAACTGGA AGCCCCAAGT GCTCTCCTTC AGACCTAGAT    6180

TACCTAAAAA TAAGTTTCAC TGAGAAAGGA AACAAGAAA ATATCCTAAA ATGGGTAAAT    6240

GGTATGTCTT GGGGAATGGT ATATTATGGA GGCTCGGGTA ACAACCAGG CTCCATTCTA     6300

ACTATTCGCC TCAAAATAAA CCAGCTGGAG CCTCCAATGG CTATAGGACC AAATACGGTC    6360

TTGACGGGTC AAAGACCCCC AACCCAAGGA CCAGGACCAT CCTCTAACAT AACTTCTGGA    6420

TCAGACCCCA CTGAGTCTAA CAGCACGACT AAAATGGGGG CAAAACTTTT TAGCCTCATC    6480

CAGGGAGCTT TTCAAGCTCT TAACTCCACG ACTCCAGAGG CTACCTCTTC TTGTTGGCTA    6540
```

-continued

```
TGCTTAGCTT CGGGCCCACC TTACTATGAA GGAATGGCTA GAAGAGGGAA ATTCAATGTG    6600

ACAAAAGAAC ATAGAGACCA ATGCACATGG GGATCCCAAA ATAAGCTTAC CCTTACTGAG    6660

GTTTCTGGAA AAGGCACCTG CATAGGAAAG GTTCCCCCAT CCCACCAACA CCTTTGTAAC    6720

CACACTGAAG CCTTTAATCA AACCTCTGAG AGTCAATATC TGGTACCTGG TTATGACAGG    6780

TGGTGGGCAT GTAATACTGG ATTAACCCCT TGTGTTTCCA CCTTGGTTTT TAACCAAACT    6840

AAAGATTTTT GCATTATGGT CCAAATTGTT CCCCGAGTGT ATTACTATCC CGAAAAAGCA    6900

ATCCTTGATG AATATGACTA CAGAAATCAT CGACAAAAGA GAGAACCCAT ATCTCTGACA    6960

CTTGCTGTGA TGCTCGGACT TGGAGTGGCA GCAGGTGTAG AACAGGAAC AGCTGCCCTG     7020

GTCACGGGAC CACAGCAGCT AGAAACAGGA CTTAGTAACC TACATCGAAT TGTAACAGAA    7080

GATCTCCAAG CCCTAGAAAA ATCTGTCAGT AACCTGGAGG AATCCCTAAC CTCCTTATCT    7140

GAAGTAGTCC TACAGAATAG AAGAGGGTTA GATTTATTAT TTCTAAAAGA AGGAGGATTA    7200

TGTGTAGCCT TGAAGGAGGA ATGCTGTTTT TATGTGGATC ATTCAGGGGC CATCAGAGAC    7260

TCCATGAACA AGCTTAGAGA AAGGTTGGAG AAGCGTCGAA GGGAAAAGGA AACTACTCAA    7320

GGGTGGTTTG AGGGATGGTT CAACAGGTCT CTTTGGTTGG CTACCCTACT TTCTGCTTTA    7380

ACAGGACCCT TAATAGTCCT CCTCCTGTTA CTCACAGTTG GGCCATGTAT TATTAACAAG    7440

TTAATTGCCT TCATTAGAGA ACGAATAAGT GCAGTCCAGA TCATGGTACT TAGACAACAG    7500

TACCAAAGCC CGTCTAGCAG GGAAGCTGGC CGCTAGCTCT ACCAGTTCTA AGATTAGAAC    7560

TATTAACAAG AGAAGAAGTG GGGAATGAAA GGATGAAAAT ACAACCTAAG CTAATGAGAA    7620

GCTTAAAATT GTTCTGAATT CCAGAGTTTG TTCCTTATAG GTAAAAGATT AGGTTTTTTG    7680

CTGTTTTAAA ATATGCGGAA GTAAAATAGG CCCTGAGTAC ATGTCTCTAG GCATGAAACT    7740

TCTTGAAACT ATTTGAGATA ACAAGAAAAG GGAGTTTCTA ACTGCTTGTT TAGCTTCTGT    7800

AAAACTGGTT GCGCCATAAA GATGTTGAAA TGTTGATACA CATATCTTGG TGACAACATG    7860

TCTCCCCCAC CCCGAAACAT GCGCAAATGT GTAACTCTAA AACAATTTAA ATTAATTGGT    7920

CCACGAAGCG CGGGCTCTCG AAGTTTTAAA TTGACTGGTT TGTGATATTT TGAAATGATT    7980

GGTTTGTAAA GCGCGGGCTT TGTTGTGAAC CCCATAAAAG CTGTCCCGAC TCCACACTCG    8040

GGGCCGCAGT CCTCTACCCC TGCGTGGTGT ACGACTGTGG GCCCCAGCGC GCTTGGAATA    8100

AAAATCCTCT TGCTGTTTGC ATCAAAAAAA AA                                  8132
```

(2) INFORMATION FOR SEQ ID NO: 4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

```
TGCCTAGAGA CATGTACTC                                                   19
```

(2) INFORMATION FOR SEQ ID NO: 5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

CCTCTTCTAG CCATTCCTTC A                                            21

(2) INFORMATION FOR SEQ ID NO: 6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

TCGAGACTCG GTGGAAGGGC CC                                           22

(2) INFORMATION FOR SEQ ID NO: 7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

GGGCCCTTCC ACCGAGTCTC GA                                           22

(2) INFORMATION FOR SEQ ID NO: 8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

ACCTGGATCC ATGCATCCCA CG                                           22

(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

CGTGGGATGC ATGGATCCAG GT                                           22

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

GGCGCCACCT CCCGATTCGG                                              20

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

CCGAATCGGG AGGTGGCGCC                                      20

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

TCCCCTTAAG CTTCGCCTCC                                      20

(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

GGAGGCGAAG CTTAAGGGGA                                      20

(2) INFORMATION FOR SEQ ID NO: 14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

AAAAGCACAA AGGGCAGGAG AGC                                  23

(2) INFORMATION FOR SEQ ID NO: 15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

GCTCTCCTGC CCTTTGTGCT TTT                                  23

(2) INFORMATION FOR SEQ ID NO: 16:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 16:

CCTTTAGGAA CCTGGTGGCC                                               20

(2) INFORMATION FOR SEQ ID NO: 17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

GGCCACCAGG TTCCTAAAGG                                               20

(2) INFORMATION FOR SEQ ID NO: 18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

CCCCCAGATA TCCTCCATGC                                               20

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

GCATGGAGGA TATCTGGGGG                                               20

(2) INFORMATION FOR SEQ ID NO: 20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

GCAGTTTCCA ATCAATCCCC AA                                            22

(2) INFORMATION FOR SEQ ID NO: 21:

(i) SEQUENCE CHARACTERISTICS:
        (A) LENGTH: 22 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO: 21:

TTGGGGATTG ATTGGAAACT GC                                                22

(2) INFORMATION FOR SEQ ID NO: 22:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

TTTATGTTTG CCCAGGACCA CCA                                               23

(2) INFORMATION FOR SEQ ID NO: 23:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

TGGTGGTCCT GGGCAAACAT AAA                                               23

(2) INFORMATION FOR SEQ ID NO: 24:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

GGGAGGTGGC GCCGGCTTAA CGT                                               23

(2) INFORMATION FOR SEQ ID NO: 25:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

ACGTTAAGCC GGCGCCACCT CCC                                               23

(2) INFORMATION FOR SEQ ID NO: 26:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 26:

CCCCCAACCC AAGGACCAGG ACCA                                              24

(2) INFORMATION FOR SEQ ID NO: 27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 27:

TGGTCCTGGT CCTTGGGTTG GGGG                                              24

(2) INFORMATION FOR SEQ ID NO: 28:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 28:

GCAGCACGAC TAAAATGGGG GC                                                22

(2) INFORMATION FOR SEQ ID NO: 29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 29:

GCCCCCATTT TAGTCGTGCT GC                                                22

(2) INFORMATION FOR SEQ ID NO: 30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 30:

CCCCCATCCC ACCAACACCT                                                   20

(2) INFORMATION FOR SEQ ID NO: 31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 31:

AGGTGTTGGT GGGATGGGGG                                                   20

(2) INFORMATION FOR SEQ ID NO: 32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 32:

TCTCCCCCAC CCCGAAACAT                                              20

(2) INFORMATION FOR SEQ ID NO: 33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 33:

ATGTTTCGGG GTGGGGAGA                                               20

(2) INFORMATION FOR SEQ ID NO: 34:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 34:

AGCCAAGAAA GCCAGGTCCC CGAA                                      24

(2) INFORMATION FOR SEQ ID NO: 35:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 35:

TTCGGGGACC TGGCTTTCTT GGCT                                      24

(2) INFORMATION FOR SEQ ID NO: 36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 36:

AGGCTCTGGT GGCGGGTCTC C                                            21

(2) INFORMATION FOR SEQ ID NO: 37:

(i) SEQUENCE CHARACTERISTICS:

(A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 37:

GGAGACCCGC CACCAGAGCC T                                                    21

(2) INFORMATION FOR SEQ ID NO: 38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 38:

CCGCAGGGAT GGGTTTGGCA                                                      20

(2) INFORMATION FOR SEQ ID NO: 39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 39:

TGCCAAACCC ATCCCTGCGG                                                      20

(2) INFORMATION FOR SEQ ID NO: 40:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 40:

GCTCACCTGG ACCCGACTGC CC                                                   22

(2) INFORMATION FOR SEQ ID NO: 41:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 41:

GGGCAGTCGG GTCCAGGTGA GC                                                   22

(2) INFORMATION FOR SEQ ID NO: 42:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 42:

GTTTACGGGA CGGGCAGCGA TGGC                                          24

(2) INFORMATION FOR SEQ ID NO: 43:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 43:

GCCATCGCTG CCCGTCCCGT AAAC                                          24

(2) INFORMATION FOR SEQ ID NO: 44:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 44:

TGGCTGGGGC GGCGGTGGTG GACGGG                                        26

(2) INFORMATION FOR SEQ ID NO: 45:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 45:

CCCGTCCACC ACCGCCGCCC CAGCCA                                        26

(2) INFORMATION FOR SEQ ID NO: 46:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 46:

GCCCAAAGCC CCAGAACCCA GACG                                          24

(2) INFORMATION FOR SEQ ID NO: 47:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 47:

```
CGTCTGGGTT CTGGGGCTTT GGGC                                         24

(2) INFORMATION FOR SEQ ID NO: 48:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 48:

GATGAACAGG CAGACATCTG                                               20

(2) INFORMATION FOR SEQ ID NO: 49:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 49:

CGCTTACAGA CAAGCTGTGA                                               20

(2) INFORMATION FOR SEQ ID NO: 50:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 50:

AGAACAAAGG CTGGGAAGC                                                19

(2) INFORMATION FOR SEQ ID NO: 51:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 51:

ATAGGAGACA GCCTGAACTC                                               20

(2) INFORMATION FOR SEQ ID NO: 52:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 52:

GGACCATTGT CTGACCCTAT                                               20
```

(2) INFORMATION FOR SEQ ID NO: 53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 53:

GTCAACACCT ATACCAGCTC                                           20

(2) INFORMATION FOR SEQ ID NO: 54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 54:

CATCTGAGGT ATAGCAGGTC                                           20

(2) INFORMATION FOR SEQ ID NO: 55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 55:

GCAGGTGTAG GAACAGGAAC                                           20

(2) INFORMATION FOR SEQ ID NO: 56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 56:

ACCTGTTGAA CCATCCCTCA                                           20

(2) INFORMATION FOR SEQ ID NO: 57:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 57:

CGAATGGAGA GATCCAGGTA                                           20

(2) INFORMATION FOR SEQ ID NO: 58:

(i) SEQUENCE CHARACTERISTICS:
        (A) LENGTH: 20 base pairs (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 58:

CCTGCATCAC TTCTCTTACC                                              20

(2) INFORMATION FOR SEQ ID NO: 59:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 59:

TTGCCTGCTT GTGGAATACG                                              20

(2) INFORMATION FOR SEQ ID NO: 60:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 60:

CAAGAGAAGA AGTGGGGAAT G                                            21

(2) INFORMATION FOR SEQ ID NO: 61:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 61:

CACAGTCGTA CACCACGCAG                                              20

(2) INFORMATION FOR SEQ ID NO: 62:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 62:

GGGAGACAGA AGAAGAAAGG                                              20

(2) INFORMATION FOR SEQ ID NO: 63:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 63:

CGATAGTCAT TAGTCCCAGG                     20

(2) INFORMATION FOR SEQ ID NO: 64:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 64:

TGCTGGTTTG CATCAAGACC G                   21

(2) INFORMATION FOR SEQ ID NO: 65:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 65:

GTCGCAAAGG CATACCTGCT                     20

(2) INFORMATION FOR SEQ ID NO: 66:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 66:

ACAGAGCCTC TGCTAAGAAG                     20

(2) INFORMATION FOR SEQ ID NO: 67:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 67:

GCAGCTGTTG ACAATCATC                      19

(2) INFORMATION FOR SEQ ID NO: 68:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 68:

TATGAGGAGA GGGCTTGACT                                           20

(2) INFORMATION FOR SEQ ID NO: 69:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 69:

AGCAGACGTG CTAGGAGGT                                            19

(2) INFORMATION FOR SEQ ID NO: 70:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 70:

TCCTCTTGCT GTTTGCATC                                            19

(2) INFORMATION FOR SEQ ID NO: 71:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 71:

CAGACACTCA GAACAGAGAC                                           20

(2) INFORMATION FOR SEQ ID NO: 72:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 72:

ACATCGTCTA ACCCACCTAG                                           20

(2) INFORMATION FOR SEQ ID NO: 73:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 73:

CTCGTTTCTG GTCATACCTG A                                         21

(2) INFORMATION FOR SEQ ID NO: 74:

```
    (i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 74:

GAGTACATCT CTCTAGGCA                                                19
```